US008927248B2

(12) United States Patent
Sung

(10) Patent No.: US 8,927,248 B2
(45) Date of Patent: Jan. 6, 2015

(54) MODIFICATION OF XYLANASES TO INCREASE THERMOPHILICITY, THERMOSTABILITY AND ALKALOPHILICITY

(75) Inventor: Wing L. Sung, Gloucester (CA)

(73) Assignee: National Research Council Canada, Ottawa, ON (CA)

( * ) Notice: Subject to any disclaimer, the term of this patent is extended or adjusted under 35 U.S.C. 154(b) by 1264 days.

(21) Appl. No.: 12/253,774

(22) Filed: Oct. 17, 2008

(65) Prior Publication Data

US 2009/0148923 A1 Jun. 11, 2009

Related U.S. Application Data

(63) Continuation of application No. PCT/CA2007/000590, filed on Apr. 10, 2007.

(60) Provisional application No. 60/791,541, filed on Apr. 12, 2006.

(51) Int. Cl.
C12N 9/24 (2006.01)
D21H 17/00 (2006.01)
D21C 5/00 (2006.01)
D21C 9/10 (2006.01)

(52) U.S. Cl.
CPC ............ *C12N 9/2482* (2013.01); *D21C 9/1036* (2013.01); *D21H 17/005* (2013.01); *C12Y 302/01008* (2013.01); *D21C 5/005* (2013.01)
USPC .......................................... 435/200; 536/23.2

(58) Field of Classification Search
None
See application file for complete search history.

(56) References Cited

U.S. PATENT DOCUMENTS

| 5,078,802 | A | 1/1992 | Imanaka et al. |
| 5,405,769 | A | 4/1995 | Campbell et al. |
| 5,610,046 | A | 3/1997 | van Ooyen et al. |
| 5,759,840 | A | 6/1998 | Sung et al. |
| 5,817,500 | A | 10/1998 | Hansen et al. |
| 5,866,408 | A | 2/1999 | Sung et al. |
| 5,866,526 | A | 2/1999 | Olsen et al. |
| 5,916,795 | A | 6/1999 | Fukunaga et al. |
| 6,228,629 | B1 | 5/2001 | Paloheimo et al. |
| 6,682,923 | B1 | 1/2004 | Bentzien et al. |
| 7,060,482 | B1 | 6/2006 | Sung et al. |
| 7,510,860 | B1 * | 3/2009 | Sung ............................. 435/201 |
| 7,695,947 | B2 | 4/2010 | Sung |
| 2003/0166236 | A1 | 9/2003 | Sung |
| 2005/0271769 | A1 * | 12/2005 | Sibbesen et al. ................ 426/20 |

FOREIGN PATENT DOCUMENTS

| EP | 0473545 | A2 | 3/1992 |
| EP | 0828002 | A2 | 3/1998 |
| EP | 1184460 | A1 | 3/2002 |
| WF | WO 03/106654 | | 10/2003 |
| WO | WO 94/24270 | A2 | 10/1994 |
| WO | WO 95/12668 | A1 | 5/1995 |
| WO | WO 95/34662 | | 12/1995 |
| WO | WO 97/36995 | | 10/1997 |
| WO | WO 00/29587 | A1 | 5/2000 |
| WO | WO 01/27252 | A1 | 4/2001 |
| WO | WO 01/92487 | A2 | 12/2001 |
| WO | WO 03/46169 | A2 | 6/2003 |
| WO | WO 2005/093072 | | 10/2005 |
| WO | WO 2007/115391 | A1 | 10/2007 |

OTHER PUBLICATIONS

Tatu et al., "Role of a Disulfide Cross-Link in the Conformational Stability of a Thermostable Xylanase", 1990, *Journal of Protein Chemistry*, 9(5):1-6.
Tolan et al., "The Use of Enzymes to Decrease the C12 Requirements in Pulp Bleaching", Pulp and Paper Canada, 1992, 93(5): 39-42.
Turunen et al., "Engineering of multiple arginines into the Ser/Thr surface of *Trichoderma reesei* endo-1,4-beta-xylanase II increases the thermotolerance and shifts the pH optimum towards alkaline pH", *Protein Engineering*, 15 (2): 141-145, 2002.
Sowdhamini et al., "Stereochemical modeling of disulfide bridges, Criteria for introduction int proteins by site-direct mutagenesis", *Protein Engineering*, 3(3):95-103, 1989.
Fenel et al., "A de novo designed N-terminal disulphide bridge stabilizes the *Trichoderma reesei* endo-1,4-beta-xylanase II", *Journal of Biotechnology*, 108:137-143, 2004.
Hakulinen et al., "Three-dimensional Structures of Thermophilic beta-1,4-xylanases from *Chaetomium thermophilium* and *Nonomurea flexuosa* Comparison of twelve xylanases in relation to their thermal stability"*Eur. J. Biochem.* 279:1399-1412, 2003.
Fushinoru et al., "Crystallographic and mutational analyses of an extremely acidophilic and acid-stable xylanase biased distribution of acidic residues and importance of Asp37 for catalysis at low pH", *Protein Engineering*, 11(12):1121-1128, 1998.
Ito et al., "Cloning and Sequencing of the xynA Gene Encoding Xylanase A of Aspergillu kawachii" *Biosci. Biotech. Biochem.*, 56(6), 906-912, 1992.
Esteves et al., "Acidophilic adaptation of family II endo-beta-1,4-xylanases: Modeling and mutational analysis", *Protein Science*, (2004), 13:1209-1218.
Dani et al., "MODIP revisited: re-evaluation and refinement of an automated procedure for modeling of disulfide bonds in proteins", *Protein Engineering*, 16(3):187-193, 2003.
Shoemaker et al., "Molecular cloning of exo-cellobiohydrolase I derived from *Trichoderma reesei* strain L27", *Nature biotechnology*, Oct. 1983, 1:691-696.
Chen et al., "Nucleotide Sequence and Deduced Primary Structure of Cellobiohydrolase II from *Trichoderma reesei*", *Nature biotechnology*, 1987, 5:274-278.

(Continued)

*Primary Examiner* — Rebecca Prouty
(74) *Attorney, Agent, or Firm* — Cooley LLP

(57) ABSTRACT

A modified Family 11 xylanase enzyme comprising cysteine residues at positions 99 and 118 to form an intramolecular disulfide bond is provided. The modified xylanase is produced by substitution of an amino acid at position 99, 118 or both positions 99 and 118 with a cysteine to produce the intramolecular disulfide bond. Xylanases of the invention display improved thermophilicity, alkalophilicity or thermostability relative to wild-type xylanases. Such xylanases find use in a variety of applications in industry that require enzyme activities at temperatures and/or pH values above that of the native enzyme.

30 Claims, 21 Drawing Sheets

(56) References Cited

OTHER PUBLICATIONS

Lever, "A Reaction for Colorimetric Determination of Carbohydrates, Analytical Biochemistry", 47:273-279, 1972.
Arase et al. "Stabilization of xylanase by random mutagenesis", 1993, *FEBS Letters*, 316:123-127.
Chandra et al., "A Cellulase-free Xylanase From Alkali-tolerant *Aspergillus fischeri* Fxn1", Mar. 1995, *Biotechnology Letters*, 17(3):309-314.
Creighton "Disulphide bonds and protein stability", Feb. 1988, *Bioessays*, Cambridge, GB, 8(2):57-63.
European Search Report based on European Application No. 07719518.8, (Nov. 16, 2009).
Georis et al., "An additional aromatic interaction improves the thermostability and thermophilicity of a mesophilic family 11 xylanase: structural basis and molecular study." 2000, *Protein Science*, 9(3):466-475.
Gruber et al., "Thermophilic xylanase from *Thermomyces lanuginosus*: high-resolution X-ray structure and modeling studies", Sep. 29, 1998, *Biochemistry*, American Chemical Society, 37(39):13475-13485.
Haki et al. "Developments in Industrially Important Thermostable Enzymes: A Review", 2003, *Bioresource Technol.*, 89:17-34.
International Search Report based on International Application No. PCT/CA2007/000590, (Jul. 24, 2007).
Irwin et al., "Characterization and Sequence of a *Thermomonospora fusca* Xylanase", Mar. 1994, *Applied and Environmental Microbiology*, 60(3):763-770.
Jeferies "Biochemistry and Genetics of Microbial Xylanase", 1996, *Curr. Opin. Biotechnol.* 7:337-342.
Kimura et al. GenBank Accession No. Q9HFA4, Mar. 1, 2001.
Torronen et al. "Three-dimensional structure of endo-1,4-beta-xylanase II from *Trichoderma reesei*: two conformational states in the active site", Jan. 1, 1994, *EMBO Journal*, Oxford University Press, 13(11):2493-2501.
Turunen et al., "A combination of weakly stabilizing mutations with a disulfide bridge in the alpha-helix region of *Trichoderma reesei* endo-1,4-beta-xylanase II increases the thermal stability through synergism", Jan. 2001, *Journal of Biotechnology*, Elsevier Science Publishers, 88(1):37-46.
Wakarchuk et al., "Thermostabilization of the *Bacillus circulans* xylanase by the introduction of disulfide bonds", Jan. 1, 1994, *Protein engineering*, Oxfrod University Press, 7(11):1379-1386.
Kinoshita et al., "Cloning of the xynNB gene encoding xylanase B from *Aspergillus niger* and its expression in *Aspergillus kawachii*", 1995, *Journal of Fermentation and Bioengineering*, 79(5):422-428.
Krengel et al., "Three-dimensional Structure of Endo-1,4-β-xylanase I from Aspergillus niger: Molecular Basis for its Low pH Optimum", 1996, *Journal of Molecular Biology*, 263:70-78.
Lee et al., "Purification and Characterization of Two Endoxylanases from *Clostridium acetobutylicum* ATCC 824", 1987, *Appl. Environ. Microbiol.*, 53(4):644-650.
Luthi et al., "Xylanase from the extremely thermophilic bacterium "*Caldocellum saccharolyticum*": overexpression ,of the gene in *Escherichia coli* and characterization of the gene product." *Appl. Environ. Microbiol.*, 56(9): 2677-2683, 1990.
Mathrani et al., "Thermophilic and alkalophilic xylanases from several *Dictyoglomus* isolates", 1992, *Appl. Microbiol. Biotechnol.* 38:23-27.
Moore et al., "Strategies for the in vitro evolution of protein function: enzyme evolution by random recombination of improved sequences" 1997, *Journal of Molecular Biology*, 272(3):336-347.
Muilu et al., "Functional conformational changes of endo-1,4-xylanase II from *Trichoderma reesei*: A molecular dynamics study", 1998, *Proteins: Structure, Function, and Genetics*, 31(4):434-444.
Perez-Gonzalez et al., "Molecular Cloning and Expression in *Saccharomyces cerevusiae* of Two *Aspergillus nidulans* Xylanase Genes", 1996, *Applied and Environmental Microbiology*, 62(6):2179-2182.

Sakka et al., "Nucleotide Sequence of the *Clostridium stercorarium* xynA Gene Encoding Xylanase A : Identification of Catalytic and Cellulose Binding Domains", 1993, *Bioscience, Biotechnology, and Biochemistry*, 57(2):273-277.
Sapag et al. "The endoxylanases from family 11: Computer analysis of protein sequences reveals important structural and phylogenetic relationships", May 9, 2002, *Journal of Biotechnology*, 95(2):109-131.
Simpson et al., "An extremely thermostable xylanase from the thermophilic eubacterium *Thermotoga*", 1991, *The Biochemistry Jouornal*, 277:413-417.
Sung et al., "Expression of *Trichoderma reesei* and *Trichoderma viride* xylanases in *Escherichia coli*", 1995, *Biochemistry and Cell Biology*, 73:253-259.
Sung et al., "Overexpression of the *Bacillus subtilis* and circulans Xylanases in *Escherichia coli*", 1993, *Protein Expression and Purification*, 4:200-206.
Sung et al., "Short synthetic oligodeoxyribonucleotide leader sequences enhance accumulation of human proinsulin synthesized in *Escherichia coli*.", 1986, *Proceedings of the National Academy of Sciences of the United States of America*, 83:561-565.
Sunna et al., "Xylanolytic Enzymes from Fungi and Bacteria", 1997, *Critical Reviews in Biotechnology*, 17(1): 39-67.
Torronen et al., "Structural Comparison of Two Major endo-1,4-Xylanases from *Trichoderma reesei*", 1995, *Biochemistry*, 34(3):847-856.
Winterrhalter et al., "Two Extremely Thermostable Xylanases of the Hyperthermophilic Bacterium *Thermotoga maritima* MSB8", 1995, *Applied and Environmental Microbiology*, 61(5):1810-1815.
Yoshino et al. GenBank Accession No. Q12579, Nov. 1, 1996.
Zappe et al., "Cloning and expression of a xylanase gene from *Clostridium acetobutylicum* P262 in *Escherichia coli*", 1987, *Applied Microbiology and Biotechnology*, 27:57-63.
Zappe et al., "Nucleotide sequence of a *Clostridium acetobutylicum* P262 xylanase gene (xynB)", 1990, *Nucleic Acids Research*, 18(8):2179.
Sequence alignment of three pages cited in related U.S. Appl. No. 09/990,874, now as US Patent No. 7,510,860, 2003.
Fisk et al., "Development of a Method for the Stabilization and Formulation of Xylanase from *Trichoderma* Using Experimental Design", *Stability and Stabilization of Enzymes*, Proceeding of an International Symposium held in Maastricht, The Netherlands, Nov. 22-25, 1992, pp. 323-328.
Misset "Stability of Industrial Enzymes", *Stability and Stabilization of Enzymes*, Proceeding of an International Symposium held in Maastricht, The Netherlands, Nov. 22-25, 1992, pp. 111-131.
Nissen et al., "Xylanases for the Pulp and Paper Industry", *Xylans and Xylanases*, 1992 Elservier Science Publishers B.V. pp. 325-337.
Kim et al., "Directed Evolution of Thermus Maltogenic Amylase toward Enhanced Thermal Resistance", *applied and Environmental Microbiology*, Aug. 2003, 69(8):4866-4874.
Xiong et al., "Directed Evolution of Beta-galactosidase from *Escherichia coli* into Beta-glucuronidase" *Journal of Biochemistry and Molecular Biology*, May 2007, 40(3):419-425.
Chica et al., "Semi-rational approaches to engineering enzyme activity: combining the benefits of directed evolution and rational design" *Current opinion in Biotechnology*, 2005, 16:378-384.
Essential Documents of Opposition History Related to European Opposition of EP 111447 B1, Aug. 2007-Sep. 2011.
Moreaua et al., "Increase in catalytic activity and thermostability of the xylanase A of *Streptomyces lividans* 1326 by site-specific mutagenesis", *Enzyme and microbial technology*, 1994, 16(5):420-424, Abstract only.
Davies et al., "Structures and mechanisms of glycosyl hydrolases." *Structure*, 1995, 3:853-859.
Dombrowski et al., "Disulfide by Design: a computational method for the rational design of disulfide bonds in proteins" *Bioinformatics* 2003,19:1852-1853.
Ferre et al., "DIANNA: a web server for disulfide connectivity prediction." *Nucl. Acids. Res.* 2005, vol. 33, web server issue, doi:10.1093Inarlgki412.
Hazes et al., "Model building of disulfide bonds in proteins with known three dimensional structure." *Prot. Eng.*, 1988, 2:119-125.

(56) References Cited

OTHER PUBLICATIONS

Lagrange et al., "Expression of *Trichoderma reesei* beta-xylanase gene (xyn2) in *Saccharomyces cerevisiae*", *Appl. Environ. Microbial.* 1996, 62:1036-1044.

Lambert et al "ESyPred3D Prediction of proteins 3-D structures." *Bioinformatics*, 2002, 18:1250-1256.

Petersen et al., "Amino acid neighbors and detailed conformational analysis of cysteines in proteins." *Prot. Eng.* 1999, 12:535-548.

O'Connor et al., "GDAP: a web tool for genome-wide protein disulfide bond prediction." *Nucl. Acids Res.* 2004, 32, Web server issue.

Scopes et al., "Protein Purification: principles and Practice", 2nd Edition, 1987, Springer-Verlag, New York, pp. 249-252.

Yang et al., "Hyperexpression of a *Bacillus ciruclans* xylanase gene in *Escherichia coli* and characterization of the gene product."*Appl. Environ. Micrbio.* 1989, 55:1192-1195.

Liu et al. "Expression of recombinant *Aspergillus niger* xylanase A in *Pichia pastoris* and its action on xylan" *Protein expression and Purification*, 2006, 48:292-299.

Ay et al., "Structure and function of the *Bacillus* hybrid enzyme GluXyn-1: Native-like jellyroll fold preserved after insertion of autonomous globular domain", *Proc. Natl. Acad. Sci.* USA, 1998, 95:6613-6618.

Homology matrix, cited in Opposition History of EP Patent No. 1131447, Sep. 2009.

Alignment of family 11 xylanase amino acid sequences, cited in Opposition History of EP Patent No. 1131447, Sep. 2009.

Structural overlays of the 3-D structures of the family 11 xylanases from *A. niger* D20 (UKR), hybrid D22 (AKX) and *B. circulans* variant D 19 and D23 (XNC), cited in Opposition History of EP Patent No. 1131447, Sep. 2009.

Chen et al., "Directed evolution to produce an alkalophilic variant from a *Neocallimastix patriciarum* x ylanase", *Canadian Journal of Microbiology*; Dec. 2001; 47:1088-1094 (2001).

\* cited by examiner

```
Ca    1                                                     S  AFNTQAAP    9
Cs    1                                                        G           1

Tr2#                  10         20         30         40
                       |          |          |          |
Bp    1    RTITNNEMGN  HSGYDYELWK  DYGNT-SMTL  NNGGAFSAGW  N--NIGNA   45
Ca   10    KTITSNEIGV  NGGYDYELWK  DYGNT-SMTL  KNGGAFSCQW  S--NIGNA   54
Fs    1      NSSVTGNVG  SSPYHYEIWY  QGG-NNSMTF  YDNGTYKASW  N--GTNDF   44
Cs    2    RIIYDNETGT  HGGYDYELWK  DYGNT-IMEL  NDGGTFSCQW  S--NIGNA   46
Rf    1    SAADQQTRGN  VGGYDYEMWN  QNGQGQASMN  PGAGSFTCSW  S--NIENF   46
Tr2   1    QTIQPGTGY   NNGYFYSYWN  DGHGGVTYTN  GPGGQFSVNW  S--NSGNF   45
Tv    1    QTIGPGTGF   NNGYFYSYWN  DGHGGVTYTN  GPGGQFSVNW  S--NSGNF   45
Th    1    QTIGPGTGY   SNGYYYSYWN  DGHAGVTYTN  GGGGSFTVNW  S--NSGNF   45
Sc    1    SGTPSSTGT   DGGYYYSWWT  DGAGDATYQN  NGGGSYTLTW  SG-NNGNL   46
An    1            S   AGINYVQNYN  GNLGDFTY-D  ESAGTFSMYW  EDGVSSDF   38
Ak    1            S   AGINYVQNYN  GNLADFTY-D  ESAGTFSMYW  EDGVSSDF   38
At    1            S   AGINYVQNYN  GNLGDFTY-D  ESAGTFSMYW  EDGVSSDF   38
Tr1   1             ASINYDQNYQ    TGG-QVSYS-  PSNTGFSVNW  N--TQDDF   34
Aa    1    RSTPSSTGE   NNGYYYSFWT  DGGGDVTYTN  GNAGSYSVEW  S--NVGNF   45
Ss    1 ATTIT-NETGY    D-GMYYSFWT  DGGGSVSMTL  NGGGSYSTRW  T--NCGNF   45
SlB   1 DTVVTTNQEGT    NNGYYYSFWT  DSQGTVSMNM  GSGGQYSTSW  R--NTGNF   47
SlC   1 ATTITTNQTGT    D-GMYYSFWT  DGGGSVSMTL  NGGGSYSTQW  T--NCGNF   46
Tl    1    QTTPNSEGW   HDGYYYSWWS  DGGAQATYTN  LEGGTYEISW  G--DGGNL   45
Tf    1    AVTSNETGY   HDGYFYSFWT  DAPGTVSMEL  GPGGNYSTSW  R--NTGNF   45
Bc    1            ASTDYWQNWT     DGGGIVNAVN  GSGGNYSVNW  S--NTGNF   36
Bs    1            ASTDYWQNWT     DGGGIVNAVN  GSGGNYSVNW  S--NTGNF   36
```

FIGURE 1

```
Tr2#              50              60              70              80
                   |               |               |               |
Bp   46  LFRK-GKKFD ST-RTHHQLG NISINYNASF N-PGGNSYLC VYGWTQSP  90
Ca   55  LFRK-GKKFN DT-QTYKQLG NISVNYNCNY Q-PYGNSYLC VYGWTSSP  99
Fs   45  LARV-GFKYD EK-HTYEELGPIDAYYKWSKQ GSAGGYNYIG IYGWTVDP  91
Cs   47  LFRK-GRKFN SD-KTYQELG DIVVEYGCDY N-PNGNSYLC VYGWTRNP  91
Rf   47  LARM-GKNYD SQKKNYKAFG NIVLTYDVEY T-PRGNSYMC VYGWTRNP  92
Tr2  46  VGGK-GWQPG TKNKV----- ---INFS-GS YNPNGNSYLS VYGWSRNP  83
Tv   46  VGGK-GWQPG TKNKV----- ---INFS-GT YNPNGNSYLS VYGWSRNP  83
Th   46  VGGK-GWQPG TKNKV----- ---INFS-GS YNPNGNSYLS IYGWSRNP  83
Sc   47  VGGK-GWNPG AASRS----- ---ISYS-GT YQPNGNSYLS VYGWTRSS  84
An   39  VVGL-GWTTG SSNA------ ---ITYSAEY SASGSSSYLA VYGWVNYP  76
Ak   39  VVGL-GWTTG SSNA------ ---ISYSAEY SASGSSSYLA VYGWVNYP  76
At   39  VVGL-GWTTG SSNA------ ---ITYSAEY SASGSASYLA VYGWVNYP  76
Tr1  35  VVGV-GWTTG SSAP------ ---INFGGSF SVNSGTGLLS VYGWSTNP  72
Aa   46  VGGK-GWNPG SAKD------ ---ITYSGNF T-PSGNGYLS VYGWTTDP  82
Ss   46  VAGK-GWANG GR-RT----- ---VRYT-GW FNPSGNGYGC LYGWTSNP  82
SlB  48  VAGK-GWANG GR-RT----- ---VQYS-GS FNPSGNAYLA LYGWTSNP  84
SlC  47  VAGK-GWSTG DGN------- ---VRYN-GY FNPVGNGYGC LYGWTSNP  82
Tl   46  VGGK-GWNPG LNARA----- ---IHFE-GV YQPNGNSYLA VYGWTRNP  83
Tf   46  VAGK-GWATG GR-RT----- ---VTYS-AS FNPSGNAYLT LYGWTRNP  82
Bc   37  VVGK-GWTTG SPFRT----- ---INYNAGV WAPNGNGYLT LYGWTRSP  75
Bs   37  VVGK-GWTTG SPFRT----- ---INYNAGV WAPNGNGYLT LYGWTRSP  75

Tr2#              90             100             110             120             130
                   |               |               |               |               |
                                   *|                               *|
Bp   91  LAEYYIVDSW GTYR-PT--G AYKGSFYADG GTYDIYETTR VNQPSIIG 135
Ca  100  LVEYYIVDSW GSWRPP--GG TSKGTITVDG GIYDIYETTR INQPSIQG 145
Fs   92  LVEYYIVDDW FNKPGANLLG QRKGEFTVDG DTYEIWQNTR VQQPSIKG 139
Cs   92  LVEYYIVESW GSWRPP--GA TPKGTITQWMAGTYEIYETTR VNQPSIDG 138
Rf   93  LMEYYIVEGW GDWRPPGNDG EVKGTVSANG NTYDIRKTMR YNQPSLDG 140
Tr2  84  LIEYYIVENF GTYN-PSTGA TKLGEVTSDG SVYDIYRTQR VNQPSIIG 130
Tv   84  LIEYYIVENF GTYN-PSTGA TKLGEVTSDG SVYDIYRTQR VNQPSIIG 130
Th   84  LIEYYIVENF GTYN-PSTGA TKLGEVTSDG SVYDIYRTQR VNQPSIIG 130
Sc   85  LIEYYIVESY GSYD-PSSAA SHKGSVTCNG ATYDILSTWR YNAPSIDG 131
An   77  GAEYYIVEDY GDYN-PCSSA TSLGTVYSDG STYQVCTDTR INEPSITG 123
Ak   77  QAEYYIVEDY GDYN-PCSSA TSLGTVYSDG STYQVCTDTR TNEPSITG 123
At   77  QAEYYIVEDY GDYN-PCSSA TSLGTVYSDG STYQVCTDTR TNEPSITG 123
Tr1  73  LVEYYIMEDN HNY--PAQ-G TVKGTVTSDG ATYTIWENTR VNEPSIQG 117
Aa   83  LIEYYIVESY GDYN-PGSGG TTRGNVSSDG SVYDIYTATR TNAPSIQG 129
Ss   83  LVEYYIVDNW GSYR-PT--G ETRGTVHSDG GTYDIYKTTR YNAPSVEA 127
SlB  85  LVEYYIVDNW GTYR-PT--G EYKGTVTSDG GTYDIYKTTR VNKPSVEG 129
SlC  83  LVEYYIVDNW GSYR-PT--G TYKGTVSSDG GTYDIYQTTR YNAPSVEG 127
Tl   84  LVEYYIVENF GTYD-PSSGA TDLGTVECDG SIYRLGKTTR VNAPSIDG 130
Tf   83  LVEYYIVESW GTYR-PT--G TYMGTVTTDG GTYDIYKTTR YNAPSIEG 127
Bc   76  LIEYYVVDSW GTYR-PT--G TYKGTVKSDG GTYDIYTTTR YNAPSIDG 120
Bs   76  LIEYYVVDSW GTYR-PT--G TYKGTVKSDG GTYDIYTTTR YNAPSIDG 120
```

FIGURE 1 CONT'D

```
      Tr2#              140          150          160
Bp  136  -IATFKQYWS  VRQTKRTS--  ------GTVS  VSAHFRKWES  LGMPM-GK   173
Ca  146  -NTTFKQYWS  VRRTKRTS--  ------GTIS  VSKHFAAWES  KGMPL-GK   183
Fs  140  -TQTFPQYFS  VRKSARSC--  ------GHID  ITAHMKKWEE  LGMKM-GK   177
Cs  139  -TATFQQYWS  VRTSKRTS--  ------GTIS  VTEHFKQWER  MGMRM-GK   176
Rf  141  -TATFPQYWS  VRQTSGSANN  QTNYMKGTID  VTKHFDAWSA  AGLDMSGT   187
Tr2 131  -TATFYQYWS  VRRNHR-S-S  ------GSVN  TANHFNAWAQ  QGLTL-GT   168
Tv  131  -TSTFYQYWS  VRRTHR-S-S  ------GSVN  TANHFNAWAQ  QGLTL-GT   168
Th  131  -TATFYQYWS  VRRNHR-S-S  ------GSVN  TANHFNAWAS  HGLTL-GT   168
Sc  132  -TQTFEQFWS  VRNPKKAPGG  SIS---GTVD  VQCHFDAWKG  LGMNLGSE   175
An  124  -TSTFTQYFS  VRESTRTS--  ------GTVT  VANHFNFWAQ  HGFGN-SD   161
Ak  124  -TSTFTQYFS  VRESTRTS--  ------GTVT  VANHFNFWAQ  HGFGN-SD   161
At  124  -TSTFTQYFS  VRESTRTS--  ------GTVT  VANHFNFWAH  HGFGN-SD   161
Tr1 118  -TATFNQYIS  VRNSPR-T-S  ------GTVT  VQNHFNAWAS  LGLHLGQM   156
Aa  130  -TATFSQYWS  VRQNKR-VG-  ------GTVT  TSNHFNAWAK  LGMNL-GT   167
Ss  128  -PAAFDQYWS  VRQSKVT--S  ------GTIT  TGNHFDAWAR  AGMNMGNF   166
SlB 130  TR-TFDQYWS  VRQSKR-TG-  ------GTIT  TGNHFDAWAR  AGMPLGNF   168
SlC 128  TK-TFQQYWS  VRQSKVTSGS  ------GTIT  TGNHFDAWAR  AGMNMGQF   168
Tl  131  TQ-TFDQYWS  VRQDKR-T-S  ------GTVQ  TGCHFDAWAR  AGLNVNGD   169
Tf  128  TR-TFDQYWS  VRQSKRTS--  ------GTIT  AGNHFDAWAR  HGMHLGTH   166
Bc  121  DRTTFTQYWS  VRQSKRPTGS  N-----ATIT  FTNHVNAWKS  HGMNLGSN   163
Bs  121  DRTTFTQYWS  VRQSKRPTGS  N-----ATIT  FSNHVNAWKS  HGMNLGSN   163

Tr2#          170         180         190
Bp  174  MYETAFTVEG  YQSSGSANVM  TNQLFIGN       201
Ca  184  MHETAFNIEG  YQSSGKADVN  SMSINIGK       211
Fs  178  MYEAKVLVEA  GGGSGSFDV-  TYFKMT         202
Cs  177  MYEVALTVEG  YQSSGYANVY  KNEIRIGANP     206
Rf  188  LYEVSLNIEG  YRSNGSANVK  SVSV           211
Tr2 169  MDYQIVAVEG  YFSSGSASI-  TVS            190
Tv  169  MDYQIVAVEG  YFSSGSASI-  TVS            190
Th  169  MDYQIVAVEG  YFSSGSASI-  TVS            190
Sc  176  HNYQIVATEG  YQSSGTATI-  TVT            197
An  162  FNYQVMAVEA  WSGAGSASV-  TISS           184
Ak  162  FNYQVMAVEA  WSGAGSASV-  TISS           184
At  162  FNYQVVAVEA  WSGAGSASV-  TISS           184
Tr1 157  -NYQVVAVEG  WGGSGSASQ-  SVSN           178
Aa  168  HNYQILATEG  YQSSGSSSI-  TIQ            189
Ss  167  RYYMINATEG  YQSSGSSTI-  TVSG           189
SlB 169  SYYMIMATEG  YQSSGSSSI-  NVGG           191
SlC 169  RYYMIMATEG  YQSSGSSNI-  TVSG           191
Tl  170  HYYQIVATEG  YFSSGYARI-  TVADVG         194
Tf  167  D-YMIMATEG  YQSSGSSNVT  LGTS           189
Bc  164  WAYQVMATEG  YQSSGSSNV-  TVW            185
Bs  164  WAYQVMATEG  YQSSGSSNV-  TVW            185
```

FIGURE 1 CONT'D

| | | |
|---|---|---|
| Bp | *Bacillus pumilus* | (SEQ ID NO: 4) |
| Ca | *Clostridium acetobutylicum* P262 Xyn B | (SEQ ID NO: 6) |
| Cs | *Clostridium stercorarium* Xyn A | (SEQ ID NO: 7) |
| Rf | *Ruminococcus flavefaciens* | (SEQ ID NO: 8) |
| Tr2 | *Trichoderma reesei* Xyn II | (SEQ ID NO: 16) |
| Tv | *Trichoderma viride* | (SEQ ID NO: 17) |
| Th | *Trichoderma harzianum* | (SEQ ID NO: 14) |
| Sc | *Schizophyllum commune* Xyn A | (SEQ ID NO: 9) |
| An | *Aspergillus niger*, var. *awamori* | (SEQ ID NO: 1) |
| Ak | *Aspergillus kawachii* Xyn C | (SEQ ID NO: 21) |
| At | *Aspergillus tubingensis* | (SEQ ID NO: 2) |
| Tr1 | *Trichoderma reesei* Xyn I | (SEQ ID NO: 15) |
| Aa | *Aspergillus awamori var.kawachi* Xyn B | (SEQ ID NO: 19) |
| Fs | *Fibrobacter succinogenes* Xyn II | (SEQ ID NO: 18) |
| Ss | *Streptomyces* sp. 36a | (SEQ ID NO: 12) |
| SlB | *Streptomyces lividans* Xyn B | (SEQ ID NO: 10) |
| SlC | *Streptomyces lividans* Xyn C | (SEQ ID NO: 11) |
| Tl | *Thermomyces lanuginosus* Xyn | (SEQ ID NO: 20) |
| Tf | *Thermomonospora fusca* TfxA | (SEQ ID NO: 13) |
| Bc | *Bacillus circulans* | (SEQ ID NO: 3) |
| Bs | *Bacillus subtilis* | (SEQ ID NO: 5) |

FIGURE 1 CONT'D

```
                                            |                              st
(SEQ ID NO:61)  5'-CT AGC TAA GGA GG CTG CAG ATG
(SEQ ID NO:62)            G ATT CCT CC GAC GTC TAC
                       NheI |                PstI
```

```
                              TrX-1
  1   2   3   4   5   6   7   8   9  10  11  12  13  14  15  16
  Q   T   I   Q   P   G   T   G   Y   N   N   G   Y   F   Y   S
 CAA ACA ATA CAA CCA GGA ACC GGT TAC AAC AAC GGT TAC TTT TAC AGC
 GTT TGT TAT GTT GGT CCT TGG CCA ATG TTG TTG CCA ATG AAA ATG TCG
              TrX-8           AgeI                  |
```

```
          |                   XyTv-2
 17  18  19  20  21  22  23  24  25  26  27  28  29  30  31  32
  Y   W   N   D   G   H   G   G   V   T   Y   T   N   G   P   G
 TAT TGG AAC GAT GGC CAT GGT GGT GTT ACC TAT ACA AAC GGG CCC GGA
 ATA ACC TTG CTA CCG GTA CCA CCA CAA TGG ATA TGT TTG CCC GGG CCT
                      NcoI                       XyTv-7    ApaI
```

```
                                                            |
 33  34  35  36  37  38  39  40  41  42  43  44  45  46  47  48
  G   Q   F   S   V   N   W   S   N   S   G   N   F   V   G   G
 GGC CAA TTT AGC GTC AAT TGG TCT AAC TCC GGA AAC TTC GTA GGT GGA
 CCG GTT AAA TCG CAG TTA ACC AGA TTG AGG CCT TTG AAG CAT CCA CCT
                      MunI   |          BspEI
```

```
                        TrX-3
 49  50  51  52  53  54  55  56  57  58  59  60  61  62  63  64
  K   G   W   Q   P   G   T   K   N   K   V   I   N   F   S   G
 AAA GGT TGG CAA CCC GGG ACC AAA AAT AAG GTG ATC AAC TTC TCT GGA
 TTT CCA ACC GTT GGG CCC TGG TTT TTA TTC CAC TAG TTG AAG AGA CCT
                      XmaI                      TrX-6
```

```
                      |
 65  66  67  68  69  70  71  72  73  74  75  76  77  78  79  80
  S   Y   N   P   N   G   N   S   Y   L   S   V   Y   G   W   S
 TCT TAT AAT CCG AAT GGG AAT TCA TAC TTA AGC GTC TAT GGC TGG TCT
 AGA ATA TTA GGC TTA CCC TTA AGT ATG AAT TCG CAG ATA CCG ACC AGA
  |                         EcoRI      AflII
```

```
   XyTv-4                                                    |
 81  82  83  84  85  86  87  88  89  90  91  92  93  94  95
  R   N   P   L   I   E   Y   Y   I   V   E   N   F   G   T
 AGA AAC CCA CTG ATT GAA TAT TAC ATT GTC GAA AAT TTC GGT AC
 TCT TTG GGT GAC TAA CTT ATA ATG TAA CAG CTT TTA AAG C
 Xba I           XyTv-5                                 |  KpnI
```

Figure 2

```
                                          XyTv-101
         92  93  94  95  96  97  98  99 100 101 102 103 104 105
     V   D   N   F   G   T   Y   N   P   S   T   G   A   T   K   L
    TC  GAC AAT TTC GGT ACC TAC AAT CCG AGT ACC GGC GCC ACA AAA TTA
    3'-G    TTA AAG CCA TGG ATG TTA GGC TCA TGG CCG CGG TGT TTT AAT
    SalI             KpnI            XyTv-110   KasI/NarI 106 107 108 109 110 111 112 113 114 115 116 117 118 119 120 121
     G   E   V   T   S   D   G   S   V   Y   D   I   Y   R   T   Q
    GGC GAA GTC ACT AGT GAT GGA TCC GTA TAT GAT ATC TAC CGT ACC CAA
    CCG CTT CAG TGA TCA CTA CCT AGG CAT ATA CTA TAG ATG GCA TGG GTT
                SpeI        BamHI                          XyTv-109

TrX-103
   122 123 124 125 126 127 128 129 130 131 132 133 134 135 136 137
     R   V   N   Q   P   S   I   I   G   T   A   T   F   Y   Q   Y
    CGC GTT AAT CAG CCA TCG ATC ATT GGA ACC GCC ACC TTT TAT CAG TAC
    GCG CAA TTA GTC GGT AGC TAG TAA CCT TGG CGG TGG AAA ATA GTC ATG
    MluI             ClaI 138 139 140 141 142 143 144 145 146 147 148 149 150 151 152 153
     W   S   V   R   R   N   H   R   S   S   G   S   V   N   T   A
    TGG AGT GTT AGA CGT AAT CAT CGG AGC TCC GGT TCG GTT AAT ACT GCG
    ACC TCA CAA TCT GCA TTA GTA GCC TCG AGG CCA AGC AAT TGA CGC
    TrX-108                             SacI

XyTv-104
   154 155 156 157 158 159 160 161 162 163 164 165 166 167 168 169
     N   H   F   N   A   W   A   Q   Q   G   L   T   L   G   T   M
    AAT CAC TTT AAT GCA TGG GCA CAG CAA GGG TTA ACC CTA GGT ACA ATG
    TTA GTG AAA TTA CGT ACC CGT GTC GTT CCC AAT TGG GAT CCA TGT TAC
                    NsiI     XyTv-107                AvrII

XyTv-105
   170 171 172 173 174 175 176 177 178 179 180 181 182 183 184 185
     D   Y   Q   I   V   A   V   E   G   Y   F   S   S   G   S   A
    GAT TAT CAA ATC GTA GCG GTG GAA GGC TAC TTC TCG AGT GGT TCC GCT
    CTA ATA GTT TAG CAT CGC CAC CTT CCG ATG AAG AGC TCA CCA AGG CGA
                            XyTv-106              XhoI 186 187 188 189 190
     S   I   T   V   S      (SEQ ID NO:40)
    AGT ATT ACA GTG AGC TAA A     (SEQ ID NO:63)
    TCA TAA TGT CAC TCG ATT TCT AG-5'  (SEQ ID NO:64)
                            BglII
```

MODIFICATION OF XYLANASES TO INCREASE THERMOPHILICITY, THERMOSTABILITY AND ALKALOPHILICITY

CROSS REFERENCE TO RELATED APPLICATIONS

This application is a continuation of international application PCT/CA2007/000590, filed Apr. 10, 2007, which claims priority to U.S. Provisional Application Ser. No. 60/791,541, filed Apr. 12, 2006, and international application PCT/CA2006/001192, filed Jul. 19, 2006, each of which are herein incorporated by reference in their entireties for all purposes.

FIELD

The present invention relates to the modification of xylanases. More specifically, the invention relates to modified xylanases that can perform at high temperature and pH.

BACKGROUND OF THE INVENTION

Xylanases are a group of enzymes with wide commercial utility. Major applications of xylanases include pulp biobleaching in the production of paper, clarifying agents in juices and wines, as a supplement to improve digestibility of poultry and swine feed and as a washing agent of precision devices and semiconductors (e.g. U.S. Pat. No. 5,078,802).

In the manufacturing of pulp for the production of paper, fibrous material is subjected to high temperatures and pressures in the presence of chemicals. This treatment converts the fibers to pulp and is known as pulping. Following pulping, the pulp is bleached. Xylanase enzymes are used to enhance the bleaching of the pulp. The xylanase treatment allows subsequent bleaching chemicals such as chlorine, chlorine dioxide, hydrogen peroxide, or combinations of these chemicals, to bleach pulp more efficiently. Pretreatment of pulp with xylanase increases the whiteness and quality of the final paper product and reduces the amount of bleaching chemicals which must be used to bleach the pulp. This, in turn, decreases the amount of bleaching chemicals present in the effluent produced by such processes.

The most important chemical pulping process is the production of kraft pulp. For kraft pulp, following pulping, and prior to the treatment of pulp with xylanase, the pulp is exposed to a temperature of 55-70° C. and a highly alkaline pH (e.g. Nissen et al., 1992). A drawback of many commercially available wild-type xylanases is that these enzymes exhibit an acidic pH optimum and a temperature optimum of about 55° C. Therefore, in order to utilize xylanases effectively for bleaching applications, the pulp must be acidified to a pH approximating the optimal pH for the specific xylanase used. In addition, the hot pulp must be cooled to a temperature close to the optimal temperature for enzymatic activity of the selected xylanase. Decreasing pulp temperatures for xylanase treatment decreases the efficiency of the subsequent chemical bleaching. Acidification of pulp requires the use of large quantities of acids. Furthermore, the addition of acids leads to corrosion and lessens the lifetime of process equipment. Thus, xylanases optimally active at temperatures and pH conditions approximating the conditions of the pulp would be useful and beneficial in pulp manufacturing.

Xylanases which exhibit greater activity at higher temperatures could be used to treat pulp immediately following the pulping process, without the need to cool the pulp. Similarly, xylanases which exhibit greater activity at higher pH conditions would require less or no acid to neutralize the pulp. Xylanases with such properties would provide several advantages and substantial economic benefits within a variety of industrial processes.

Several approaches directed towards improving xylanase for use in pulp bleaching within the prior art include the isolation of thermostable xylanases from extreme thermophiles that grow at 80-100° C., such as *Caldocellum saccharolyticum*, *Thermatoga maritima* and *Thermatoga* sp. Strain FJSS-B.1 (Lüthi et al., 1990; Winterhalter et al., 1995; and Simpson et al., 1991). However, these thermostable xylanase enzymes are large, with molecular masses ranging from 35-120 kDa (320-1100 residues), and have a reduced ability to penetrate the pulp mass compared with other smaller xylanases which exhibit better accessibility to pulp fibers. In addition, some of the extremely thermophilic xylanases, such as *Caldocellum saccharolyticum* xylanase A, exhibit both xylanase and cellulase activities (Lüthi et al., 1990). This additional cellulolytic activity is undesirable for pulp bleaching due to its detrimental effect on cellulose, the bulk material in paper. Furthermore, hyper-thermostable xylanase enzymes, which function normally at extremely high temperatures, have low specific activities at temperatures in the range for optimal pulp bleaching (Simpson et al., 1991).

A number of xylanases have been modified by protein engineering to improve their properties for industrial applications. For instance, U.S. Pat. No. 5,405,769 (Campbell et al.) discloses the modification of *Bacillus circulans* xylanase (BcX) using site-directed mutagenesis to improve the thermostability of the enzyme. The site specific mutations include replacing two amino acids with cysteine residues to create intramolecular disulfide bonds. The mutations to create disulfide bonds include S179C (i.e., serine at position 179 replaced with cysteine) for an intermolecular crosslink between two xylanase molecules, and S100C/N148C and V98C/A152C for the creation of intramolecular crosslinks. These disulfide linkages contribute to the thermostability of the enzyme, and do not effect the thermophilicity or alkalophilicity of the enzyme. WO 00/29587 (Sung and Tolan) discloses the formation of the disulfide crosslinks, 110/154 and 108/158, in the fungal xylanase of *Trichoderma reesei* xylanase II (TrX or TrX II), corresponding to the 100/148 and 98/152 disulfide bonds of the BcX. As in the case of BcX, these crosslinks also increased the thermostability of TrX II, but do not have an effect on the thermophilicity or alkalophilicity of the enzyme.

U.S. Pat. No. 5,405,769 (supra) also discloses the mutation of specific residues in the N-terminus of the xylanase and these mutations were found to further improve the thermostability of the enzyme. In in vitro assays, the disulfide mutants showed thermostability at 62° C., an improvement of 7° C. over the native BcX xylanase enzyme. However, these thermostable disulfide mutants showed no gain in thermophilicity (Wakarchuck et al., 1994). Mutations T3G, (BcX xylanase amino acid numbering) D4Y(F) and N8Y(F), near the N-terminus of the BcX xylanase enzyme, provided thermostability to 57° C., an increase of 2° C. over the native BcX (U.S. Pat. No. 5,405,769). However, the use of these enzymes in industrial applications still requires cooling and acidification of pulp following pretreatment prior to enzyme addition. Therefore, further increases in thermostability, thermophilicity and pH optima are still required.

It is known in the art to modify *Trichoderma reesei* xylanase II (TrX II or TrX) to increase thermophilicity and alkalophilicity. For instance, U.S. Pat. No. 5,759,840 (Sung et al.) and U.S. Pat. No. 5,866,408 (Sung et al.) disclose mutations in the N-terminal region (residues 1-29) of TrX. Three mutations, at residues 10, 27 and 29 of TrX, were found to increase the enzymatic activity of the xylanase enzyme at elevated temperatures and alkaline pH conditions.

WO 01/92487 (Sung) discloses mutations S75A, L105R, N125A, I129E of TrX II, to produce a xylanase which maintains greater activity at higher temperature and pH. WO 03/046169 (Sung) also describes the application of multiple mutations to arginine residues (Y135R, H144R, Q161R) in order to increase the pH optimum of the TrX II. The mutation, Y118C, allowed the xylanase to maintain its optimal activity at higher temperature.

Turunen et al. (2002) describe the use of specific multiple arginines on the specific "Ser/Thr surface" of TrX II to increase the enzymatic activity at higher temperatures, but with decreased thermostability. It was also reported that another mutation, K58R, displayed slightly increased thermostability. However, this mutation in combination with other arginines showed a narrower range of effective pH.

Turunen et al. (2001) disclose mutations N11D, N38E, Q162H of TrX II with a complement of similar disulfide bonds (S110C/N154C) to improve the thermostability of the xylanase. However, these mutations, including N11D, also have an adverse effect on both the thermophilicity and the alkalophilicity of the xylanase, resulting in a decrease of enzymatic activity at higher temperatures and neutral-alkaline pH as compared to native TrX II.

There have been many attempts to stabilize proteins via the introduction of engineered disulfide bonds, with mixed results. Sowdhamini et al. (1989) describes a computational procedure called MODIP (Modeling of Disulfide bridges in Proteins) to aid in the design of proteins with disulfide bridges. By this method, a large number of sites for potential disulfide bond formation are usually predicted, with no way to foretell which are most likely to stabilize the protein. Dani et al. (2003) describe a refined version of this method to assist such selection. It predicted that a crucial requirement in any stabilizing disulfide bond is to enclose a loop of more than 25 amino acid residues between the two cysteines. A loop with less than 25 residues will offer little stabilization.

WO 00/29587 (Sung and Tolan) report the formation of two disulfide bonds in *Trichoderma reesei* xylanase II, one linking positions 110 and 154, and another linking positions 108 and 158 (both enclosed loops longer than 25 residues). Both disulfide bonds provide for enhanced thermostability of the enzyme, but do not enhance the thermophilicity.

Fenel et al. (2004) describe the formation of a disulfide bridge in TrX II through two mutations, T2C and T28C, which results in an increase in the temperature optimum and the thermostability of the enzyme without any change in the pH-dependent activity. The disulfide crosslink encloses a loop having a length of 26 amino acid residues between the two cysteine residues.

While the prior art discloses the modification of xylanases to alter various characteristics, the needs of current industrial processes require enzymes with increasingly robust activity. There is a need in the art for novel xylanases which exhibit increased enzymatic activity at elevated temperatures and pH conditions. Such enzymes would be adaptable to uses in various fields, for example the production of paper pulp and the washing of precision devices and semiconductors.

DESCRIPTION OF THE TEXT FILE SUBMITTED ELECTRONICALLY

The contents of the text file submitted electronically are incorporated herein by reference in their entirety: A computer readable format copy of the Sequence Listing (filename: GOWL-019-01US.txt, date recorded: May 27, 2011, file size 86 kilobyte).

SUMMARY OF THE INVENTION

The present invention relates to modified xylanases. More specifically, the invention relates to modified xylanases with improved performance at conditions of high temperature and/or pH.

This invention relates to a modified xylanase comprising cysteine residues at positions 99 and 118 to form an intramolecular disulfide bond, the xylanase produced by substitution of an amino acid at positions 99, 118 or both positions 99 and 118 with a cysteine. The positions of the amino acid substitution(s) are determined from sequence alignment of the modified xylanase with a *Trichoderma reesei* xylanase II amino acid sequence as defined in SEQ ID NO:16. The modified xylanase exhibits thermophilicity, alkalophilicity, thermostability or a combination thereof.

The modified xylanase may be derived from a Family 11 xylanase, including, but not limited to, a *Trichoderma reesei* xylanase. The modified xylanase is preferably not a native *Aspergillus* xylanase.

According to the present invention, there is also provided a modified xylanase, as described above, further comprising a substituted amino acid residue at position 40. The substituted amino acid at position 40 may be selected from the group consisting of His, Cys, Phe, Lys, Tyr and Arg. In a specific example, the substituted amino acid at position 40 is a basic amino acid, including, but not limited to, His.

The present invention also pertains to the modified xylanase comprising cysteine residues at positions 99 and 118 and further comprising a substituted amino acid at position 58, including, but not limited to, a basic amino acid, such as Arg. In addition, the modified xylanase just described may further comprise a basic substituted amino acid at position 10, a hydrophobic substituted amino acid at position 27 and a hydrophobic substituted amino acid at position 29. The basic substituted amino acid at position 10 may be His, the hydrophobic substituted amino acid at position 27 is a Met and the hydrophobic substituted amino acid at position 29 is a Leu (HML). In addition to these mutations, the modified xylanase may comprise a non-polar substituted amino acid at position 75, a basic substituted amino acid at position 105, a non-polar substituted amino acid at position 125 and an acidic amino acid at position 129. The non-polar amino acid at position 75 may be an Ala, the basic amino acid at position 105 may be a His, the non-polar amino acid at position 125 may be an Ala and the acidic amino acid at position 129 may be a Glu. The modified xylanase may further comprise an acidic amino acid at position 11, such as an Asp. In addition to a mutation at position 11, the modified xylanase may further comprise a mutation at position 131 to an Asn.

This invention also includes a modified xylanase comprising cysteine residues at positions 99 and 118 and further comprising basic amino acids at positions 40 and 58. The modified xylanase may further comprise a basic substituted amino acid at position 10, a hydrophobic substituted amino acid at position 27, and a hydrophobic substituted amino acid at position 29. The basic substituted amino acid at position 10 may be His, the hydrophobic substituted amino acid at position 27 may be Met and the hydrophobic substituted amino acid at position 29 may be Leu (HML). In addition to these mutations, the modified xylanase just described may further comprise a non-polar substituted amino acid at position 75, including, but not limited to, Ala; a basic substituted amino acid at position 105, including, but not limited to, His; a non-polar substituted amino acid at position 125, including, but not limited to, Ala; and an acidic amino acid at position 129, including, but not limited to, Glu. The modified xylanase may further comprise an acidic substituted amino acid at position 11, including, but not limited to, Asp; and, optionally, an Asn at position 131. The modified xylanase as just described may further comprise a substituted amino acid at position 52, including, but not limited to, Cys. In addition, the modified xylanase may further comprise basic substituted amino acids at positions 144 and 161, including, but not limited to, Arg residues.

The present invention also relates to a modified xylanase comprising substituted amino acid residues at positions 99 and 118 and having a maximum effective temperature (MET) between about 65° C. and about 85° C. or having a maximum effective pH (MEP) between about pH 6.5 and about pH 8.0.

The present invention also relates to a modified xylanase selected from the group consisting of:

sequence as defined in SEQ ID NO:16. The modified xylanase as just defined may further comprise an intramolecular disulfide bond having a loop of between 10 and 24 amino acids. The intramolecular disulfide bond may be produced by substitution of an amino acid at position 99, 118 or both positions 99 and 118 with a cysteine. The amino acid substitution at position 40 is preferably a basic amino acid, including, but not limited to, His.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows an amino acid sequence alignment among Family 11 xylanases. The amino acid numbering is relative to

| MUTANT | NAME | SEQUENCE |
|---|---|---|
| TrX-99C-118C | TrX-CC | SEQ ID NO:66 |
| TrX-40H-99C-118C | TrX-H CC | SEQ ID NO:67 |
| TrX-58R-99C-118C | TrX-R CC | SEQ ID NO:68 |
| TrX-40H-58R-99C-118C | TrX-HR CC | SEQ ID NO:69 |
| TrX-10H-27M-29L-40R-58R-99C-118C | TrX-HML RR CC | SEQ ID NO:70 |
| TrX-10H-27M-29L-40R-58R-75A-99C-118C | TrX-HML RRA CC | SEQ ID NO:71 |
| TrX-10H-27M-29L-75A-99C-105H-118C-125A-129E | TrX-HML A CHC AE | SEQ ID NO:72 |
| TrX-10H-27M-29L-58R-75A-99C-105H-118C-125A-129E | TrX-HML RA CHC AE | SEQ ID NO:73 |
| TrX-10H-11D-27M-29L-58R-75A-99C-105H-118C -125A-129E | TrX-HDML RA CHC AE | SEQ ID NO:74 |
| TrX-10H-11D-27M-29L-40X-58R-75A-99C-105H-118C -125A-129E, wherein<br>X is C<br>X is F<br>X is H<br>X is Y<br>X is R | TrX-HDML XRA CHC AE | X is:<br>C- SEQ ID NO:75<br>F- SEQ ID NO:76<br>H- SEQ ID NO:77<br>Y- SEQ ID NO:78<br>R- SEQ ID NO:79 |
| TrX-10H-11D-27M-29L-40H-52C-58R-75A-99C-105H-118C-125A-129E | TrX-HDML HCRA CHC AE | SEQ ID NO:80 |
| TrX-10H-11D-27M-29L-40R-58R-75A-99C-105H-118C-125A-129E-144R-161R | TrX-HDML RRA CHC AERR | SEQ ID NO:81 |
| TrX-10H-11D-27M-29L-58R-75A-99C-105H-118C-125A-129E-131N | TrX-HDML RA CHC AEN | SEQ ID NO:82 |

Xylanases of the present invention comprising cysteine residues at positions 99 and 118 display improved thermophilicity, alkalophilicity or thermostability relative to wild-type xylanases. Such xylanases find use in a variety of applications in industry that require enzyme activities at temperatures and/or pH values above that of the native enzyme. For example, modified xylanases, as described herein, may be used for the purposes of bleaching pulp, improving the digestibility of poultry and swine feed, or the processing of precision devices.

The present invention also pertains to a modified xylanase comprising a substituted amino acid at position 40, the position determined from sequence alignment of the modified xylanase with a *Trichoderma reesei* xylanase II amino acid sequence as *Trichoderma reesei* xylanase II (Tr2, also referred to herein as TrX II) as indicated at the top of the sequences. The residues at position 99 and 118 (relative to Tr2) are in italics and indicated with an asterisk. The amino acids common to at least 75% of the listed Family 11 xylanases are indicated in bold. The residues common to all Family 11 xylanases are underlined. For xylanases with a cellulose-binding domain, only the catalytic core sequences are presented.

FIG. 2 shows the nucleotide sequence of TrX xylanase (SEQ ID NO:40), and the synthetic oligonucleotides TrX(1-91) and TrX (92-190) (SEQ ID NOs:61 to 64) used to constrict the sequence encoding the *Trichoderma reesei* xylanase II enzyme (TrX) in the plasmid pTrX.

Figure 3:
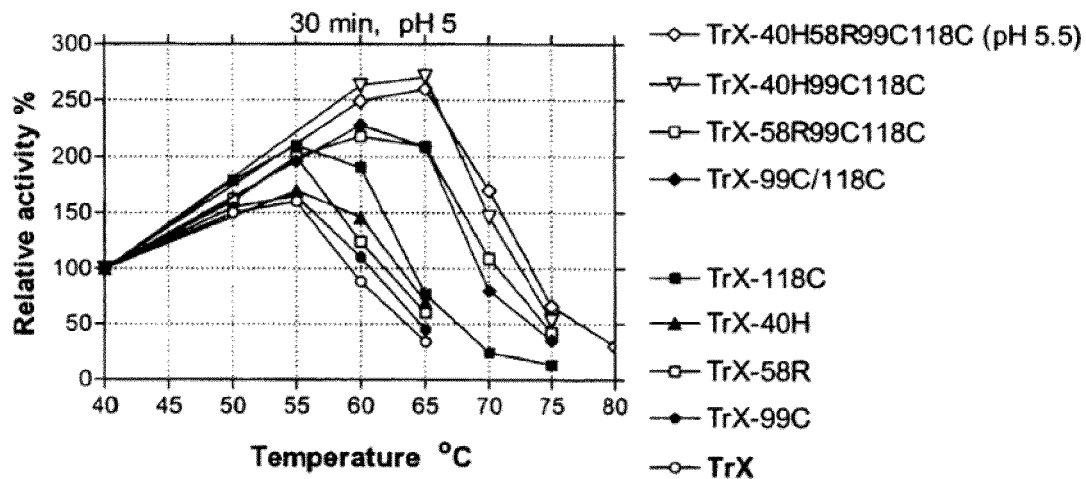

FIG. 3 shows the effect of temperature on the enzymatic activity of modified xylanases TrX-99C, TrX-58R, TrX-40H, TrX-118C, TrX-99C-118C, TrX-58-99C-118C, TrX-40H-99C-118C, TrX-40H-58R-99C-118C compared with TrX, at pH 5.0 during 30-minute incubations. The data are normalized to the activity observed at 40° C.

Figure 4:
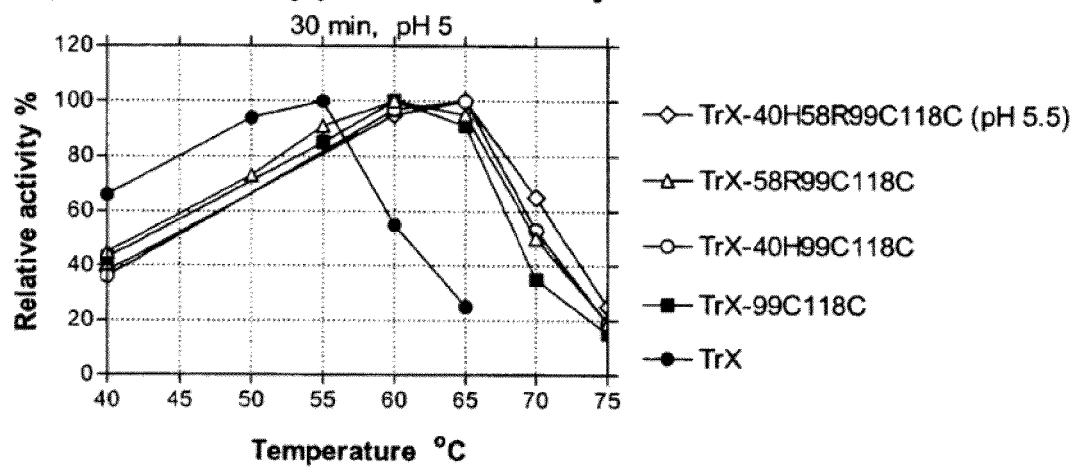

FIG. 4 shows the effect of temperature on the enzymatic activity of modified xylanases TrX-99C-118C, TrX-58R-99C-118C, TrX-40H-99C-118C, and TrX-40H-58R-99C-118C, compared with TrX, during 30-min incubations at pH 5.0. The data are based on those of FIG. 3, but normalized to the activity observed at the temperature optimum.

Figure 5:
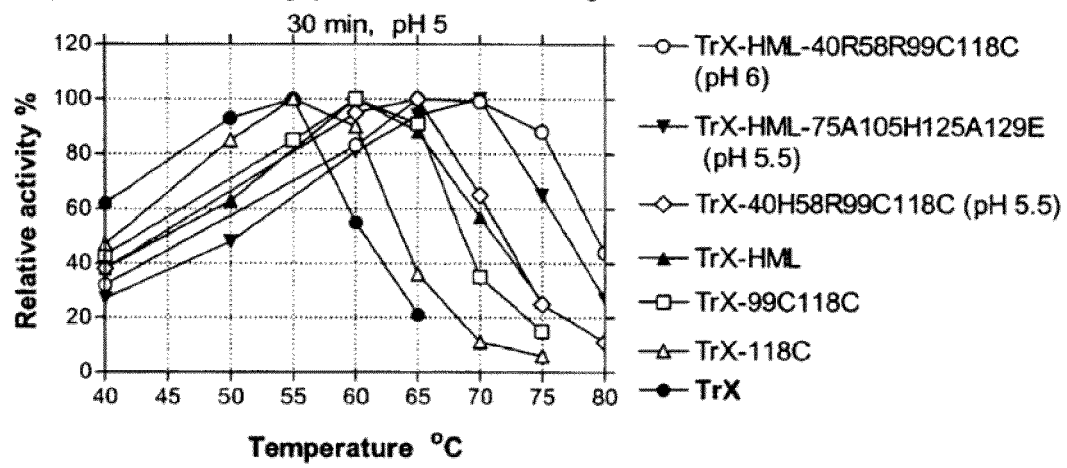

FIG. 5 shows the effect of temperature on the enzymatic activity of modified xylanases TrX-118C, TrX-99C-118C, TrX-40H-58R-99C-118C and TrX-10H-27M-29L-40R-58R-99C-118C compared with the known xylanases, TrX, TrX-10H-27M-29L and TrX-10H-27M-29L-75A-105H-125A-129E during 30-minute incubations at pH 5.0 unless otherwise indicated. The data are normalized to the activity observed at the temperature optimum.

Figure 6:
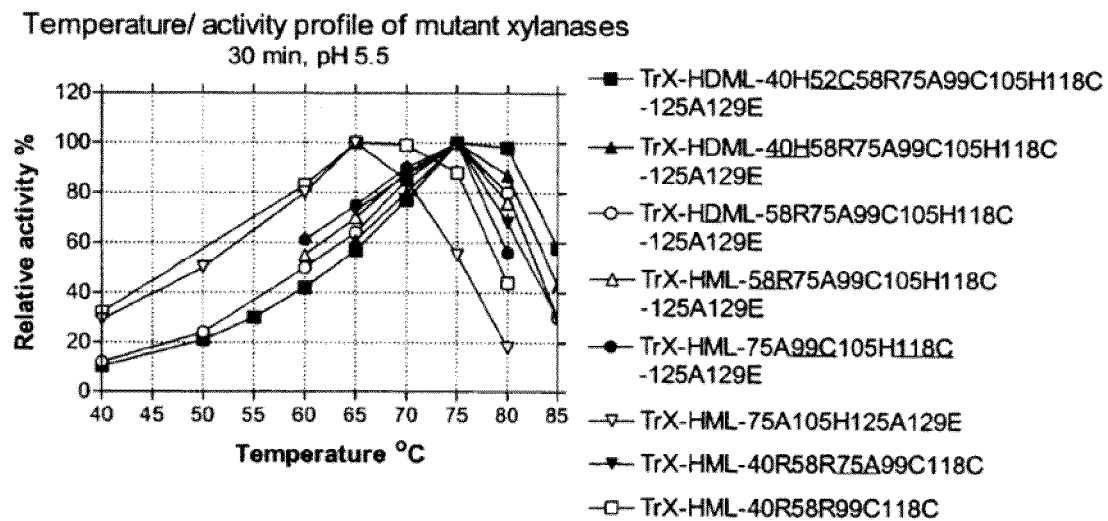

FIG. 6 shows the effect of temperature on the enzymatic activity of modified xylanases TrX-10H-27M-29L-40R-58R-99C-118C, TrX-10H-27M-29L-40R-58R-75A-99C-118C, TrX-10H-27M-29L-75A-99C-105H-118C-125A-129E, TrX-10H-27M-29L-58R-75A-99C-105H-118C-125A-129E, TrX-10H-11D-27M-29L-58R-75A-99C-105H-118C-125A-129E, TrX-10H-11D-27M-29L-40R-58R-75A-99C-105H-118C-125A-129E and TrX-10H-11D-27M-29L-40H-52C-58R-75A-99C-105H-118C-125A-129E,
compared with the known xylanase, TrX-10H-27M-29L-75A-105H-125A-129E, at pH 5.5 during 30-minute incubations. The data are normalized to the activity observed at the temperature optimum.

Figure 7:
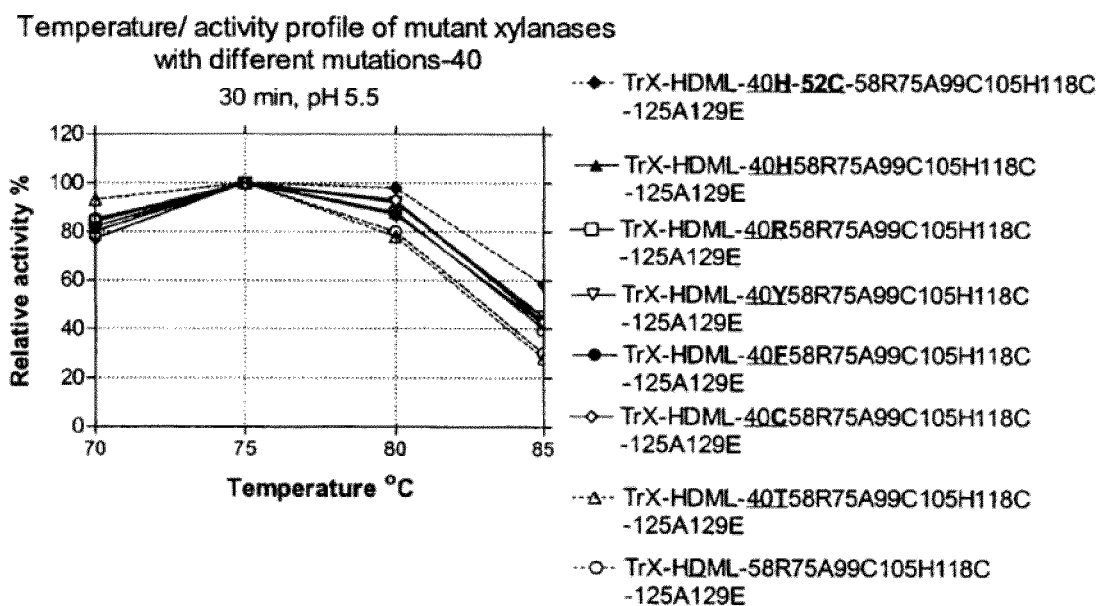

FIG. 7 shows the effect of temperature on the enzymatic activity of modified xylanases TrX-10H-11D-27M-29L-58R-75A-99C-105H-118C-125A-129E and TrX-10H-11D-27M-29L-40X-58R-75A-99C-105H-118C-125A-129E
(where X is T, C, F, Y, R and H) at pH 5.5 during 30-minute incubations. The data are normalized to the activity observed at the temperature optimum.

Figure 8:
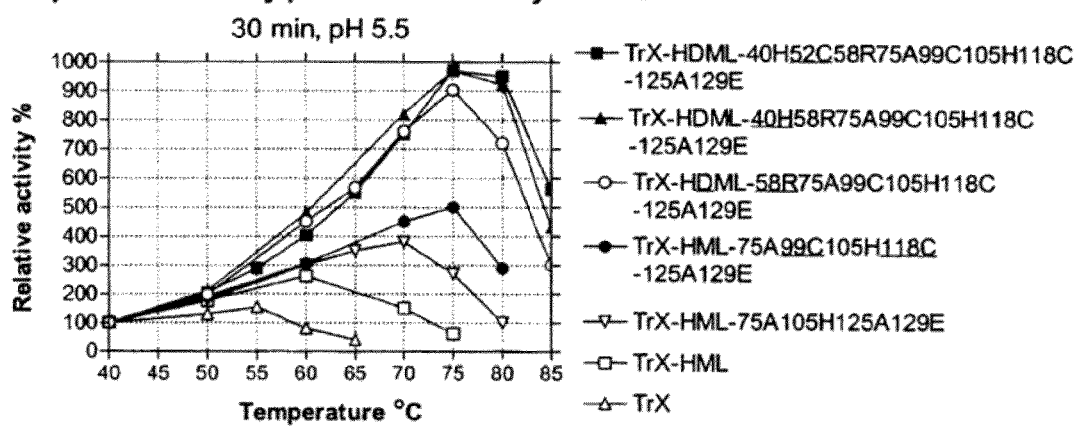

FIG. 8 shows the effect of temperature on the enzymatic activity of modified xylanases TrX-10H-27M-29L-75A-99C-105H-118C-125A-129E, TrX-10H-11D-27M-29L-58R-75A-99C-105H-118C-125A-129E, TrX-10H-11D-27M-29L-40H-58R-75A-99C-105H-118C-125A-129E and TrX-10H-11D-27M-29L-40H-52C-58R-75A-99C-105H-118C-125A-129E, compared with the known xylanases, TrX, TrX-10H-27M-29L and TrX-10H-27M-29L-75A-105H-125A-129E (pH 5.5), at pH 5.5 during 30-minute incubations. The data are normalized to the activity observed at 40° C.

Figure 9:
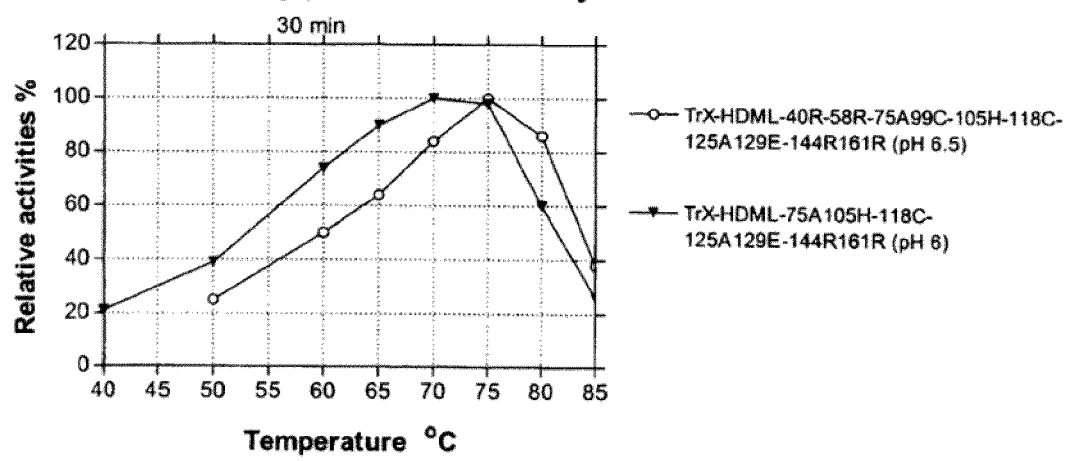

FIG. 9 shows the effect of temperature on the enzymatic activity of modified xylanases TrX-10H-11D-27M-29L-40R-58R-75A-99C-105H-118C-125A-129E-144R-161R (pH 6.5), compared to the known xylanase, TrX-10H-11D-27M-29L-75A-105H-118C-125A-129E-144R-161R (pH 6), during 30-minute incubations. The data are normalized to the activity observed at the temperature optimum.

Figure 10:
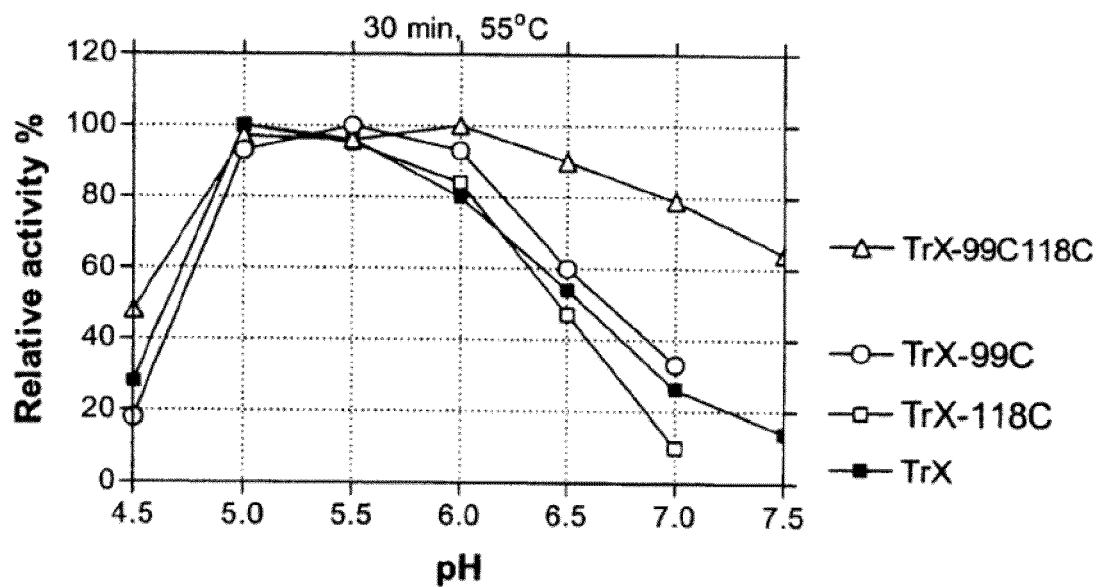

FIG. 10 shows the effect of pH on the enzymatic activity of modified xylanases TrX-99C and TrX-99C-118C, compared with native TrX and the known xylanase, TrX-118C, at pH 4.5-7.5, at 55° C. during a 30-minute incubation. The data are normalized to the activity observed at the pH optimum for each enzyme.

Figure 11:
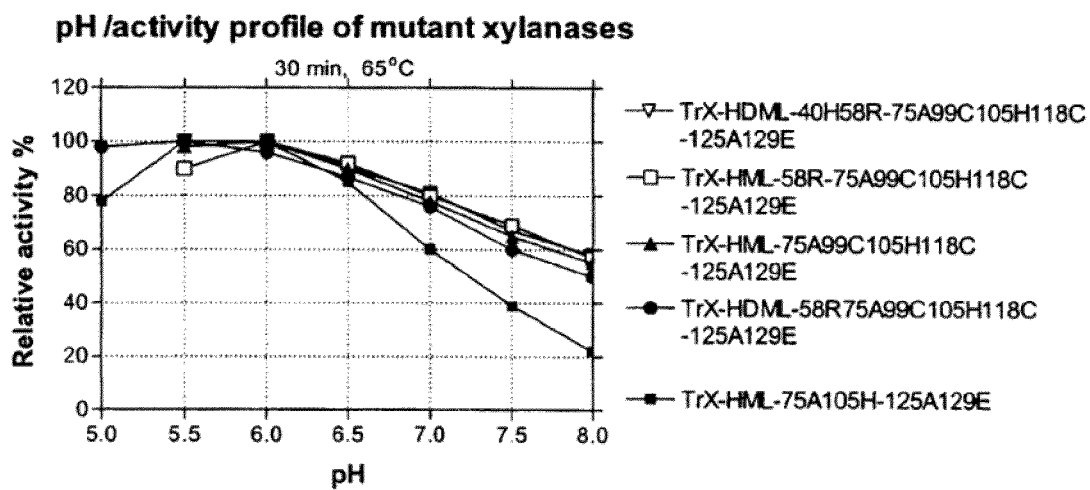

FIG. 11 shows the effect of pH on the enzymatic activity of modified xylanases TrX-10H-27M-29L-75A-99C-105H-118C-125A-129E, TrX-10H-27M-29L-58R-75A-99C-105H-118C-125A-129E, TrX-10H-11D-27M-29L-58R-75A-99C-105H-118C-125A-129E and TrX-10H-11D-27M-29L-40H-58R-75A-99C-105H-118C-125A-129E,
compared with the known xylanase, TrX-10H-27M-29L-75A-105H-125A-129E, at pH 5.0-8.0, at 65° C. during a 30-minute incubation. The data are normalized to the activity observed at the pH optimum for each enzyme.

Figure 12:
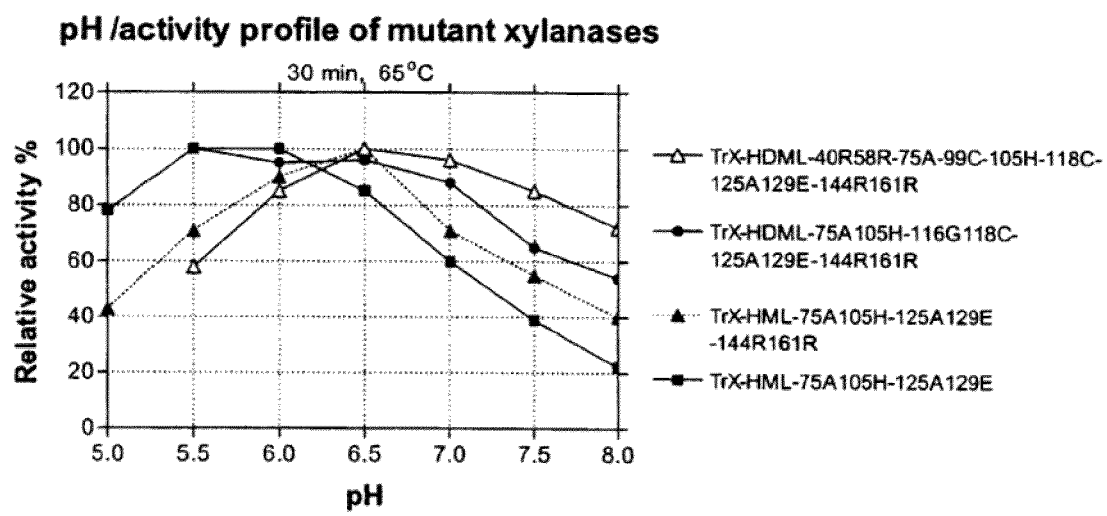

FIG. 12 shows the effect of pH on the enzymatic activity of modified xylanase TrX-10H-11D-27M-29L-40R-58R-75A-99C-105H-118C-125A-129E-144R-161R, compared with the known xylanases, TrX-10H-27M-29L-75A-105H-125A-129E, TrX-10H-27M-29L-75A-105H-125A-129E-144R-161R and TrX-10H-11D-27M-29L-75A-105H-116G-118C-125A-129E-144R-161R, at pH 5.0-8.0, at 65° C. during a 30-minute incubation. The data are normalized to the activity observed at the pH optimum for each enzyme.

Figure 13:
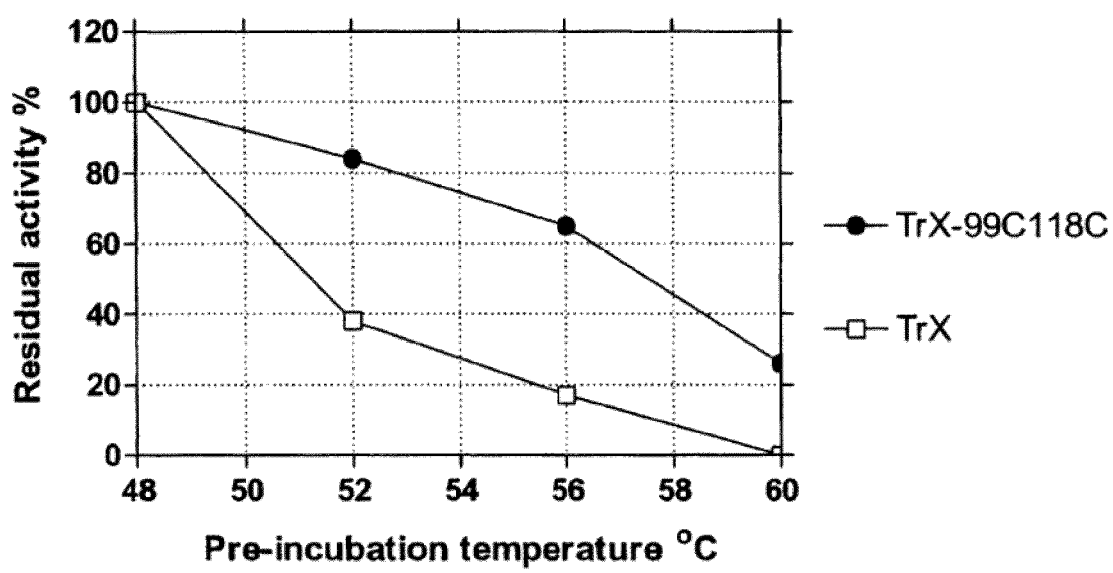

FIG. 13 shows the effect of temperature on the residual enzymatic activity of modified xylanase, TrX-99C-118C, compared with the natural xylanase, TrX, at 48° C., 52° C., 56° C., and 60° C. during 30-minute incubations without any soluble xylan substrate. The data are normalized to the activity observed at room temperature after a preincubation at 48° C.

Figure 14:
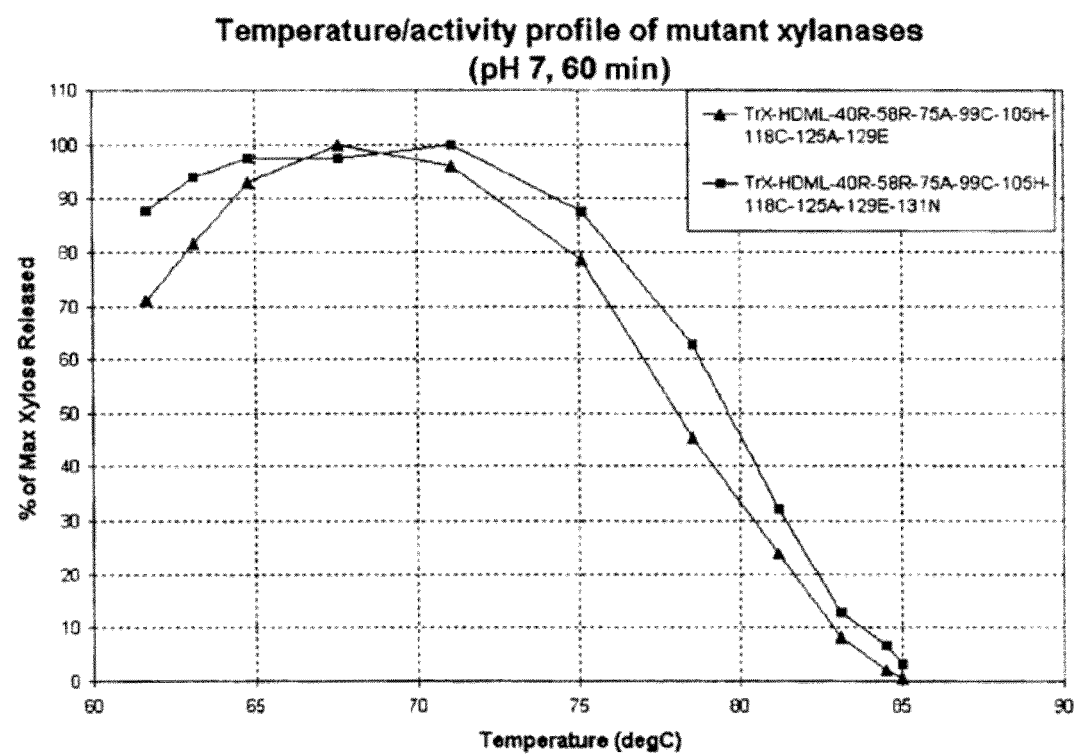

FIG. 14 shows the effect of temperature on the percentage of maximum xylose released for the modified xylanases TrX-10H-11D-27M-29L-40R-58R-75A-99C-105H-118C-125A-129E-131N and TrX-10H-11D-27M-29L-40R-58R-75A-99C-105H-118C-125A-129E on 1% wheat arabinoxylan substrate at pH 7 for 60 minutes.

Figure 15:
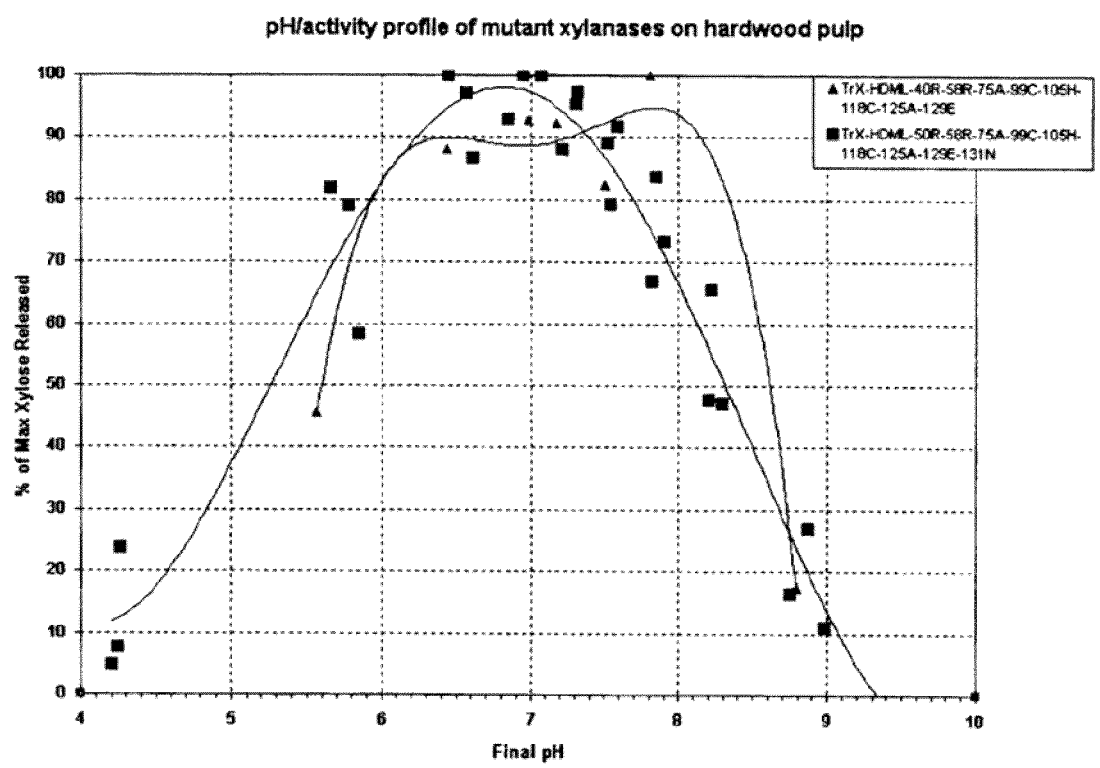

FIG. 15 shows the effect of pH on the percentage of maximum xylose released for the modified xylanases TrX-10H-11D-27M-29L-40R-58R-75A-99C-105H-118C-125A-129E-131N and TrX-10H-11D-27M-29L-40R-58R-75A-99C-105H-118C-125A-129E on hardwood pulp (10% consistency) at 70° C. for 60 minutes.

Figure 16:
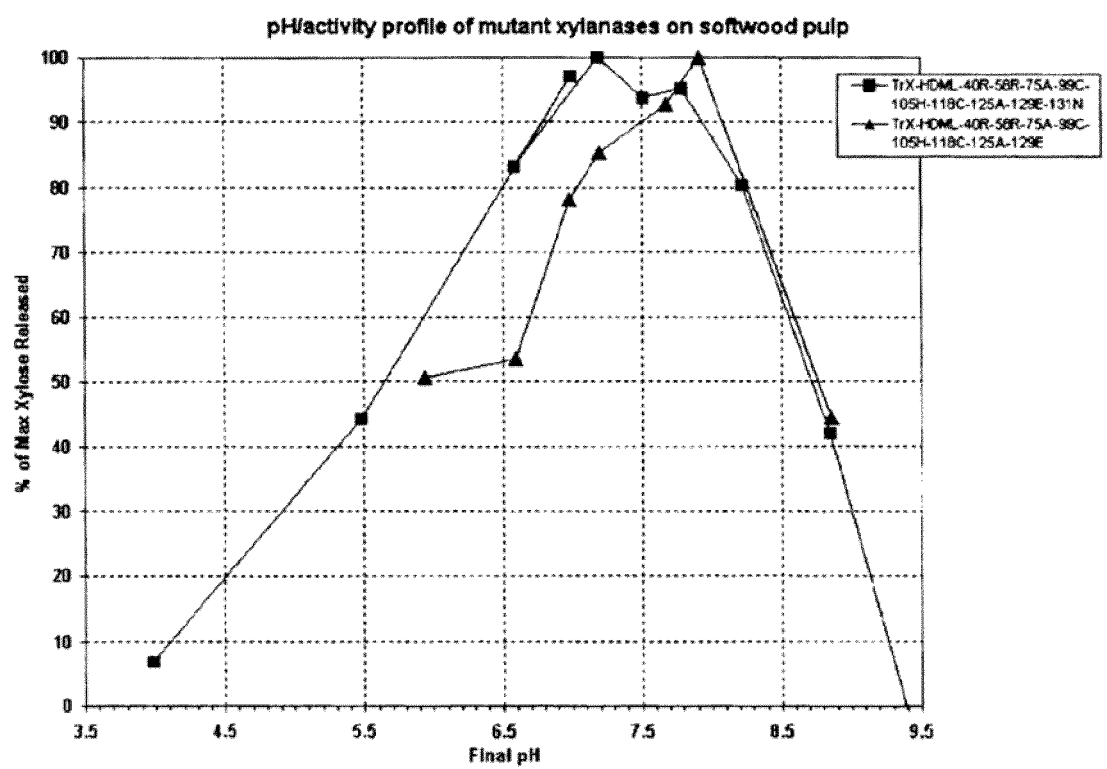

FIG. 16 shows the effect of pH on the percentage of maximum xylose released for the modified xylanases TrX-10H-11D-27M-29L-40R-58R-75A-99C-105H-118C-125A-129E-131N and TrX-10H-11D-27M-29L-40R-58R-75A-99C-105H-118C-125A-129E on softwood pulp (11% consistency) at 70° C. for 60 minutes.

Figure 17:
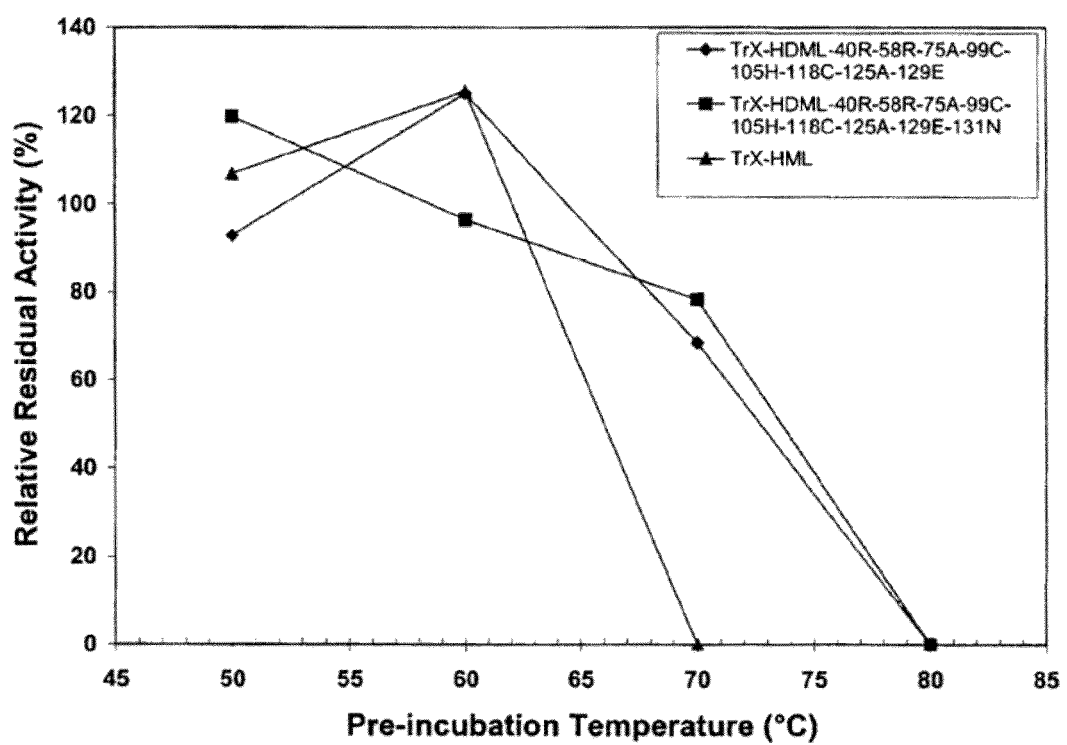

FIG. 17 shows the effect of pre-incubation temperature on the relative residual activity (%) of the modified xylanases TrX-10H-11D-27M-29L-40R-58R-75A-99C-105H-118C-125A-129E, TrX-10H-11D-27M-29L-40R-58R-99C-105H-118C-125E-131N and TrX-10H-27M-29L after 30-minute incubation at 50° C., 60° C., 70° C., and 80° C.

DESCRIPTION OF PREFERRED EMBODIMENT

The present invention relates to modified xylanases. More specifically, the invention relates to modified xylanases with improved performance at conditions of high temperature and pH and improved stability at high temperature.

The following description is of a preferred embodiment by way of example only and without limitation to the combination of features necessary for carrying the invention into effect.

The mechanism by which xylanases facilitate bleaching of pulp is not fully understood. Without wishing to be bound by theory, it has been postulated that the coloured lignin is connected to crystalline cellulose through xylan and xylanase enzymes facilitate bleaching of pulp by hydrolysing xylan, releasing coloured lignin in the pulp. Modified xylanases as outlined herein, may be used for the purposes of bleaching pulp or other applications requiring activities at temperatures and pH values above that of the wild-type enzyme. For the bio-bleaching of pulp, the preferred xylanase is derived from a xylanase classified in Family 11 (see Table 1).

Family 11 xylanase enzymes are a group of small enzymes of relatively low molecular mass (approximately 20 kDa and about 200 amino acid residues). The small size associated with Family 11 xylanases permits ready penetration of the pulp mass. Another advantage of Family 11 xylanases is that they are free of cellulase activity. Most of the Family 11 xylanases identified thus far are mesophilic and have low molecular masses (20 kDa). However, this family also includes at least three thermostable xylanases of higher molecular mass, *Thermomonospora fusca* xylanase A (TfX-A) of 296 amino acids and a molecular mass of approximately 32 kDa (Irwin et al., 1994; WO 95/12668, which are each incorporated herein by reference), *Thermomyces lanuginosus* xylanase (Tln) of 194 amino acids and a molecular mass of approximately 22 kDa (Gruber et al., 1998, which is incorporated herein by reference), and *Clostridium stercorarium* xylanase A of 511 amino acids and a molecular mass of approximately 56 kDa. The *Clostridium stercorarium* xylanase A enzyme exhibits maximum activity at a temperature of 70° C. (Sakka et al., 1993, which is incorporated herein by reference).

Some large thermostable Family 11 xylanases differ from the small mesophilic enzymes by the possession of a hydrophobic cellulose-binding domain (CBD) in the extended C-terminus of the enzyme. The TfX-A enzyme is composed of a catalytic core sequence of 189 residues common to all Family 11 xylanases, and a cellulose-binding domain of 107 residues. The larger *C. stercorarium* xylanase A has two copies of the cellulose-binding domain.

Proteins are classified as Family 11 xylanases if (a) they exhibit the ability to hydrolyze internal beta-1, 4 glycosidic bonds between adjacent xylose residues in the main chain of the xylan polymer and (b) they exhibit the primary and secondary structural signatures associated with Family 11 xylanases. All Family 11 xylanases from bacterial and fungal sources share the same general molecular structure comprising mainly beta-sheets, turns and a single alpha helix. Alignment of the amino acid sequences of 82 Family 11 xylanases ranging in length from 173 to 220 amino acids and spanning a broad range of isoelectric points (pI 3.5 to 10.25), pH optima (2.0 to 8.0) and temperature optima (45° C. to 75° C.) identified highly conserved signature sequences in beta strands B5, B6, and B8 as well as in the alpha helix (Sapag et al., 2002). Furthermore, the secondary structure of Family 11 xylanases is highly conserved. Pairwise comparisons of the C-alpha atoms of ten Family 11 xylanase exhibiting from 31-97% identity in amino acid sequence using structural coordinates from the Protein Data Bank (PDB) showed that the root-mean-square deviation (rmsd) ranged from 0.6 to 1.4 Å (Hakulinen et al. 2003; incorporated herein by reference). This level of deviation is within the typical resolution of most X-ray crystal structures. Furthermore, all Family 11 xylanases contain two conserved glutamate residues at positions 86 and 177 (see FIG. 1; based on *Trichoderma reesei* xylanase II (TrX II, or Tr2) amino acid numbering), which are located on beta-strands B4 and B5 (Torronen & Rouvinen, 1995; Sapag et al., 2002, which are each incorporated herein by reference).

Therefore, a family 11 zylanase may be defined as comprising from about 80-100% or any amount therebetween, 90-100% or any amount therebetween, 95-100% or any amount therebetween, or from about 80, 82, 84, 86, 88, 90, 92, 94, 96, 98, 100%, sequence identity within each of the beta strands B5, B6, B8, and the alpha helix. A Family 11 xylanase may also be defined as comprising glutamate at positions 86 and 177, based on TrX II amino acid numbering (see FIG. 1).

Given the highly conserved structure within the Family 11 xylanase, one skilled in the art can apply known methods, including the approaches outlined herein, to increase the thermophilicity, thermostability and/or alkalophilicity of any Family 11 xylanase, non-limiting examples of which are described in Table 1 below. Other non-limiting examples of Family 11 xylanases are presented in Sapag et al., (2002) and Hakulinen et al., (2003) and disclosed at the URL: cazy.org/fam/GH11.html, which are each incorporated herein by reference.

Moreover, the modified Family 11 xylanase may comprise further mutations in addition to the cysteine residues introduced at positions 99 and 118. These additional mutations should be introduced at compatible positions within the amino acid sequence, for example at positions that are non-conserved (see FIG. 1). Furthermore, whether or not a given mutation is compatible with the disulfide mutation can be determined with ease by one of skill in the art by measuring the thermophilicity, alkalophilicity and/or thermostability as described herein after introducing such mutation(s). Non-limiting examples of mutations which are compatible with the 99/118 mutation are given in Table 2. These additional mutation(s) may be introduced using known recombinant techniques or by directed evolution and may further contribute to the increased thermophilicity, thermostability, alkalophilicity, or a combination thereof, of the enzyme.

TABLE 1

Family 11 xylanase enzymes

| Microbe | Xylanase | SEQ ID NO |
|---|---|---|
| *Aspergillus niger* | Xyn A | SEQ ID NO:1 |
| *Aspergillus awamori* var. *kawachi* | Xyn B | SEQ ID NO:19 |
| *Aspergillus kawachii* | Xyn C | — |
| *Aspergillis tubigensis* | Xyn A | SEQ ID NO:2 |
| *Bacillus circulans* | Xyn A | SEQ ID NO:3 |
| *Bacillus pumilus* | Xyn A | SEQ ID NO:4 |
| *Bacillus subtilis* | Xyn A | SEQ ID NO:5 |
| *Cellulomonas fimi* | Xyn D | — |
| *Chainia sp.* | Xyn | — |
| *Clostridium acetobutylicum* | Xyn B | SEQ ID NO:6 |
| *Clostridium stercorarium* | Xyn A | SEQ ID NO:7 |
| *Fibrobacter succinogenes* | Xyn II | SEQ ID NO:18 |
| *Neocallimasterix patriciarum* | Xyn A | — |
| *Nocardiopsis dassonvillei* | Xyn II | — |
| *Ruminococcus flavefaciens* | Xyn A | SEQ ID NO:8 |
| *Schizophyllum commune* | Xyn | SEQ ID NO:9 |
| *Streptomyces lividans* | Xyn B | SEQ ID NO:10 |

TABLE 1-continued

Family 11 xylanase enzymes

| Microbe | Xylanase | SEQ ID NO |
|---|---|---|
| Streptomyces lividans | Xyn C | SEQ ID NO:11 |
| Streptomyces sp. No. 36a | Xyn | SEQ ID NO:12 |
| Streptomyces thermoviolaceus | Xyn II | — |
| Thermomonospora fusca | Xyn A | SEQ ID NO:13 |
| Thermomyces lanuginosus | Xyn | SEQ ID NO:20 |
| Trichoderma harzianum | Xyn | SEQ ID NO:14 |
| Trichoderma reesei | Xyn I | SEQ ID NO:15 |
| Trichoderma reesei | Xyn II | SEQ ID NO:16 |
| Trichoderma viride | Xyn | SEQ ID NO:17 |

Examples of preferred Family 11 xylanases, which are not meant to be limiting, include *Trichoderma reesei* xylanase II, *Trichoderma reesei* xylanase I, *Trichoderma viride* xylanase, *Streptomyces lividans* xylanase B and *Streptomyces lividans* xylanase C. For example, the mutant xylanase of the present invention may comprise a mutant *Trichoderma reesei* xylanase II enzyme.

By "modified xylanase", it is meant a xylanase comprising a mutation or alteration of the natural xylanase sequence. The mutation or alteration is not found in the corresponding native xylanase. A xylanase molecule may be modified using techniques that are known to one of skill in the art. These techniques include, but are not limited to, site directed mutagenesis, cassette mutagenesis, random mutagenesis, synthetic oligonucleotide construction, cloning and other genetic engineering techniques. An example of a suitable technique to produce mutations in xylanases which render the enzyme more thermophilic and/or alkalophilic compared to the native enzyme is site-directed mutagenesis. However, it is also considered within the scope of the invention to use other techniques to introduce mutations that are known to those of skill in the art.

By the term "optimal activity", it is meant the activity of the particular enzyme at a pH where maximum activity is observed (i.e. optimal pH) and a temperature where maximal activity is observed (i.e. optimal temperature) over a given length of time.

A xylanase is "thermophilic," as used herein, if the xylanase exhibits a maximum effective temperature of between about 60° C. and about 90° C. By "maximum effective temperature" or "MET", it is meant the highest temperature at which a xylanase exhibits at least 80% of its optimal activity. For the purposes of this specification, the MET of a xylanase is determined by measuring the temperature profile of a xylanase using the standard assay for measurement of xylanase activity as detailed in Example 2.3 and modified as detailed in Example 3. The activity of the xylanase is measured at its pH optimum. The temperatures at which the modified xylanase exhibits at least about 80% of its optimal (maximum) activity are determined and the highest temperature is the MET.

The modified xylanase may have a MET of about 60° C., 62° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 86° C., 88° C., or 90° C., or any temperature therebetween. In a non-limiting example, the modified xylanase may have a MET between about 62° and about 85° C. or any range therebetween; between about 65° C. and about 85° C. or any range therebetween; between about 68° C. and about 85° C. or any range therebetween; or between about 70° C. and about 85° C. or any range therebetween.

A xylanase is "thermostable," as used herein, if it has a $T_{50}$ of between about 55° C. and about 85° C. The "$T_{50}$" is the incubation temperature at which the modified or the natural enzyme retains 50% of its residual activity, after an incubation time of 30 minutes. The $T_{50}$ of a xylanase may be determined by the assay detailed in Example 5. As set forth in Example 5, the residual activity at 48° C. is normalized to 100%.

The modified xylanase may have a $T_{50}$ of about 55° C., 56° C., 57° C., 58° C., 59° C., 60° C., 64° C., 68° C., 72° C., 76° C., 80° C. or 85° C., or any temperature therebetween. In a non-limiting example, the modified xylanase may have a $T_{50}$ between about 54° C. and about 80° C. or any range therebetween; between about 56° C. and about 80° C. or any range therebetween; or between about 58° C. and about 80° C. or any range therebetween.

The use of the terms thermophilicity and thermostability has, in the past, been confused in the literature, as they have been used interchangeably. However, the use of the terms as defined herein is consistent with the usage of the terms in the art (Mathrani and Ahring, 1992).

A xylanase is alkalophilic, as used herein, if the xylanase has a maximum effective pH (MEP) of between about pH 6.0 and about pH 8.5. By "maximum effective pH" or "MEP", it is meant the highest pH at which a xylanase exhibits at least 80% of its optimal activity. The MEP may be determined by measuring the pH profile of a xylanase as set out in Example 4. The pH for which at least 80% of the optimal (maximum) activity is determined and the highest pH is the MEP.

The modified xylanase may have a MEP of pH 6.2, 6.5, 6.6, 6.7, 6.8, 6.9, 7.0, 7.1, 7.2, 7.3, 7.4, 7.5, 7.6, 7.7, 7.8, 8.0, or 8.5, or any pH therebetween. In a non-limiting example, the MEP may be between about pH 6.5 and about 8.5 or any range therebetween; or between about pH 6.8 and 8.0 or any range therebetween; or between about pH 7.0 and about 8.0 or any range therebetween.

By "TrX numbering", it is meant the numbering corresponding to the position of amino acids based on the amino acid sequence of TrX (Xyn II—Table 1; Tr2—FIG. 1; SEQ ID NO:16). As disclosed below, and as is evident by FIG. 1, Family 11 xylanases exhibit a substantial degree of sequence similarity. Therefore, by aligning the amino acids to optimize the sequence similarity between xylanase enzymes, and by using the amino acid numbering of TrX as the basis for numbering, the positions of amino acids within other xylanase enzymes can be determined relative to TrX. Standard methods known to one of skill in the art may be used to align these sequences.

As described in more detail herein, several mutant xylanases have been prepared that exhibit enhanced thermophilicity, alkalophilicity and/or thermostability. A list of several mutants, which is not to be considered limiting in any manner, is presented in Table 2.

TABLE 2

Modified xylanases

| Mutant TrX | Mutations involved | SEQ ID NO: |
|---|---|---|
| TrX-R | TrX: K58R | — |
| TrX-H | TrX: S40H | 65 |
| TrX-C | TrX: S99C | — |
| TrX-CC | TrX: S99C and Y118C | 66 |
| TrX-R CC | TrX: K58R, S99C and Y118C | 68 |
| TrX-H CC | TrX: S40H, S99C and Y118C | 67 |
| TrX-HR CC | TrX: S40H, K58R, S99C and Y118C | 69 |
| TrX-HML RR CC | TrX: N10H, Y27M, N29L, S40R, K58R, S99C and Y118C | 70 |
| TrX-HML RRA CC | TrX: N10H, Y27M, N29L, S40R, K58R, S75A, S99C and Y118C | 71 |
| TrX-HML A CHC AE | TrX: N10H, Y27M, N29L, S75A, S99C, L105H, Y118C, Q125A and I129E | 72 |
| TrX-HML RA CHC AE | TrX: N10H, Y27M, N29L, K58R, S75A, S99C, L105H, Y118C, Q125A and I129E | 73 |
| TrX-HDML RA CHC AE | TrX: N10H, N11D, Y27M, N29L, K58R, S75A, S99C, L105H, Y118C, Q125A and I129E | 74 |
| TrX-HDML HRA CHC AE | TrX: N10H, N11D, Y27M, N29L, S40H, K58R, S75A, S99C, L105H, Y118C, Q125A and I129E | 77 |
| TrX-HDML CR ACHC AE | TrX: N10H, N11D, Y27M, N29L, S40C, K58R, S75A, S99C, L105H, Y118C, Q125A and I129E | 75 |
| TrX-HDML TRA CHC AE | TrX: N10H. N11D, Y27M, N29L, S40T, K58R, S75A, S99C, L105H, Y118C, QI25A and I129E | — |
| TrX-HDML YRA CHC AE | TrX: N10H, N11D, Y27M, N29L, S40Y, K58R, S75A, S99C, L105H, Y118C, Q125A and I129E | 78 |
| TrX-HDML FRA CHC AE | TrX: N10H, N11D, Y27M, N29L, S40F, K58R, S75A, S99C, L105H, Y118C, Q125A and I129E | 76 |
| TrX-HDML RRA CHC AE | TrX: N10H, N11D, Y27M, N29L, S40R, K58R, S75A, S99C, L105H, Y118C, Q125A and I129E | 79 |
| TrX-HDML ARA CHC AE | TrX: N10H, N11D, Y27M, N29L, S40A, K58R, S75A, S99C, L105H, Y118C, Q125A and I129E | — |
| TrX-HDML HCRA CHC AE | TrX: N10H, N11D, Y27M, N29L, S40H, Q52C, K58R, S75A, S99C, L105H, Y118C, Q125A and I129E | 80 |
| TrX-HDML RRA CHC AERR | TrX: N10H, N11D, Y27M, N29L, S40R, K58R, S75A, S99C, L105H, Y118C, Q125A, I129E, H144R and Q161R | 81 |
| TrX-HDML RA CHC AEN | TrX: N10H, N11D, Y27M, N29L, 58R, 75A, 99C, 105H, 118C, 125A, 129E and 131N | 82 |

Mutant xylanases described in WO 03/046169, U.S. Pat. No. 5,759,840, WO 01/92487 and WO 2005/093072 (the contents of which are incorporated herein by reference) may be further modified to introduce cysteine residues at positions 99 and 118. Non-limiting examples of mutant xylanases that may be modified in accordance with the present invention are listed in Table 3.

TABLE 3

Modified xylanases described in WO 03/046169, U.S. Pat. No. 5,759,840 and WO 01/92487

| Mutant TrX | Mutation |
| --- | --- |
| TrX-C[a] | TrX: Y118C |
| TrX-HML[b] | TrX: N10H, Y27M and N29L |
| TrX-HML-AHAE[c] | TrX: N10H, Y27M, N29L, S75A, L105H, Q125A and I129E |
| TrX-HDML AH CAERR[a] | TrX: N10H, N11D, Y27M, N29L, S75A, L105H, Y118C, Q125A, I129E, H144R and Q161R |
| TrX-HDML AHGC AERR[a] | TrX: N10H, N11D, Y27M, N29L, S75A, L105H, D116G, Y118C, Q125A, I129E, H144R and Q161R |
| TrX-HML AHAE RR[c] | TrX: N10H, Y27M, N29L, S75A, L105H, Q125A, I129E, H144R and Q161R |

[a]WO 03/046169 (Sung)
[b]U.S. Pat. No. 5,759,840 (Sung et al.)
[c]WO 01/92487 (Sung)

Increasing the Thermophilicity of Xylanase

The effect of temperature on the hydrolysis of xylan by *Trichoderma reesei* xylanase TrX with the single mutations S40H (TrX-40H), K58R (TrX-58R), S99C (TrX-99C), or Y118C (TrX-118C) is shown in FIG. 3.

The increase in thermophilicity of a Family 11 xylanase by the single mutation, Y118C, as in the modified xylanase, TrX-118C, has been described in WO 03/046169 (Sung). However, the possibility of producing a disulfide bond based on a cysteine at position 118 and another cysteine to increase thermostability, thermophilicity or alkalophilicity of a xylanase has never been reported. The present invention involves the construction of a 99C/118C-disulfide linkage for such purpose, based on either a naturally occurring or generated Cys-118 with a second cysteine at residue-99 which is either naturally occurring or created via a mutation S99C.

To verify that any improved activity at higher temperatures is the result of the formation of a disulfide bond, the single mutation S99C was tested (TrX-99C; FIG. 3). This mutant xylanase, TrX-99C, showed no improvement of enzymatic activity at higher temperature, as compared to natural TrX. Therefore, the S99C single mutation alone had no effect on the temperature/activity profile of TrX.

However, when mutations S99C and Y118C were incorporated in the form of a double mutant xylanase, TrX-99C-118C, there was a dramatic enhancement of thermophilicity (FIGS. 3 and 4), even when compared to the single mutant TrX-118C. The improvement of the temperature optima of the double mutant TrX-99C-118C over the natural xylanase (TrX) and TrX-118C is about 7° C. and 5° C., respectively (FIGS. 3 and 4). In addition to a higher temperature optimum, TrX-99C-118C also exhibited higher optimal activity than TrX at their respective temperature optima (FIG. 3).

The single mutation, S40H, in xylanase TrX-40H showed an improved enzymatic activity at higher temperature (FIG. 3), as compared to the wild type TrX. The positive effect on thermophilicity due to this mutation was confirmed in another mutant xylanase, TrX-40H-99C-118C, (FIGS. 3 and 4) when compared to TrX-99C-118C.

In the case of the modified xylanase TrX-58R, the mutation K58R by itself could not improve the activity of the natural TrX (FIG. 3), as previously reported by Turunen et al. (2002). However, in the mutant xylanases containing the mutations S99C and Y118C, the mutation K58R increased enzymatic activity at higher temperatures. This was confirmed by comparing the thermophilicity of the mutant xylanases TrX-58R-99C-118C and TrX-40H-58R-99C-118C (FIGS. 3 and 4) to that of the xylanases TrX-99C-118C and TrX-40H-99C-118C, respectively. Although the mutation, K58R, by itself failed to improve the activity of xylanase at higher temperature, it has a positive effect on thermophilicity in combination with the other mutations S40H and S99C/Y118C.

The mutations above are compatible with other advantageous xylanase mutations previously described in the art. The additive effect of these mutations in combination with previously disclosed mutations was demonstrated in the construction of the combined variant xylanases possessing a higher temperature optima and optimal activity, as described below.

The mutations N10H, Y27M and N29L have been shown to increase the thermophilicity of TrX in the form of the mutant TrX-10H-27M-29L (TrX-HML; see U.S. Pat. No. 5,759,840). Incorporation of mutations S40H, K58R and S99C/Y118C in TrX-10H-27M-29L created the variant xylanase TrX-10H-27M-29L-40R-58R-99C-118C, with further improvement in enzymatic activity at higher temperatures (FIG. 5).

The mutations N10H, Y27M, N29L, S75A, L105H, Q125A and 119E have also been shown to increase the thermophilicity of TrX (mutant TrX-10H-27M-29L-75A-105H-125A-129E; see WO 01/92487). Incorporation of mutations S40H, K58R and S99C/Y118C to TrX-10H-27M-29L-75A-105H-125A-129E created the variant xylanases TrX-10H-27M-29L-40R-58R-75A-99C-118C, TrX-10H-27M-29L-75A-99C-105H-118C-125A-129E, and TrX-10H-27M-29L-58R-75A-99C-105H-118C-125A-129E, showing enhanced enzymatic activity at higher temperatures (FIGS. 6 and 8).

Addition of an N11D mutation created modified xylanase TrX-10H-11D-27M-29L-58R-75A-99C-105H-118C-125A-129E (FIGS. 6, 7 and 8). A series of mutants based on this xylanase bearing another mutation at position 40 were constructed to determine those amino acid residues that enhance the thermophilicity of the enzyme. Different mutations at position 40 (S40C, F, R, Y, A or T) were introduced to create seven new mutant xylanases: TrX-10H-11D-27M-29L-40X-58R-75A-99C-105H-118C-125A-129E (where X is A, C, F, H, R, Y or T). Similar to xylanases TrX-40H and TrX-40H-99C-118C, with fewer mutations, the introduction of mutations S40H or S40R moderately improved the relative activity of the resultant variant xylanases at a higher temperature as compared to the parent enzyme (FIGS. 6, 7 and 8). Other mutations like S40C, S40F and S40Y also exhibited the same enhancing effect (FIG. 7), while S40T and S40A showed no such enhancing effect on the temperature/activity profile (FIG. 7).

The positive effect on the thermophilicity of Family 11 xylanases via the mutation of Ser 40 into Cys, Phe, Tyr, His or Arg has not been described previously. No known Family 11 xylanases possess the residue Cys, Phe, Tyr or His at position 40. The Arg residue, though present in the thermophilic *Thermomyces lanuginosus* Xyn (FIG. 1), also exists in the mesophilic *Steptomyces lividan* Xln B.

Another mutation, Q52C, was introduced into TrX-10H-11D-27M-29L-40H-58R-75A-99C-105H-118C-125A-129E. The resulting mutant xylanase TrX-10H-11D-27M-29L-40H-52C-58R-75A-99C-105H-118C-125A-129E was able to retain significantly higher relative activity at 80 and 85° C., in comparison to the parent enzyme (FIGS. 6, 7 and 8). No Family 11 xylanase possesses the residue Cys at position 52.

The mutations H144R and Q161R have previously been shown to increase the pH optimum of xylanase TrX-10H-11D-27M-29L-75A-105H-118C-125A-129E-144R-161R (TrX-HDML-AH-118C-AE-RR; WO 03/046169). Addition of mutations S40R, K58R and S99C resulted in the mutant xylanase TrX-10H-11D-27M-29L-40R-58R-75A-99C-105H-118C-125A-129E-144R-161R, which retains greater activity at higher temperatures of 80 and 85° C. (FIG. 9).

The above results demonstrate that the enhancing effect of the mutations S40X (where X is C, F, H, R or Y), Q52C, K58R and S99C/Y118C on the thermophilicity of the mutant xylanase are not only complementary or additive to each other, but also to other mutations described in U.S. Pat. No. 5,759,840, WO 01/92487 and WO 03/046169.

The mutation 131N was introduced into the modified xylanase TrX-10H-11D-27M-29L-40R-58R-75A-99C-105H-118C-125A-129E. The resulting mutant xylanase TrX-10H-11D-27M-29L-40R-58R-75A-99C-105H-118C-125A-129E-131N showed a slightly higher temperature optimum than TrX-10H-11D-27M-29L-40R-58R-75A-99C-105H-118C-125A-129E (FIG. 14). These results demonstrate that the mutation 131N is compatible with the 99C/118C disulfide mutation and other mutations which increase thermophilicity.

Increasing the Alkalophilicity of Xylanase

The effect of the disulfide mutation S99C/Y118C on the pH/activity profile of xylanase is shown in FIG. 10. The mutant xylanase TrX-99C-118C maintained greater activity at the higher pH values of 6.5-7.5 as compared to the natural xylanase TrX. The pH range for xylanase TrX-99C-118C to maintain 80% optimal activity is 4.8-7.0, which is broader than the range of 4.8-6.0 for the corresponding natural or native xylanase TrX. These results demonstrate the positive contribution of the 99C/118C mutations on the alkalophilicity of the xylanase TrX.

In order to identify the direct cause of higher activity at higher pH, xylanases with only one of the S99C/Y118C mutations were compared to both TrX-99C-118C and the natural xylanase TrX. These two xylanases with a single mutation, TrX-99C or TrX-118C, showed similar pH/activity profiles as TrX (FIG. 10). This confirmed that the improvement of activity at higher pH is a result of the disulfide bond formed via a combination of mutations S99C and Y118C, and not the single Cys mutations.

The effect of the mutations S40X (where X is H or R), K58R and S99C/Y118C on the pH/activity profile of xylanase was also studied in two groups of mutants constructed as described above.

The first group was derived from the mutant TrX-10H-27M-29L-75A-105H-125A-129E (see WO 01/92487). The disulfide mutant xylanase TrX-10H-27M-29L-75A-99C-105H-118C-125A-129E showed enhanced activity of 75, 60 and 50% at respective pH values of 7.0, 7.5 and 8.0 (FIG. 11) versus the parent xylanase, TrX-10H-27M-29L-75A-105H-125A-129E, which only showed 60, 40 and 22% enhanced activity at these pH values, respectively. This confirms the contribution of the 99C/118C mutations on the alkalophilicity of xylanases, with compatibility to the alkalophic and thermophilic mutations previously disclosed in the art.

Other members of this group were constructed with additional mutations at positions 40 and 58, which also contained the 99C/118C disulfide mutation. This includes TrX-10H-27M-29L-58R-75A-99C-105H-118C-125A-129E, TrX-10H-11D-27M-29L-58R-75A-99C-105H-118C-125A-129E and TrX-10H-11D-27M-29L-40H-58R-75A-99C-105H-118C-125A-129E. However, these mutants did not show any improved activity at the higher pH (FIG. 11) as compared to the parent TrX-10H-27M-29L-75A-99C-105H-118C-125A-129E xylanase. Although these thermophilic mutations at positions 40 and 58 could not improve the alkalophilicity of the xylanase, they have no adverse effect, thus demonstrating that they are compatible in the construction of a thermophilic and alkalophilic xylanase with other advantageous mutations.

The enhancing effect of the S99C/Y118C mutations was further demonstrated in a second group based on TrX-10H-27M-29L-75A-105H-125A-129E-144R-161R, a xylanase containing two mutations, H144R and Q161R, which have successfully increased the pH optimum of a xylanase in WO 01/92487. With the 99C/118C mutations, the mutant xylanase TrX-10H-11D-27M-29L-40R-58R-75A-99C-105H-118C-125A-129E-144R-161R exhibited greater activity at higher pH than its parent TrX-10H-27M-29L-75A-105H-125A-129E-144R-161R (FIG. 12). It also outperformed another xylanase, TrX-10H-11D-27M-29L-75A-105H-116G-118C-125A-129E-144R-161R (FIG. 12), a mutant xylanase which showed the most improved pH/activity profile among mutant xylanases in WO 03/046169. This is another non-limiting example demonstrating the compatibility of the 99C/118C mutations with other alkalophilic mutations.

The effect of the 131N mutation on the pH/activity profile of the mutant xylanase TrX-10H-11D-27M-29L-40R-58R-75A-99C-105H-118C-125A-129E was also investigated. As shown in FIGS. 15 and 16, the modified xylanase TrX-10H-11D-27M-29L-40R-58R-75A-99C-105H-118C-125A-129E-131N has a slightly broader pH optimum on both hardwood (FIG. 15) and softwood (FIG. 16) than TrX-10H-11D-27M-29L-40R-58R-75A-99C-105H-118C-125A-129E. This is yet another non-limiting example demonstrating the compatibility of the 99C/118C mutations with other mutations which increase alkalophilicity.

Increasing the Thermostability of Xylanase

The thermostability of the mutant xylanase was compared via incubation in the absence of substrate at different temperatures. After 30 minutes, the residual activity of the xylanase was determined via a standard assay with soluble xylan as a substrate.

The effect of the 99C/118C mutations on the thermostability of xylanase was determined via comparative study of the TrX-99C-118C mutant and the natural TrX. After incubation at higher temperatures for 30 minutes, the former retained greater residual activity than the latter (FIG. 13).

The $T_{50}$ was determined. For the disulfide xylanase TrX-99C-118C, the $T_{50}$ was 58° C., as compared to 51° C. for the natural xylanase TrX. This represented an increase in the thermostability, as measured by the "$T_{50}$", by about 7° C. through the introduction of the 99C/118C mutations.

The thermostability of modified xylanases containing the 99C/118C mutations in combination with additional mutations was also tested and compared with TrX-10H-27M-29L. As shown in FIG. 17, both TrX-10H-11D-27M-29L-40R-58R-75A-99C-105H-118C-125A-129E-131N and TrX-10H-11D-27M-29L-40R-58R-75A-99C-105H-118C-125A-129E exhibit superior thermostability relative to TrX-10H-27M-29L.

In summary, improved thermophilic, alkalophilic and/or thermostable mutant xylanases of the invention comprise cysteine residues at positions 99 and 118. The modified xylanase may further comprise one or more than one of the following amino acid substitutions:

(i) a substituted amino acid at position 58 such as a basic amino acid, including, but not limited to, Arg;
(ii) a substituted amino acid at position 40, including, but not limited to, an amino acid selected from Arg, Cys, Phe, His and Tyr;
(iii) amino acid substitutions at positions 10, 27 and 29, such as a basic substituted amino acid at position 10, including, but not limited to, His; a hydrophobic substituted amino acid at position 27, including, but not limited to, Met; and a hydrophobic substituted amino acid at position 29, including, but not limited to, Leu; and
(iv) any combination of the mutations set out in (i) to (iii).

In addition, the modified xylanase described above may further comprise one or more than one of the following amino acid substitutions:
(v) substitutions at positions 75 and 125 such as non-polar substituted amino acids, including, but not limited to, Ala or Gly; an amino acid substitution at position 105 such as a substituted basic amino acid, including, but not limited to, His, Arg or Lys; and/or an amino acid substitution at position 129 such as a substituted acidic amino acid including, but not limited to, Asp or Glu;
(vi) an amino acid substitution at position 52, including, but not limited to, Cys;
(vii) an amino acid substitution at position 11, such as an acidic amino acid, including, but not limited to, Asp;
(viii) an amino acid substitution at position 144 and/or 161, including, but not limited to, a basic amino acid such as Arg;
(ix) an amino acid substitution at position 131 to an Asn; and
(x) any combination of the mutations described in (v) to (viii).

Non-limiting examples of xylanase mutants comprising a 99C/118C disulfide bond in combination with the amino acid substitutions listed above are given in Table 2.

It is also within the scope of the invention to introduce one or more than one of the amino acid substitutions of (v) to (x) into a modified xylanase comprising a 99C/118C mutation and which does not contain the mutations set out in (i) to (iv). Furthermore, the modified xylanase may comprise amino acid substitutions not listed above in combination with the 99C/118C mutations. In addition, the 99C/118C mutations may also be introduced into any of the xylanase mutants described in U.S. Pat. No. 5,759,840, WO 03/046169, WO 01/92487 or WO 2005/093072, which are incorporated herein by reference.

It will also be appreciated that if one of the two positions, 99 or 118, already has a Cys residue, the creation of a 99C/118C disulfide bond could also be produced by a substitution of an amino acid at only one of positions 99 or 118 to Cys. Thus, the present invention relates to a modified xylanase comprising cysteine residues at positions 99 and 118 to form a 99C/118C disulfide bond, the xylanase produced by substitution of an amino acid at position 99, 118 or both positions 99 and 118 with a cysteine.

There are natural examples of *Aspergillus* xylanases with cysteine residues at positions that correspond to positions 99 and 118 of *Trichoderma reesei* xylanase II, for example *A. niger*, var. *awamori*; *A. kawachii* XynC; *A. tubigensis* (FIG. 1). However, like the natural TrX, the *Aspergillus* xylanases can only function at low temperature (Fushinobu et al., 1998) and acidic pH (Krengel and Dijkstra, 1996), and are only stable up to 40° C. (Ito et al., 1992, Biosci. Biotechnol. Biochem. 56:906-912). Therefore, the existence of cysteine residues at positions 99 and 118 in these mesophilic *Aspergillus* xylanases does not suggest that the creation of a disulfide bond in a xylanase will enhance its activity at high temperatures. Furthermore, these *Aspergillus* xylanases can only function at acidic pH values, with an acidic optimum pH of around 2-3 (Krengel and Dijkstra, 1996; Fushinobu et al., 1998, Esteves et al., 2004; Hakulinen et al., 2003). It therefore does not suggest that the creation of a similar disulfide bond in another acidophilic xylanase, including, but not limited to, TrX will enhance its activity at higher pH. Moreover, disulfide mutations are seldom observed to contribute to the alkalophilicity of an enzyme.

Therefore, the modified xylanase of the present invention may be derived from a Family 11 xylanase, including but not limited to a *Trichoderma reesei* xylanase. The modified xylanase preferably is not native *Aspergillus* xylanase. However, the *Aspergillus* xylanase, comprising naturally occurring cysteine residues at positions 99 and 118 (TrXII numbering) may be used to derive a modified xylanase comprising additional mutations as described herein in order to enhance the properties of thermophilicity and alkalophilicity of the *Aspergillus* xylanase.

Furthermore, a computational procedure called MODIP (Sowdhamini et al., 1989; Dani et al., 2003), which was established to aid in the design of a disulfide bridge to stabilise protein, has predicted that any stabilizing disulfide bond must enclose a loop, i.e., the number of residues between the two cysteines, of 25 amino acid residues or more. Another related study has also concluded that there is little stabilization if the loop length is smaller than 25 residues. The 99C/118C disulfide bond of the present invention, with a loop of 19 residues, is considerably smaller than the predicted minimum of 25 residues for a stabilising disulfide bond. The smallest loop of any stabilizing disulfide bond reported in a Family 11 xylanase is a 2/28 disulfide bond with a loop length of 26 resides, created at the N-terminus of TrX (Fenel et al., 2004). This 2/28 disulfide bond did not enhance xylanase activity at higher pH range.

The above description is not intended to limit the claimed invention in any manner. Furthermore, the discussed combination of features might not be absolutely necessary for the inventive solution.

The present invention will be further illustrated in the following examples. However, it is to be understood that these examples are for illustrative purposes only and should not be used to limit the scope of the present invention in any manner.

EXAMPLES

The construction of variant xylanases in the examples required the use of a precursor plasmid which contained only a partial xylanase gene (Table 4). The precursor plasmid is incapable of expressing a xylanase. Synthesis of the precursor plasmid has been described previously.

TABLE 4

| Plasmid containing a partial xylanase gene for the construction of new mutant xylanases | |
|---|---|
| Precursor plasmid[a] | Mutations |
| pTrX(1-113)[a] | (114-C terminus) sequence deleted |

[a]WO 01/92487 (Sung)

The new variant xylanases constructed in the following examples were also compared to various selected known mutant xylanases. The plasmids which expressed these previously described mutant xylanases are described in Table 5.

TABLE 5

Xylanase-expressing plasmids reported in the art

| Expressing plasmid[a,b or c] | Mutations |
|---|---|
| pTrX-118C[a] | TrX: Y118C |
| pTrX-HML[b] | TrX: N10H, Y27M and N29L |
| pTrX-HML-75A-105H-125A-129E[c] | TrX: N10H, Y27M, N29L, S75A, L105H, Q125A and I129E |
| pTrX-HML-75A-105H-125A-129E-144R-161R[a] | TrX: N10H, Y27M, N29L, S75A, L105H, Q125A, I129E, H144R and Q161R |
| pTrX-HDML-75A-105H-118C-125A-129E-144R-161R[a] | TrX: N10H, N11D, Y27M, N29L, S75A, L105H, Y118C, Q125A, I129E, H144R and Q161R |

[a]WO 03/046169 (Sung)
[b]U.S. Pat. No. 5,759,840 (Sung et al.)
[c]WO 01/92487 (Sung)

Example 1

Construction of *Trichoderma reesei* Mutant Xylanases

Basic recombinant DNA methods like plasmid preparation, restriction enzyme digestion, polymerase chain reaction, oligonucleotide phosphorylation, ligation, transformation and DNA hybridization were performed according to well-established protocols familiar to those skilled in the art (e.g. Sung et al., 1986), or as recommended by the manufacturer of the enzymes or kit. The buffers for many enzymes were supplied as part of a kit or made according to the manufacturer's instructions. Restriction enzymes, T4 polynucleotide kinase and T4 DNA ligase were purchased from New England BioLabs Ltd, Mississauga, Ontario. The GeneAmp PCR reagent kit was purchased from Perkin-Elmer. A precursor plasmid, pXYbc, which is a pUC type plasmid with a *Bacillus circulans* xylanase gene inserted, has previously been prepared and published (Sung et al., 1993; Campbell et al., U.S. Pat. No. 5,405,769). A commonly used *E. coli* strain, HB101 (Clonetech Lab, Palo Alto, Calif.), was used as a transformation and expression host for all gene constructs. Birchwood xylan and Remazol Brilliant Blue R-D-Xylan were purchased from Sigma (St. Louis, Mo.). Hydroxybenzoic acid hydrazide (HBAH) was purchased from Aldrich. Oligonucleotides were prepared with an APPLIED BIOSYSTEM DNA synthesizer (model 380B). All xylanase enzymatic assays were performed in a covered circulating water bath (Haake type F 4391) and maintained within a temperature range of ±0.1° C.

1.1 Construction of Precursor Plasmid pTrX Harbouring Synthetic TrX (SEQ ID NO:40)

The precursor plasmid pTrX for mutations disclosed below has been described (Sung et al., 1995). This plasmid was derived from a pUC119 plasmid with a synthetic nucleotide sequence encoding a *Trichoderma reesei* xylanase (TrX; FIG. 2). Expression of this xylanase and other mutant xylanases subsequently described are under the control of the lac Z promoter of the pUC plasmid. The total assembly of the *Trichoderma* xylanase gene required two stages, initially involving ligation of the 92-190 region, then followed by the 1-92 region (TrX numbering). The protocol for the construction of this gene is routine and identical to the standard published procedure for many other genes. The protocol requires enzymatic phosphorylation of overlapping synthetic oligonucleotides which encodes a xylanase. This is followed by their ligation into an appropriately cut plasmid.

For the construction of TrX (92-190), the following ten overlapping oligonucleotides (see FIG. 2) were designed:

| XyTv-101, | SEQ ID NO:30; |
|---|---|
| XyTv-102, | SEQ ID NO:31; |
| TrX-103, | SEQ ID NO:32; |
| XyTv-104, | SEQ ID NO:33; |
| XyTv-105, | SEQ ID NO:34; |
| XyTv-106, | SEQ ID NO:39; |
| XyTv-107, | SEQ ID NO:38; |
| TrX-108, | SEQ ID NO:37; |
| XyTv-109, and | SEQ ID NO:36; |
| XyTv-110, | SEQ ID NO:35. |

These mutants were designed with a codon usage frequency imitating that of *E. coli*. The SalI and BglII cohesive ends of two terminal oligonucleotides enabled the enzymatic ligation of the ten fragments into the linearized plasmid pXYbc. The ten oligonucleotides (50 pmol, 1 μL for each) encoding the TrX(92-190) region of *Trichoderma* xylanase were phosphorylated in a mixture containing 10× standard kinase buffer (0.4 μL), 1 mM ATP (4 μL), T4 DNA kinase (5 units) and water (3 μL). Phosphorylation reactions were carried out for 1 hour at 37° C. The solutions were then combined and heated to 70° C. for 10 minutes. After being cooled slowly to room temperature, the combined solutions were added to a mixture of 4 mM ATP (3.5 μL), SalI/BglII linearized plasmid pXYbc (0.1 pmol), and T4 DNA ligase (3.5 μL) and incubated at 12° C. for 20 h. Aliquots of the ligation mixture were used to transform *E. coil* HB101 on YT plates (8 g yeast extract, 5 g bacto-tryptone, 5 g NaCl, 15 g of agar in 1 L of water) containing ampicillin (100 mg/L).

For the preparation of a hybridization probe, one of the oligonucleotides, for example, XyTv-110 (10 pmol, 1 μL) was phosphorylated with $^{32}$P-ATP (10 pmol, 3 μL) using T4 DNA kinase (1 μL), 10× kinase buffer (1 μL), and water (4 μL) at 37° C. for 1 h.

Transformants were selected randomly for hybridization analysis. Colonies were grown on YT plates with ampicillin overnight and transferred onto nylon filters. They were then denatured with 0.5 N NaOH-1.5 M NaCl (10 minutes) and neutralized with 0.5 N Tris-HCl (pH 7.0)-1.5 M NaCl (10 minutes). After ultraviolet irradiation at 254 nm for 8 minutes, the filters were washed with 6×SSC-0.05% Triton X-100 for 30 minutes. Cell debris was scraped off completely. After another 30 minutes in fresh solution, duplicate filters were transferred individually into separate mixtures of 6×SSC-1% dextran sulphate-0.05% TritonX-100-1×Denhardt's hybridization fluid. The $^{32}$P-labelled probe was added to the filter. After 16 h at 45° C., the filter was washed twice with 6×SSC-0.05% TritonX-100 at room temperature for 5 minutes and then at 65° C. for 30 minutes. Positively hybridized clones with the intermediate plasmid pBcX-TrX were identified by auto-radiographic analysis.

The above protocol, involving enzymatic phosphorylation of synthetic overlapping oligonucleotides and ligation into a linearized plasmid, was employed in the assembly of the TrX(1-92) region and in the cassette mutagenesis for the subsequent generation of other mutant xylanases described in this invention.

For the assembly of the TrX(1-92; TrX numbering) region to complete the full-length *Trichoderma reesei* xylanase II gene (TrX), the intermediate plasmid pBcX-TrX was linearized by NheI and KpnI endonucleases to release the DNA insert for BcX(1-83). With NheI and KpnI cohesive ends, eight overlapping oligonucleotides:

TrX-1,      SEQ ID NO:22;
    XyTv-2,     SEQ ID NO:23;
    TrX-3,      SEQ ID NO:24;
    XyTv-4,     SEQ ID NO:25;

the plasmid into *E. coli* HB101 competent cells, (iv) identification of mutant transformants via hybridization with the labelled oligonucleotide, and (v) confirmation of the mutation through dideoxy nucleotide sequencing.

1.2 Construction of Plasmid pOmp-TrX Harbouring the Secretion Leader Sequence of the Outer Membrane Protein A (SEQ ID NOs:41 and 42)

Following the experimental protocol of 1.1, the oligonucleotides Omp-TX-1, -2, -3 and -4, which encode the secretion leader sequence of the *E. coli* outer membrane protein A and the reconstructed TrX(1-7) region, were ligated to the NheI/PinAI-cut plasmid pTrX. The resulting plasmid pOmp-TrX can produce the functional xylanase via expression and secretion.

```
                             Omp-TX-1
[OmpA    2   3   4   5   6   7   8   9   10  11  12   13  14

K   K   T   A   I   A   I   A   V   A   L    A   G

5'-CT AGC AAG AAG ACA GCA ATA GCA ATC GCT GTG GCA TTA G|CC GGC

G TTC TTC TGT CGT TAT CGT TAG|CGA CAC CGT AAT C GG CCG

NheI         Omp-TX-4                 Omp-TX-3

OmpTX2                    TrX sequence 15 16 17  18  19  20 21] [1   2    3   4   5   6   7
  F  A  T   V   A   Q  A   Q    T   I   Q   P   G   T
TTT GCG ACC GTT GCT CAG GCC CAG ACC ATA CAA CCA GGA A         (SEQ ID NO: 41)

AAA CGC TGG CAA CGA GTC CGG GTC TGG TAT GTT GGT CCT TGG CC    (SEQ ID NO: 42)
                                                    PinAI
```

-continued
    XyTv-5,     SEQ ID NO:29;
    TrX-6,      SEQ ID NO:28;
    XyTv-7,     SEQ ID NO:27;
    and
    TrX-8,      SEQ ID NO:26;

encoding the TrX(1-91) sequence were ligated into the linearized plasmid pBcX-TrX (FIG. 2) via the protocol described above. The new plasmid pTrX, therefore, harbored a synthetic TrX gene (SEQ ID NO:40).

All mutant xylanase genes described below were constructed via the method of cassette mutagenesis. The protocol for cassette mutagenesis was identical to that described for gene assembly described above. Generally, cassette mutagenesis involved (i) enzymatic phosphorylation of overlapping synthetic oligonucleotides, (ii) ligation of synthetic oligonucleotides with a linearized plasmid, (iii) transformation of 1.3 Construction of the Precursor Plasmid pOmp-TrX(1-113)

Plasmid pOmp-TrX-(1-113) comprises the amino acid sequence 1-113 of TrX and cannot express an active xylanase. Such transformants were confirmed by the absence of a clearing zone or halo around the transformant colonies on blue xylan plates.

The plasmid was constructed via (i) the removal of the TrX(114-190) coding sequence of plasmid pOmp-TrX through cutting with restriction enzymes BamHI and BglII, (ii) ligation of the identical cohesive ends of the linearized plasmid, (iii) transformation into the *E. coli* HB101 competent cells followed by plating on YT plate (containing 5 g yeast extract, 3 g bacto-tryptone, 5 g NaCl, 15 g of agar in 1 L of water, 1 g Remazol Brilliant Blue R-D-xylan) and ampicillin (100 mg/L), (iv) identification of the mutant transformants through the loss of xylanase activity (absence of a clearing zone or halo around the colonies on the blue xylan plate overnight at 40° C.), and (v) confirmation of the mutation through dideoxy nucleotide sequencing. The protocol for each of these steps was similar to that for gene assembly described above.

1.4 Construction of the Precursor pTrx-HML

The construction of this precursor plasmid pTrX-HML has been described in detail in U.S. Pat. No. 5,759,840 (see Example 1N, herein incorporated by reference; plasmid termed pNI-TX13). TrX-HML comprises the native TrX xylanase, along with three mutations at N10H (Asn at position 10 is replaced with His), Y27M and N29L. The first thirty amino acids of the sequence comprising N10H, Y27M and N29L are shown below.

```
TrX                                 1   2   3   4   5   6   7   8
amino acid                          Q   T   I   Q   P   G   T   G
5'-CT AGC TAA GGA GG CTG CAG ATG CAA ACA ATA CAA CCA GGA ACC GGT
     3'-G ATT CCT CC GAC GTC TAC GTT TGT TAT GTT GGT CCT TGG CCA
    Nhe I                                                   PinAI 9  10  11  12  13  14  15  16  17  18  19  20  21  22  23  24
 Y   H   N   G   Y   F   Y   S   Y   W   N   D   G   H   G   G
TAC CAC AAC GGT TAC TTT TAC AGC TAT TGG AAC GAT GGC CAT GGA GGC

ATG GTG TTG CCA ATG AAA ATG TCG ATA ACC TTG CTA CCG GTA CCT CCG 25  26  27  28  29  30
 V   T   M   T   L   G
GTC ACA ATG ACT CTG GGG                                              (SEQ ID NO: 43)

CAG TGT TAC TGA GAC CCC                                              (SEQ ID NO: 44)
```

1.5 Construction of the Precursor Plasmids pOmp-TrX-HML(1-113) and pOmp-TrX-HDML(1-113)

Plasmids pOmp-TrX-HML(1-113) and pOmp-TrX-HDML(1-113) comprise the amino acid sequence 1-113 of TrX and cannot express an active xylanase. Such transformants are confirmed by the absence of a clearing zone or halo around the transformant colonies on blue xylan plates.

In the construction of plasmids pOmp-TrX-HML(1-113), PCR was used to generate a DNA fragment encoding (8-C terminus) region with the PCR primers TX-10H-1 (SEQ NO:45) and TX-CI, and template pTrX-HML (Table 5). Cutting of the PCR product with restriction enzymes PinAI and BamHI yielded the (8-113) sequence.

In the construction of the plasmid pOmp-TrX-HDML(1-113), PCR was repeated with the primer TX-10H11D-1 (SEQ NO:46, which has been described in WO 03/046169), replacing the TX-10H-1, to generate the (8-C terminus) sequence. Cutting of the PCR product with the restriction enzymes, PinAI and BamHI, yielded the (8-113) sequence.

```
                     TX-10H-1 (SEQ ID NO: 45)
         6   7   8   9  10  11  12  13  14  15  16  17  18
         G   T   G   Y   H   N   G   Y   F   Y   S   Y   W
    5'-GGA ACC GGT TAC GAG AAC GGT TAC TTT TAC AGC TAT TGG
            PinAI

TX-10H11D-1 (SEQ ID NO: 46)
         6   7   8   9  10  11  12  13  14  15  16  17  18
         G   T   G   Y   H   D   G   Y   F   Y   S   Y   W
    5'-GGA ACC GGT TAC CAC GAC GGT TAC TTT TAC AGC TAT TGG
            PinAI

Reverse PCR primer TX-C1 comprised:
                       TX-C1 (SEQ ID NO: 47)
        183 184 185 186 187 188 189 190 ter
         G   S   A   S   I   T   V   S
        CCA AGG CGA TCA TAA TGT CAC TCG ATT TCT AGA ACT TCG AAC CC-5'
                                            BqlI    HindIII
```

The appropriate PCR template, pTRx-HML (Table 5), primers and the restriction enzymes to cut the end of the PCR products are listed below (Table 6).

TABLE 6

| PCR product | PCR upstream primer | PCR reverse primer | PCR template | Restriction enzymes for PCR product |
|---|---|---|---|---|
| (a) | TX-10H-1 | TX-C1 | pTrX-HML | PinAI/BamHI |
| (b) | TX-10H11D-1 | TX-C1 | pTrX-HML | PinAI/BamHI |

The cut PCR products (a) and (b) (Table 6) were ligated into a PinAI/BglII-linearized plasmid pOmp-TrX (described in 1.2) to generate plasmids pOmp-TrX-HML(1-113) and pOmp-TrX-HDML(1-113), respectively.

Subsequent steps involved (i) transformation into the *E. Coli* HB101 competent cells, followed by plating on a YT plate (containing 5 g yeast extract, 3 g bacto-tryptone, 5 g NaCl, 15 g of agar in 1 L of water, 1 g Remazol Brilliant Blue R-D-xylan) and ampicillin (100 mg/L), (ii) identification of the mutant transformants through the loss of xylanase activity (absence of a clearing zone or halo around the colonies on the blue xylan plate overnight at 40° C.), and (iii) confirmation of the mutation through dideoxy nucleotide sequencing. The protocol for each of these steps was similar to that for the construction of plasmid pOmp-TrX(1-113) described in 1.3.

1.6 Construction of Plasmid pTrX-58R

The pTrX-58R plasmid, with the additional mutation K58R compared to the precursor plasmid pTrX, were prepared.

PCR was used to generate a DNA fragment encoding the (54-190) region with the K58R mutation. The PCR primer with the K58R mutation (in bold type) is shown below.

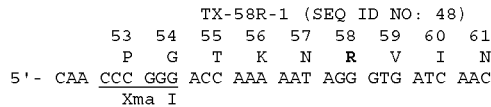

With the appropriate PCR template pTrX (Table 5), the primers and the restriction enzymes to cut the ends of the PCR products are listed below (Table 7).

TABLE 7

| PCR product | PCR upstream primer | PCR reverse primer | Restriction enzymes for PCR product |
|---|---|---|---|
| (c) | TX-58R-1 | TX-C1 | XmaI/HindIII |

The cut PCR product (c) (Table 7) was ligated into a XmaI/HindIII-linearized plasmid pTrX(1-113) to generate the plasmid pTrX-58R.

1.7 Construction of Plasmids pTrX-40H and pTrX-40R

Plasmids pTrX-40H and pTrX-40R, with the additional mutations S40H and S40R compared to the precursor plasmid pTrX, were prepared.

PCR was used to generate a DNA fragment encoding (39-190) region with the S40H and S40R mutation. The PCR primers with the 40H and 40R mutations (in bold type) are shown below.

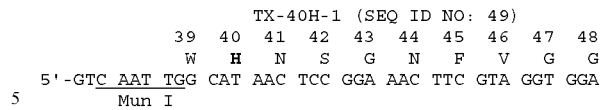

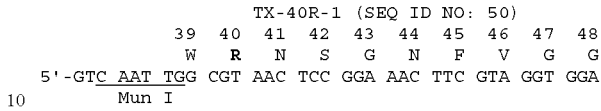

With the appropriate PCR template pTrX, the primers and the restriction enzymes to cut the ends of the PCR products are listed below (Table 8).

TABLE 8

| PCR product | PCR upstream primer | PCR reverse primer | Restriction enzymes for PCR product |
|---|---|---|---|
| (d) | TX-40H-1 | TX-C1 | MunI/HindIII |
| (e) | TX-40R-1 | TX-C1 | MunI/HindIII |

The cut PCR products (d) and (e) (Table 8) were ligated into a MunI/HindIII-linearized plasmid pTrX(1-113) to generate the plasmids pTrX-40H and pTrX-40R.

1.8 Construction of Plasmid pTrX-99C

Plasmid pTrX-99C, with the additional mutation S99C not present in the precursor plasmid pTrX, was prepared.

PCR was used to generate a DNA fragment encoding (95-190) region with the S99C mutation.

The PCR primers with mutation (in bold type) is shown below.

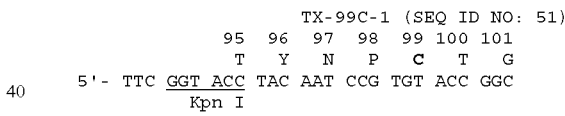

With the appropriate PCR template, pTrX, the primers and the restriction enzymes to cut the ends of the PCR products are listed below (Table 9).

TABLE 9

| PCR product | PCR upstream primer | PCR reverse primer | Restriction enzymes for PCR product |
|---|---|---|---|
| (f) | TX-99C-1 | TX-C1 | KpnI/HindIII |

The cut PCR product (f) (Table 9) was ligated into a KpnI/HindIII-linearized plasmid pTrX(1-113) (Table 4) to generate the plasmid pTrX-99C.

1.9 Construction of Plasmid pOmpTrX-99C-118C

The pOmpTrX-99C-118C plasmid, with the additional mutations S99C and Y118C and a secretion leading signal sequence not present in the precursor plasmid pTrX, was prepared.

PCR was used to generate a DNA fragment encoding (95-190) region with the S99C and Y118C mutation.

With the appropriate PCR template pTrX-118C (see Table 5, WO 03/046169), the primers and the restriction enzymes to cut the ends of the PCR products are listed below (Table 10).

TABLE 10

| PCR product | PCR upstream primer | PCR reverse primer | Restriction enzymes for PCR product |
|---|---|---|---|
| (g) | TX-99C-1 | TX-C1 | KpnI/HindIII |

The cut PCR product (g) (Table 10) was ligated into a KpnI/HindIII-linearized plasmid pOmpTrX(1-113), (described in 1.3) to generate the plasmid pOmpTrX-99C-118C.

1.10 Construction of Plasmid pOmpTrX-58R-99C-118C

The pOmpTrX-58R-99C-118C plasmid, with additional mutations of K58R, S99C and Y118C, and a secretion leading signal sequence, compared to the precursor plasmid pTrX, was prepared.

PCR was used to generate a DNA fragment encoding the (54-190) region with the K58R, S99C and Y118C mutations.

With the appropriate PCR template, pOmpTrX-99C-118C (described in 1.9), the primers and the restriction enzymes to cut the ends of the PCR products are listed below (Table 11).

TABLE 11

| PCR product | PCR upstream primer | PCR reverse primer | Restriction enzymes for PCR product |
|---|---|---|---|
| (h) | TX-58R-1 | TX-C1 | XmaI/HindIII |

The cut PCR product (h) (Table 11) was ligated into a XmaI/HindIII-linearized plasmid pOmpTrX(1-113) (described in 1.3) to generate the plasmid pOmpTrX-58R-99C-118C.

1.11 Construction of Plasmids pOmpTrX-40H-99C-118C and pOmpTrX-40H-58R-99C-118C The pOmpTrX-40H-99C-118C plasmid, with additional mutations of S40H, S99C and Y118C, and a secretion leading signal sequence, compared to the precursor plasmid pTrX, was prepared. The pOmpTrX-40H-58R-99C-118C plasmid has an extra mutation of K58R PCR was used to generate DNA fragments encoding the (39-190) region with the S40H, S99C and Y118C mutations, with or without the mutation K58R, as determined by the appropriate plasmid templates.

For the creation of pOmpTrX-40H-99C-118C with the appropriate PCR template, pOmpTrX-99C-118C (described in 1.9), the primers and the restriction enzymes to cut the ends of the PCR products are listed below (Table 12).

TABLE 12

| PCR product | PCR upstream primer | PCR reverse primer | Restriction enzymes for PCR product |
|---|---|---|---|
| (i) | TX-40H-1 | TX-C1 | MunI/HindIII |

For the creation of pOmpTrX-40H-58R-99C-118C, with the appropriate PCR template pOmpTrX-58R-99C-118C (described in 1.10), the primers and the restriction enzymes to cut the ends of the PCR products are listed below (Table 13).

TABLE 13

| PCR product | PCR upstream primer | PCR reverse primer | Restriction enzymes for PCR product |
|---|---|---|---|
| (j) | TX-40H-1 | TX-C1 | MunI/HindIII |

The cut PCR product (i) (Table 12) and (j) (Table 13) were ligated into a MunI/HindIII-linearized plasmid, pOmpTrX(1-113) (described in 1.3), to generate plasmids pOmpTrX-40H-99C-118C and pOmpTrX-40H-58R-99C-118C, respectively.

1.12 Construction of Plasmid pOmpTrX-HML-40R-58R-99C-118C

The pOmpTrX-HML-40R-58R-99C-118C plasmid, with additional mutations of S40R, K58R, S99C and Y118C, and a secretion leading signal sequence, compared to the precursor plasmid pTrX-HML, was produced.

With the appropriate PCR template, pOmpTrX-58R-99C-118C (described in 1.10), the primers and the restriction enzymes to cut the ends of the PCR products are listed below (Table 14).

TABLE 14

| PCR product | PCR upstream primer | PCR reverse primer | Restriction enzymes for PCR product |
|---|---|---|---|
| (k) | TX-40R-1 | TX-C1 | MunI/HindIII |

The cut PCR product (k) (Table 14) was ligated into a MunI/HindIII-linearized plasmid pOmpTrX-HML(1-113) (described in 1.5) to generate plasmid pOmpTrX-10H-27M-29L-40R-58R-99C-118C.

1.13 Construction of Plasmids pOmpTrX-10H-27M-29L-40R-58R-75A-99C-118C

The pOmpTrX-10H-27M-29L-40R-58R-75A-99C-118C plasmid, with the additional mutation S75A compared to the plasmid pOmpTrX-10H-27M-29L-40R-58R-99C-118C, was prepared. The PCR primers with mutation S75A (in bold type) are shown below.

TX-75A-1 (SEQ ID NO: 52)

```
        69  70  71  72  73  74  75  76  77  78  79  80  81

N   G   N   S   Y   L   A   V   Y   G   W   S   R

5'-T GGG AAT TCA TAC TTA GCC GTC TAT GGC TGG TCT AG
     EcoRI
```

With the appropriate PCR templates pOmpTrX-10H-27M-29L-40R-58R-99C-118C (described in 1.12) for both PCR products (l) and (m), the primers and the restriction enzymes to cut the ends of the PCR products are listed below (Table 15).

TABLE 15

| PCR product | PCR upstream primer | PCR reverse primer | Restriction enzymes for PCR product |
|---|---|---|---|
| (l) | TX-10H-1 | TX-C1 | PinAI/EcoRI |
| (m) | TX-75A-1 | TX-C1 | EcoRI/HindIII |

The cut PCR products (l and m) (Table 15) were ligated into a PinAI/HindIII-linearized plasmid, pOmpTrX(1-113) (described in 1.3), to generate the plasmid pOmpTrX-10H-27M-29L-40R-58R-75A-99C-118C.

1.14 Construction of Plasmid pOmpTrX-10H-27M-29L-75A-99C-105H-118C-125A-129E

The pOmpTrX-10H-27M-29L-75A-99C-105H-118C-125A-129E plasmid, was prepared via two PCR reactions, involving the following primers:

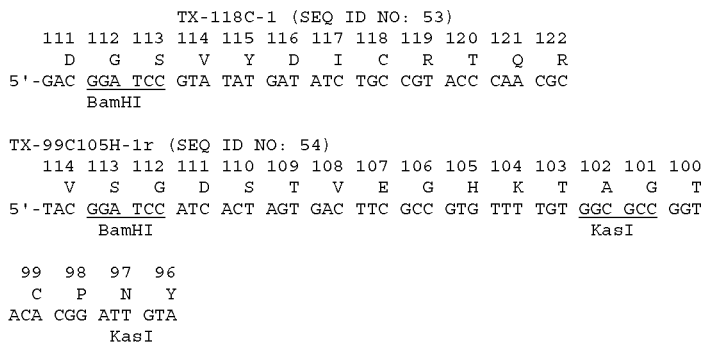

With plasmid pTrX-10H-27M-29L-75A-105H-125A-129E as a PCR template (Table 5), one PCR product (n) was synthesized to encode the (8-112) sequence, and another PCR product (o) to encode the (113-190) region.

With the appropriate PCR template plasmid pTrX-10H-27M-29L-75A-105H-125A-129E (Table 5), the primers and the restriction enzymes to cut the ends of the PCR products are listed below (Table 16).

TABLE 16

| PCR product | PCR upstream primer | PCR reverse primer | Restriction enzymes for PCR product |
|---|---|---|---|
| (n) | TX-10H-1 | TX-99C-105H-1r | PinAI/BamHI |
| (o) | TX-118C-1 | TX-C1 | BamHI/HindIII |

The cut PCR products (n and o) (Table 16) were ligated into a PinAI/HindIII-linearized plasmid, pOmpTrX-HML(1-113) (described in 1.5) to generate plasmid pOmpTrX-10H-27M-29L-75A-99C-105H-118C-125A-129E.

1.15 Construction of Plasmid pOmpTrX-10H-27M-29L-58R-75A-99C-105H-118C-125A-129E The pOmpTrX-10H-27M-29L-58R-75A-99C-105H-118C-125A-129E plasmid, with an additional mutation K58R compared to the precursor plasmid pOmpTrX-10H-27M-29L-75A-99C-105H-118C-125A-129E (in 1.14), was created.

With the appropriate PCR template pOmpTrX-10H-27M-29L-75A-99C-105H-118C-125A-129E (in 1.14), the primers and the restriction enzymes to cut the ends of the PCR products are listed below (Table 17).

TABLE 17

| PCR product | PCR upstream primer | PCR reverse primer | Restriction enzymes for PCR product |
|---|---|---|---|
| (p) | TX-58R-1 | TX-C1 | XmaI/HindIII |

The cut PCR product (p) (Table 17) was ligated into a XmaI/HindIII-linearized plasmid pOmpTrX-HML(1-113) (described in 1.5) to generate the plasmid pOmpTrX-10H-27M-29L-58R-75A-99C-105H-118C-125A-129E.

1.16 Construction of Plasmid pOmpTrX-10H-11D-27M-29L-58R-75A-99C-105H-118C-125A-129E The pOmpTrX-10H-11D-27M-29L-58R-75A-99C-105H-118C-125A-129E plasmid, with an extra N11D mutation, was prepared using the same strategy as for the plasmid pOmpTrX-10H-27M-29L-58R-75A-99C-105H-118C-125A-129E in 1.15.

The cut PCR product (p) (Table 17) which was prepared for the construction of pOmpTrX-10H-27M-29L-58R-75A-99C-105H-118C-125A-129E (in 1.15), was ligated into a XmaI/HindIII-linearized plasmid pOmpTrX-HDML(1-113) (described in 1.5) to generate the plasmid pOmpTrX-10H-11D-27M-29L-58R-75A-99C-105H-118C-125A-129E.

1.17 Construction of Plasmid pOmp-TrX-10H-11D-27M-29L-40X-58R-75A-99C-105H-118C-125A-129E, where X is C, F, H, R, Y, A or T The plasmids pOmpTrX-10H-11D-27M-29L-40X-58R-75A-99C-105H-118C-125A-129E, where X is C, F, H, R, Y, A or T, were prepared using the same strategy, with a PCR primer harbouring the appropriate mutation:

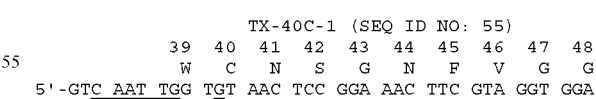
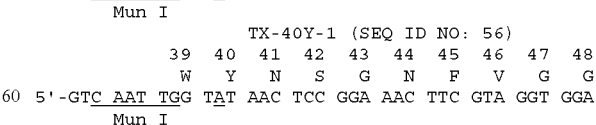
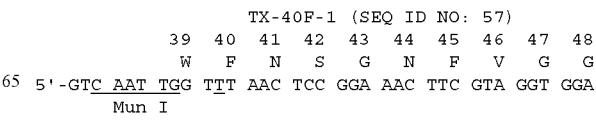

-continued

```
                    TX-40T-1 (SEQ ID NO: 58)
        39  40  41  42  43  44  45  46  47  48
         W   T   N   S   G   N   F   V   G   G
5'-GTC AAT TGG ACT AAC TCC GGA AAC TTC GTA GGT GGA
   Mun I

TX-40A-1 (SEQ ID NO: 59)
        39  40  41  42  43  44  45  46  47  48
         W   A   N   S   G   N   F   V   G   G
5'-GTC AAT TGG GCT AAC TCC GGA AAC TTC GTA GGT GGA
   Mun I
```

TX-40H-1 and TX-40R-1 have been described in 1.8.

With the appropriate PCR template plasmid pOmpTrX-10H-27M-29L-58R-75A-99C-105H-118C-125A-129E (described in 1.15), the primers and the restriction enzymes to cut the ends of the PCR products are listed below (Table 18).

TABLE 18

| PCR product | PCR upstream primer | PCR reverse primer | Restriction enzymes for PCR product |
|---|---|---|---|
| (q) | TX-40H-1 | TX-C1 | MunI/HindIII |
| (r) | TX-40R-1 | TX-C1 | MunI/HindIII |
| (s) | TX-40C-1 | TX-C1 | MunI/HindIII |
| (t) | TX-40F-1 | TX-C1 | MunI/HindIII |
| (u) | TX-40Y-1 | TX-C1 | MunI/HindIII |
| (v) | TX-40T-1 | TX-C1 | MunI/HindIII |
| (w) | TX-40A-1 | TX-C1 | MunI/HindIII |

The cut PCR products (q, r, s, t, u, v and w) (Table 18) were ligated into a MunI/HindIII-linearized plasmid pOmpTrX-HDML(1-113) (described in 1.5) to generate the plasmids pOmp-TrX-10H-11D-27M-29L-40H-58R-75A-99C-105H-118C-125A-129E, pOmp-TrX-10H-11D-27M-29L-40R-58R-75A-99C-105H-118C-125A-129E, pOmp-TrX-10H-11D-27M-29L-40C-58R-75A-99C-105H-118C-125A-129E, pOmp-TrX-10H-11D-27M-29L-40Y-58R-75A-99C-105H-118C-125A-129E, pOmp-TrX-10H-11D-27M-29L-40F-58R-75A-99C-105H-118C-125A-129E, pOmp-TrX-10H-11D-27M-29L-40T-58R-75A-99C-105H-118C-125A-129E and pOmp-TrX-10H-11D-27M-29L-40A-58R-75A-99C-105H-118C-125A-129E, respectively.

1.18 Construction of Plasmid pOmp-TrX-10H-11D-27M-29L-40H-52C-58R-75A-99C-105H-118C-125A-129E The pOmpTrX-10H-11D-27M-29L-40H-52C-58R-75A-99C-105H-118C-125A129E plasmid was prepared via ligation of two PCR sequences, namely a PinAI/XmaI-linearized (8-53) fragment and an XmaI/HindIII-linearized (54-190) fragment. The former sequence was synthesized via a PCR with the following primer harbouring the mutation Q52C:

```
                    TX-52C-1r (SEQ ID NO: 60)
        54  53  52  51  50  49  48  47  46  45  44
         G   P   C   W   G   K   G   G   V   F   N
5'-GT CCC GGG ACA CCA ACC TTT TCC ACC TAC GAA GT
      XmaI
```

With the appropriate PCR template plasmid, pOmpTrX-10H-11D-27M-29L-40H-58R-75A-99C-105H-118C-125A-129E (described in 1.17), the primers and the restriction enzymes to cut the ends of the PCR products are listed below (Table 19).

TABLE 19

| PCR product | PCR upstream primer | PCR reverse primer | Restriction enzymes for PCR product |
|---|---|---|---|
| (x) | TX-10H11D-1 | TX-52C-1r | PinAI/XmaI |

The (54-190) fragment has already been prepared as the XmaI/HindIII-cut PCR product (p) of Table 17 in 1.15.

Ligation of the PinAI/XmaI-cut (8-53) fragment (x) (Table 19) and the XmaI/HindIII-cut (54-190) fragment (p) (Table 17) into the PinAI/HindIII-linearized precursor plasmid pOmp-TrX-(1-113) (described in 1.3), yielded the new plasmid pOmpTrX-10H-11D-27M-29L-40H-52C-58R-75A-99C-105H-118C-125A-129E.

1.19 Construction of Plasmid pOmp-TrX-10H-11D-27M-29L-40R-58R-75A-99C-105H-118C-125A-129E-144R-161R Plasmid pOmp-TrX-10H-11D-27M-29L-40R-58R-75A-99C-105H-118C-125A-129E-144R-161R was created, which differed from plasmid pOmp-TrX-10H-11D-27M-29L-40H-52C-58R-75A-99C-105H-118C-125A-129E of 1.18 by two mutations: H144R and Q161R.

It was synthesized via a ligation of two appropriately cut PCR products. The first insert encoding region (39-112) was generated through a MunI/BamHI-cutting of the PCR product (r) already described in Table 18 of 1.17.

The second insert encoding the (113-190) region was prepared via PCR with the appropriate PCR template plasmid pTrX-10H-27M-29L-75A105H-125A129E-144R-161R (WO 03/046169). The primers and the restriction enzymes to cut the ends of the PCR products are listed below (Table 20).

TABLE 20

| PCR product | PCR upstream primer | PCR reverse primer | Restriction enzymes for PCR product |
|---|---|---|---|
| (y) | TX-118C-1 | TX-C1 | BamHI/HindIII |

The two appropriately cut PCR products (y) (Table 20) and the MunI/BamHI-cut (r) were ligated into a MunI/HindIII-linearized plasmid pOmpTrX-HDML(1-113) (described in 1.5) to generate the plasmid pOmp-TrX-10H-11D-27M-29L-40R-58R-75A-99C-105H-118C-125A-129E-144R-161R.

Example 2

Characterization of Mutant Xylanases 2.1 Production of Xylanases

The culture conditions comprised a 5 mL culture of overnight innoculant in 2YT medium (16 g bacto-tryptone, 10 g yeast extract, 5 g NaCl, 1 L of water) containing ampicillin (100 mg/L). The culture was spread out on a tray (32×25 cm) evenly covered by 0.5 L of solidified YT agar (8 g yeast extract, 5 g bacto-tryptone, 5 g NaCl, 15 g of agar in 1 L of water) containing ampicillin (100 mg/L). The cultures were grown at 37° C. After 40 hr, the cells (2 g) were harvested for extraction of xylanase.

2.2 Purification of Mutant Xylanases

The harvested cells were put into a tube for a freeze-thaw extraction of xylanase. The procedure comprised a freezing period in a dry ice/ethanol bath for 5 minutes, followed by water/ice bath for 10 minutes. The procedure was repeated thrice. The cells were extracted with buffer (5 mL, 100 mM Na citrate, pH 5.5). Centrifuging at 8000×g for 30 minutes yielded a supernatant containing xylanase. The xylanase solution was adjusted to pH 5.2. The precipitate which appeared was removed through centrifuging at the same condition. The supernatant was heated at a range of 50-60° C., depending of the thermostability of the recombinant xylanase, for 30 minutes to convert more undesirable bacterial proteins into precipitate, which was removed by centrifugation.

Prior to column chromatography, the supernatant was adjusted to pH 4.6 by acetic acid and centrifuged to remove any precipitate. The subsequent method for column chromatography was identical for all mutant xylanases.

Following acidification and centrifugation, the xylanase sample was pumped onto a 50 mL bed volume, CM-sepharose fast flow, cation exchange column (Pharmacia Biotech, Uppsala), equilibrated in 10 mM sodium acetate (pH 5.1). The xylanase was eluted with a 250 mL linear gradient (0 to 0.6 M NaCl in 10 mM sodium acetate, pH 5.1) at a flow rate of 1 mL/min. The xylanases elute at 150 to 200 mL of the gradient. Aliquots from the collected fractions are examined by SDS-PAGE, and those fractions having most of the xylanase present were pooled. The purified xylanase was quantified by spectrophotometry at 280 nm using an extinction coefficient between 54,600 and 53,400 $M^{-1}$, for most mutant TrX xylanases. A typical purification from 10 g of cells yielded 25 mg of xylanase.

2.3 Standard Assay for the Measurement of Enzymatic Activity

The quantitative assay determined the number of reducing sugar ends generated from soluble xylan. The substrate for this assay was the fraction of birchwood xylan which dissolved in water from a 5% suspension of birchwood xylan (Sigma Chemical Co.). After removing the insoluble fraction, the supernatant was freeze-dried and stored in a dessicator. The measurement of activity was performed as follows. Reaction mixtures containing 100 µL of 30 mg/mL xylan previously diluted in assay buffer (50 mM sodium citrate, pH 5.5 or the pH optimum of the tested xylanase), 150 µL assay buffer, and 50 µL of enzyme (15 µg/mL) diluted in assay buffer were incubated at 40° C. At various time intervals, 50 µL portions were removed and the reaction stopped by diluting in 1 mL of 5 mM NaOH. The amount of reducing sugars was determined with the hydroxybenzoic acid hydrazide reagent (HBAH) (Lever, 1972, which is incorporated herein by reference).

Example 3

Thermophilicity of Mutant Xylanases

Thermophilicity was examined to test the effect of different temperatures on the enzymatic hydrolysis of soluble xylan by different mutant xylanases.

The assay procedure was similar to the standard assay with changes in the incubation temperature and time. The xylanases (15 µg/mL) and soluble birchwood xylan substrate, in 50 mM sodium citrate buffer of pH 5.5, or stated otherwise, were mixed and incubated in a circulating water bath at different temperatures. After a 30-minute incubation, the amount of reducing sugars released from xylan was determined by HBAH analysis and was calculated as a relative activity, with the value at 40° C. or the temperature optimum representing 100%.

The effect of temperature on the hydrolysis of xylan by *Trichoderma reesei* xylanase TrX with individual mutations like S40H, K58R, S99C or Y118C is shown in FIG. 3.

The mutation S40H in xylanase TrX-40H showed a moderately improved enzymatic activity at higher temperature as compared to TrX (FIG. 3). In the case of the xylanase TrX-58R, the mutation K58R by itself showed no improvement over TrX (FIG. 3), as already reported by Turunen et al. (2002).

The increase of thermophilicity by the single mutation Y118C as in xylanase TrX-118C (FIG. 3) has been described in the art (WO 03/046169), but the possibility of a disulfide bond created through introduction of a cysteine-118 has never been studied. This mutation can potentially form a disulfide linkage with a cysteine replacement at residue 99.

Initially the single mutation S99C was tested in the form of a mutant xylanase, TrX-99C (FIG. 3), with no apparent improvement of enzymatic activity at higher temperature, therefore demonstrating this mutation has no effect on the temperature/activity profile of TrX. However, when the S99C and Y118C mutations were incorporated in the form of the double mutant xylanase TrX-99C-118C there was a dramatic enhancement of thermophilicity (FIG. 3), even when compared to the single mutant TrX-118C. The improvement of the temperature optima of the double mutant TrX-99C-118C over the natural xylanase, TrX, is about 7° C. (FIG. 4). In addition to higher temperature optimum (FIG. 4), TrX-99C-118C also exhibited higher optimal activity than TrX at their respective temperature optima (FIG. 3).

The additive effect of the mutations S40R and K58R on the 99C/118C mutations to increase enzymatic activity at higher temperatures was confirmed in the form of the mutant xylanases TrX-58R-99C-118C, TrX-40H-99C-118C and TrX-40H-58R-99C-118C (FIGS. 3 and 4). Although the mutation K58R by itself failed to improve the activity of xylanase at higher temperature (FIG. 3), it has demonstrated a positive effect in combination with other mutations S40H and S99C/Y118C.

The new mutations are compatible with other advantageous mutations which have been described in the art. This was demonstrated below in the creation of xylanase variants with higher temperature optimum and optimal activity.

The mutations of N10H, Y27M and N29L to increase the thermophilicity of TrX, in the form of the mutant TrX-10H-27M-29L (or TrX-HML), have been described (U.S. Pat. No. 5,759,840). Variant xylanases TrX-10H-27M-29L-40R-58R-99C-118C (FIG. 5) and TrX-10H-27M-29L-40R-58R-75A-99C-118C were created with further improved thermophilicity (FIG. 5).

The mutations of N10H, Y27M, N29L, S75A, L105H, Q125A and I129E to increase the thermophilicity of TrX, in the form of the mutant TrX-10H-27M-29L-75A-105H-125A-129E (TrX-HML-AHAE), are described in WO 01/92487. Variant xylanases TrX-10H-27M-29L-75A-99C-105H-118C-125A-129E (FIGS. 6 and 8) and TrX-10H-27M-29L-58R-75A-99C-105H-118C-125A-129E (FIG. 6) were created, both with further enhanced thermophilicity.

The mutation of N11D is described in WO 03/046169. Addition of this mutation created a variant TrX-10H-11D-27M-29L-58R-75A-99C-105H-118C-125A-129E (FIGS. 6, 7 and 8). Variations of mutation 40 (S40C, A, F, H, R, Y or T) were introduced into this variant to create the new mutants TrX-10H-11D-27M-29L-40X-58R-75A-99C-105H-118C-125A-129E (where X=C, A, F, H, R, Y and T). As indicated in the study above, introduction of mutations S40H or S40R moderately improved the relative activity at higher temperature as compared to the host enzyme (FIGS. 6, 7 and 8). Furthermore, other mutations S40C, S40F and S40Y exhibited the same enhancing effect (FIG. 7), while S40T and S40A showed no such enhancing effect on the temperature/activity profile (FIG. 7).

Another mutation, Q52C, was introduced into TrX-10H-11D-27M-29L-40H-58R-75A-99C-105H-118C-125A-129E. The mutant xylanase TrX-10H-11D-27M-29L-40H-52C-58R-75A-99C-105H-118C-125A-129E was able to retain significant relative activity at higher temperatures of 80 and 85° C. (FIGS. 6, 7 and 8).

The mutations H144R and Q161R (described in WO 03/046169) have been shown to increase the pH optimum of the xylanase TrX-10H-11D-27M-29L-75A-105H-118C-125A-129E-144R-161R (or TrX-10H-11D-27M-29L-AH-118C-AE-RR). Addition of mutations S40R, K58R and S99C allowed the mutant xylanase TrX-10H-11D-27M-29L-40R-58R-75A-99C-105H-118C-125A-129E-144R-161R to retain greater activity at higher temperatures of 80 and 85° C. (FIG. 9).

The above results demonstrate that the enhancing effect of the mutations S40X (X=C, F, H, R or Y), Q52C, K58R, and the disulfide S99C/Y118C mutation on the thermophilicity of the mutant xylanase are not only complementary or additive to each other, but also to other mutations disclosed in the art (U.S. Pat. No. 5,759,840, WO 01/92487 and WO 03/046169).

Example 4

Alkalophilicity of Mutant Xylanases

The alkalophilicity of genetically modified xylanases was examined to test the effect that different pH conditions had on the enzymatic hydrolysis of soluble birchwood xylan by mutant xylanases. The assay procedure was similar to the standard assay with changes in the incubation temperature and time. Aliquots of genetically modified xylanases (15 µg/mL) and soluble xylan substrate in 50 mM sodium citrate buffers which varied between pH 4-8 were incubated together at 55° or 65° C. as stated. Following 30 minute incubations, the amount of reducing sugars released from the xylan substrate was determined by HBAH analysis and the enzymatic activity as a function of pH was calculated for a variety of mutant xylanases with the maximal activity taken as 100%.

The effect of the S99C/Y118C mutations on the pH/activity profile of xylanase was investigated. The new disulfide mutant TrX-99-C118C maintained greater activity at high pH values of 6.5-7.5 (FIG. 10), as compared to the natural xylanase TrX. The pH range to maintain 80% optimal activity is 4.8-7.0 for the disulfide mutant xylanase TrX-99C-118C and only 4.8-6.0 for natural xylanase TrX, indicating a broader effective pH range for the former.

Xylanases with the individual mutations TrX-99C and TrX-118C were also compared to TrX-99C-118C and the natural xylanase TrX. Both TrX-99C and TrX-118C have the same pH/activity profile as TrX (FIG. 10). This confirmed that the improvement of activity at higher pH is a result of the combination of S99C and Y118C mutations to form the disulfide bond, and not the single Cys mutations.

The effect of the mutations S40X (X is H or R), K58R and the disulfide S99C/Y118C on the pH/activity profile of xylanase was also studied in two groups of mutants constructed above.

The first group was derived from the mutant TrX-10H-27M-29L-75A-105H-125A-129E (or TrX-HML-AH-AE) and are described in WO 01/92487. Derivatives like TrX-10H-27M-29L-75A-99C-105H-118C-125A-129E, TrX-10H-27M-29L-58R-75A-99C-105H-118C-125A-129E, TrX-10H-11D-27M-29L-58R-75A-99C-105H-118C-125A-129E and TrX-10H-11D-27M-29L-40H-58R-75A-99C-105H-118C-125A-129E showed greater activity at higher pH (FIG. 11), as compared to the parent TrX-10H-27M-29L-75A-105H-125A-129E. However, the greatest improvement of activity by TrX-10H-27M-29L-75A-99C-105H-118C-125A-129E, over the parent xylanase TrX-10H-27M-29L-75A-105H-125A-129E, was via the addition of the 99C/118C disulfide. The other mutant xylanases in this series (FIG. 11), with mutations S40H or K58, showed no additional effect on the activity of xylanase.

The enhancing effect of the S99C/Y118C mutations was further demonstrated in the second group based on TrX-10H-27M-29L-75A-105H-125A129E-144R-161R, a xylanase containing two mutations H144R and Q161R which has been shown to successfully increase the pH optimum of xylanase (see WO 01/92487). This construct, TrX-10H-11D-27M-29L-40R-58R-75A-99C-105H-118C-125A-129E-144R-161R, exhibited greater activity at higher pH than its parent TrX-10H-27M-29L-75A-105H-125A-129E-144R-161R (FIG. 12). It also outperformed another xylanase TrX-10H-11D-27M-29L-75A-105H-116G-118C-125A-129E-144R-161R (FIG. 12), a mutant xylanase which previously showed the most improved pH/activity profile among mutant xylanases in WO 03/046169.

Example 5

Thermostability of Mutant Xylanases

The tolerance of xylanase to incubation at different temperatures in the absence of substrate was investigated. The xylanase (150 µg/mL) in assay buffer (50 mM sodium citrate, pH 5.0) was incubated for 30 minutes at 48, 52, 56 and 60° C. Aliquots were cooled to room temperature (around 20° C.) and the residual enzymatic activity of the samples was determined via the HBAH assay at 55° C. for 30 minutes. The residual enzymatic activity at 48° C. was normalized to 100%.

The disulfide mutant, TrX-99C-118C, retained greater residual activity than the natural xylanase TrX (FIG. 13) after incubation at higher temperatures. The $T_{50}$ was 58° C. for the disulfide xylanase, as compared to a $T_{50}$ of 51° C. for the natural xylanase TrX (FIG. 13), which is an increase in the thermostability of the former by about 7° C.

While the present invention has described mutant xylanases which exhibit improved thermophilicity, alkalophilicity and thermostability, and the benefits associated with these enzymes in the production of paper pulp, these mutant xylanases may also be of use in other industrial processes, for example, but not limited to, the washing of precision devices and semiconductors. Furthermore, by virtue their increased thermophilicity and thermostability the mutant xylanases may be used in chemical processes that employ small quantities of denaturants or detergents or in the presence of solvents, for example, but not limited to, small amounts of apolar solvents, such as, but not limited to, hexane, dioxanes, carbon tetrachloride, benzene, ethers, chloroform, acetic acid and methylene chloride, and polar solvents, such as, but not limited to, acetone, alcohols, dimethylformamide, acetonitrile, sulfolane, dimethylsulfoxide and water.

Example 6

Isolation of *Trichoderma reesei* Genomic DNA and Construction of *T. reesei* Genomic Libraries

*Trichoderma reesei* strain M2C38 is a proprietary strain of Iogen Corporation derived from *Trichoderma reesei* RutC30 (ATCC #56765; Montenecourt and Eveleigh, 1979), which was, in turn, derived from *Trichoderma reesei* Qm6A (ATCC #13631; Mandels and Reese, 1957). It is well understood by those skilled in the art that the procedures described herein, the genetic constructs from these strains, and the expression of the genetic constructs in these strains are applicable to all *Trichoderma* strains derived from Qm6A.

To isolate genomic DNA, 50 mL of Potato Dextrose Broth (Difco) was inoculated with *T. reesei* spores collected from a Potato Dextrose Agar plate with a sterile inoculation loop. The cultures were shaken at 200 rpm for 2-3 days at 28° C. The mycelia was filtered onto a GFA glass microfibre filter (Whatman) and washed with cold, deionized water. The fungal cakes were frozen in liquid nitrogen crushed into a powder with a pre-chilled mortar and pestle; 0.5 g of powdered biomass were resuspended in 5 mL of 100 mM Tris, 50 mM EDTA, pH 7.5 plus 1% sodium dodecyl sulphate (SDS). The lysate was centrifuged (5000 g for 20 min, 4° C.) to pellet cell debris. The supernatant was extracted with 1 volume buffer (10 mM Tris, 1 mM EDTA, pH 8.0) saturated phenol followed by extraction with 1 volume of buffer-saturated phenol:chloroform:isoamyl alcohol (25:24:1) in order to remove soluble proteins. DNA was precipitated from the solution by adding 0.1 volumes of 3 M sodium acetate, pH 5.2 and 2.5 volumes of cold 95% ethanol. After incubating for at least 1 h at −20° C., the DNA was pelleted by centrifugation (5000 g for 20 min, 4° C.), rinsed with 10 mL 70% ethanol, air-dried and resuspended in 1 mL 10 mM Tris, 1 mM EDTA, pH 8.0. RNA was digested by the addition of Ribonuclease A (Boehringer Mannheim) added to a final concentration of 0.1 mg/mL and incubation at 37° C. for 1 hour. Sequential extractions with 1 volume of buffer-saturated phenol and 1 volume of buffer-saturated phenol:chloroform:isoamyl alcohol (25:24:1) was used to remove the ribonuclease from the DNA solution. The DNA was again precipitated with 0.1 volumes of 3 M sodium acetate, pH 5.2 and 2.5 volumes of cold 95% ethanol, pelleted by centrifugation, rinsed with 70% ethanol, air-dried and resuspended in 50 µL of 10 mM Tris, 1 mM EDTA, pH 8.0. The concentration of DNA was determined by measuring the absorbance of the solution at 260 nm (p. Cl in Sambrook et al., 1989, *Molecular Cloning: A Laboratory Manual*, 2nd. ed. Cold Spring Harbor, N.Y.: Cold Spring Harbor Laboratory Press).

Two plasmid libraries and one phage library were constructed using genomic DNA isolated from *T. reesei* strain M2C38. The plasmid libraries were constructed in the vector pUC119 (Viera and Messing, 1987) as follows: 10 µg genomic DNA was digested for 20 hrs at 37° C. in a 100 µL volume with 2 units/µg of BamH1 or EcoR1 restriction enzymes. The digested DNA was fractionated on a 0.75% agarose gel run in 0.04 M Tris-acetate, 1 mM EDTA and stained with ethidium bromide. Gel slices corresponding to the sizes of the genes of interest (based on published information and Southern blots) were excised and subjected to electro-elution to recover the DNA fragments (Sambrook et al., pp. 6.28-6.29). These enriched fractions of DNA were ligated into pUC119 in order to create gene libraries in ligation reactions containing 20-50 µg/mL DNA in a 2:1 molar ratio of vector:insert DNA, 1 mM ATP and 5 units T4 DNA ligase in a total volume of 10-15 mL at 4° C. for 16 h. *Escherichia coli* strain HB101 was electroporated with the ligation reactions using the Cell Porator System (Gibco/BRL) following the manufacturer's protocol and transformants selected on LB agar containing 70 µg/mL ampicillin.

The phage library was constructed in the lambda vector λDASH (Stratagene, Inc.) as follows: genomic DNA (3 µg) was digested with 2, 1, 0.5 and 0.5 units/µg BamHI for 1 hour at 37° C. to generate fragments 9-23 kB in size. The DNA from each digest was purified by extraction with 1 volume Tris-staturated phenol:choroform:isoamyl alcohol (25:24:1), followed by precipitation with 10 µL 3 M sodium acetate, pH 5.2 and 250 µl 195% ethanol (−20° C.). The digested DNA was pelleted by microcentrifugation, rinsed with 0.5 mL cold 70% ethanol, air-dried and resuspended in 10 µL sterile, deionized water. Enrichment of DNA fragments 9-23 kB in size was confirmed by agarose gel electrophoresis (0.8% agarose in 0.04 M Tris-acetate, 1 mM EDTA). Digested DNA (0.4 µg) was ligated to 1 µg λDASH arms predigested with BamHI (Stratagene) in a reaction containing 2 units T4 DNA ligase and 1 mM ATP in a total volume of 5 µl at 4° C. overnight. The ligation mix was packaged into phage particles using the GigaPackg® II Gold packaging extracts (Stratagene) following the manufacturer's protocol. The library was titred using the *E. coli* host strain XL1-Blue MRA (P2) and found to contain $3 \times 10^5$ independent clones.

Example 7

Isolation of Genomic Clones from *T. reesei* M2C38 Libraries

7.1 Cloning the Cellobiohydrolase I (cbh1) and Cellobiohydrolase II (cbh2) Genes from pUC119 Libraries

*E. coli* HB101 transformants harboring cbh1 or cbh2 clones from recombinant pUC119-BamH1 or -EcoRI libraries were identified by colony lift hybridization: $1-3 \times 10^4$ colonies were transferred onto HyBond™ nylon membranes (Amersham); membranes were placed colony-side up onto blotting paper (VWR 238) saturated with 0.5 M NaOH, 1 M NaCl for 5 min to lyse the bacterial cells and denature the DNA; the membranes were then neutralized by placing them colony-side up onto blotting paper (VWR 238) saturated with 1.5 M Tris, pH 7.5 plus 1 M NaCl for 5 min; the membranes were allowed to air-dry for 30 min and the DNA was then fixed to the membranes by baking at 80° C. for 2 h.

$^{32}$P-labelled probes were prepared by PCR amplification of short (0.7-1.5 kB) fragments of the cbh1 and cbh2 coding regions from the enriched pool of BamH1 or EcoR1 fragments, respectively, in a labelling reaction containing 10-50 ng target DNA, 0.2 mM each d(GCT)TP, 0.5 µM dATP, 20-40 µCi α-$^{32}$P-dATP, 10 pmole oligonucleotide primers and 0.5 units Taq polymerase in a total volume of 20 µL. The reaction was subjected to 6-7 cycles of amplification (95° C., 2 min, 56° C., 1.5 min; 70° C., 5 min). The amplified, $^{32}$P-labelled DNA was precipitated by the addition of 0.5 mL 10% (w/v) trichloroacetic acid and 0.5 mg yeast tRNA. The DNA was pelleted by microcentrifugation, washed twice with 1 mL 70% ethanol, air-dried and resuspended in 1 M Tris pH 7.5, 1 mM EDTA.

Nylon membranes onto which the recombinant pUC119 plasmids had been fixed were prehybridized in heat-sealed bags for 1 h at 60-65° C. in 1 M NaCl, 1% SDS, 50 mM Tris, 1 mM EDTA pH 7.5 with 100 µg/mL denatured sheared salmon sperm DNA. Hybridizations were performed in heat-sealed bags in the same buffer with only 50 µg/mL denatured sheared salmon sperm DNA and 5×10$^6$-5×10$^7$ cpm of denatured cbh1 or cbh2 probe for 16-20 h at 60-65° C. Membranes were washed once for 15 min with 1 M NaCl, 0.5% SDS at 60° C., twice for 15 min each with 0.3M NaCl, 0.5% SDS at 60° C. and once for 15 min with 0.03M NaCl, 0.5% SDS at 55° C. Membranes were again placed in heat-sealed bags and exposed to Kodak RP X-ray film to 16-48 h at −70° C. The X-ray film was developed following the manufacturer's protocols. Colonies giving strong or weak signals were picked and cultured in 2×YT media supplemented with 70 µg/mL ampicillin. Plasmid DNA was isolated from these cultures using the alkaline lysis method (Sambrook, et al., pp. 1.25-1.28) and analyzed by restriction digest, Southern hybridization (Sambrook, et al., pp. 9.38-9.44) and PCR analysis (Sambrook, et al., pp. 14.18-14, 19).

Clones carrying the cbh1 gene were identified by colony lift hybridization of the pUC119-BamH1 library with a 0.7 kb cbh1 probe prepared using oligonucleotide primers designed to amplify bp 597-1361 of the published cbh1 sequence (Shoemaker et al., 1983.). A cbh1 clone, pCOR132, was isolated containing a 5.7 kb BamH1 fragment corresponding to the promoter (4.7 kb) and 1 kb of the cbh1 structural gene (2.3 kb). From this, a 2.5 kb EcoR1 fragment containing the cbh1 promoter (2.1 kb) and 5' end of the cbh1 coding region (0.4 kb) was subcloned into pUC119 to generate pCB152. Clones carrying the cbh2 gene were identified by colony lift hybridization of the pUC119-EcoR1 library with a 1.5 kb cbh2 probe prepared using oligonucleotide primers designed to amplify bp 580-2114 of the published cbh2 sequence (Chen et al. 1987). A cbh2 clone, pZUK600 was isolated containing a 4.8 kb EcoR1 fragment corresponding to the promoter (600 bp), structural gene (2.3 kb) and terminator (1.9 kb).

7.2 Cloning cbh1 Terminator and Xylanase II (xln2) Gene from λDASH Libraries Digoxigen-11-dUTP labelled probes were prepared from PCR amplified coding regions of the cbh1 and xln2 genes by random prime labeling using the DIG Labeling and Detection kit (Boehringer Mannheim) and following the manufacturer's protocols. Genomic clones containing the cbh1 and xln2 genes were identified by plaque-lift hybridization of the λDASH library. For each gene of interest, 1×10$^4$ clones were transferred to Nytran® (Schleicher and Schull) nylon membranes. The phage particles were lysed and the phage DNA denatured by placing the membranes plaque-side up on blotting paper (VWR238) saturated with 0.5 M NaOH, 1 M NaCl for 5 min; the membranes were then neutralized by placing them plaque-side up onto blotting paper saturated with 1.5 M Tris, pH 7.5 plus 1 M NaCl for 5 min; the membranes were allowed to air-dry for 30 min and the DNA was then fixed to the membranes by baking at 80° C. for 2 h. The membranes were prehybridized in heat-sealed bags in a solution of 6×SSPE, 5×Denhardt's, 1% SDS plus 100 µg/mL denatured, sheared salmon sperm DNA at 65° C. for 2 h. The membranes were then hybrized in heat-sealed bags in the same solution containing 50 µg/mL denatured, sheared salmon sperm DNA and 0.5 µg of digoxigen-dUTP labelled probes at 65° C. overnight. The membranes were washed twice for 15 min in 2×SSPE, 0.1% SDS at RT, twice for 15 min in 0.2×SSPE, 0.1% SDS at 65° C. and once for 5 min in 2×SSPE. Positively hybridizing clones were identified by reaction with an anti-digoxigenin/alkaline phosphatase antibody conjugate, 5-bromo-4-chloro-3-indoyl phosphate and 4-nitro blue tetrazolium chloride (Boehringer Mannheim) following the manufacturer's protocol. Positively hybridizing clones were further purified by a second round of screening with the digoxigen-dUTP labelled probes.

Individual clones were isolated and the phage DNA purified as described in Sambrook et al. (1989) pp. 2.118-2.121 with the exception that the CsCl gradient step was replaced by extraction with 1 volume of phenol:choroform:isoamyl alcohol (25:24:1) and 1 volume of chloroform:isoamyl alcohol (24:1). The DNA was precipitated with 0.1 volumes of 3 M sodium acetate, pH 5.2 and 2.5 volumes cold 95% ethanol. The precipitated phage DNA was washed with 0.5 mL cold 70% ethanol, air-dried and resuspended in 50 µL 10 mM Tris, 1 mM EDTA pH 8.0. Restriction fragments containing the genes of interest were identified by restriction digests of the purified phage DNA and Southern blot hybridization (Sambrook, et al., pp. 9.38-9.44) using the same digoxigen-dUTP labelled probes used to screen the λDASH library. The membranes were hybridized and positively hybridizing fragments visualized by the same methods used for the plaque lifts. Once the desired restriction fragments from each λDASH clone were identified, the restriction digests were repeated, the fragments were resolved on a 0.8% agarose gel in TAE and the desired bands excised. The DNA was eluted from the gel slices using the Sephaglas B and Prep Kit (Pharmacia) following the manufacturer's protocol.

Clones carrying the cbh1 gene were identified by colony lift hybridization of the λDASH library (Example 7) with a cbh1 probe comprising bp 45-2220 of the published cbh1 sequence (Shoemaker et al.). A 1.8 kb BamH1 fragment containing the 3' end of the cbh1 coding region (0.5 kb) and the cbh1 terminator (1.3 kb) was isolated by restriction digestion of phage DNA purified from a λDASH cbh1 clone. This fragment was subcloned into the BamH1 site of the E. coli plasmid vector pUC119 to generate the plasmid pCB1Ta. Clones carrying the xln2 gene were identified by colony lift hybridization of the λDASH library (Example 7) with a xln2 probe comprising bp 100-783 of the published xln2 sequence (Saarelainen et al., 1993, Mol. Gen. Genet. 241:497-503). A 5.7 kb Kpn1 fragment containing the promoter (2.3 kb), coding region (0.8 kb) and terminator (2.6 kb) the xln2 gene was isolated by restriction digestion of phage DNA purified from a λDASH xln2 clone. This fragment was subcloned into the Kpn1 site of pUC119 to generate the plasmid pXYN2K-2.

Example 8

Construction of a Vector Directing the Expression of Modified FAMILY 11 Xylanases in *Trichoderma reesei*

A 2.4 kb fragment containing the promoter and secretion signal of the xln2 gene (bp −2150 to +195 where +1 indicates the ATG start codon and +193-195 represent codon 32) was amplified with Pwo polymerase from the genomic xln2 subclone pXYN2K-2 (Example 7) using a xln2-specific primer containing a PinA1 at bp 190-195 or codons 31 and 32) and the pUC reverse primer (Cat. No. 18432-013, Gibco/BRL) which anneals downstream of the Kpn1 site at the 5' end of the x/n2 gene. This xln2 PCR product was inserted as a blunt-ended fragment into the Sma1 site of the pUC119 polylinker in such an orientation that the BamHI site of the polylinker is 3' to the PinAI site; this generated the plasmid pUC/XynPSS (Pin). The same xln2 PCR product was reisolated from pUC/XynPSS(Pin) by digestion with EcoR1 (which was amplified as part of the pUC119 polylinker from pXYN2K-2) and BamH1 and inserted into the plasmid pBR322L (a derivative of pBR322 containing an Sph1-Not1-Sal1 adaptor between the original Sph1 and Sal1 sites at bp 565 and 650), also digested with EcoR1 and BamH1, to generate the plasmid pBR322LXP. To facilitate high level expression of the modified xylanases, a 1.3 kb HindIII fragment comprising bp −1400 to −121 of the xln2 promoter in pBR322LXP was replaced with a 1.2 kb HindIII fragment comprising bp −1399 to −204 of the cbh1 promoter which was isolated by HindIII digestion of pCOR132; this generated the plasmid pBR322LXC. Finally, the EcoR1 site of pBR322LXC was then blunted with Klenow and Spe1 linkers (Cat. No. 1086, New England Biolabs) were added to generate pBR322SpXC.

A fragment containing codons 1-190 of the xylanase gene containing the mutations N27H, Y27M, N29L was isolated from the plasmid pUC/HML (described in Example 9.1 below) by digestion with NheI and BamHI inserted into pCB219N-N digested with NheI and BamHI to generate pHML/C2ter. To make pCB219N-N, a cbh2 terminator fragment was amplified from the pZUK600 (described in Example 7, above) template using a primer homologous to bp 2226-2242 of the published 3' untranslated region of the cbh2 gene (Chen et al., 1987) containing a short polylinker comprising XbaI-NheI-BamHI-Sma1-Kpn1 sites at the 5' end and the pUC forward primer (Cat. No. 1224, New England Biolabs) which anneals upstream of the EcoR1 site at the 3' end of cbh2 in pZUK600. This fragment was digested at the engineered XbaI and EcoR1 sites and inserted into the corresponding sites of pUC119 to generate pCB219. An EcoR1-Not1 adaptor (Cat. No. 35310-010, Gibco/BRL) was inserted into the unique EcoR1 site of pCB219 to generate pCB219N. A 2.7 kb fragment comprising codons 9-190 of the HTX4 gene and the cbh2 terminator was isolated from pHTX4/C2ter by digestion with PinAI and NotI and inserted into pBR322SpXC digested with PinAI and NotI to generate the expression cassette pc/xHML-EC.

Example 9

Mutagenesis of *T. reesei* Xylanase II to Generate the Variant TRX-10H-11D-27M-29L-40R-58R-75A-99C-105H-118C-125A-129E-131N 9.1 Introduction of Mutations N10H, 27M, Y29L The synthetic DNA comprising codons 32-190 in pTrX-HML (Example 1.4) was replaced by the corresponding genomic fragment of *T. reesei* xln2, containing a 108 bp intron at codon 58, which was amplified using genomic *T. reesei* DNA as a template and introducing a unique PinAI site at codons 31 and 32 and a unique BamHI directly downstream of the TAG stop codon. This generates pUC/HML.

9.2 Introduction of Mutations 75A, 105H, 125A, 129E

A 3.2 kb SstI fragment containing the promoter regions, the xln2 gene, and part of the cbh2 terminator was isolated from pc/xHML-EC (Example 8) and cloned into the SstI site in the polylinker of the mutagenesis vector, pALTER®-1 (Promega). Four sequential rounds of mutagenesis were performed to alter specific amino acids using primers specifically designed to incorporate the desired mutations:

```
                                        (SEQ ID NO: 83)
S75A:   AGCTACCTCG CCGTGTACGG (SEQ ID NO: 84)
L105H:  CCACCAAGCA CGGCGAGGT (SEQ ID NO: 85)
S125A:  ACGCAGCGCG TCAACGCCCC GTCCATCATC GGC (SEQ ID NO: 86)
I129E:  AACGCCCCGT CCATCGAGGG CACCGCCACC TTT
```

(see WO 01/92487 and WO 03/046169; which are incorporated herein by reference, for associated methods); this generated the plasmid pALT-TrX-10H-27M-29L-75A-105H-125A-129E. The incorporation of all mutations was verified by DNA sequence analysis.

9.3 Introduction of Mutations K58R, S99C, Y118C

One round of mutagenesis was performed on the plasmid pALT-TrX-10H-27M-29L-75A-105H-125A-129E using the Promega Altered Sites® II in vitro Mutagenesis System and the primer sequences:

```
                                        (SEQ ID NO: 87)
K58R:   GGC ACC AAG AAC CGC TAA GAC TAC CTA (SEQ ID NO: 88)
S99C:   ACC TAC AAC CCG TGC ACG GGC GCC ACC (SEQ ID NO: 89)
Y118C:  C TAC GAC ATT TGC CGC ACG C
``` to introduce the K58R, S99C, and Y118C mutations and generate pALT-TrX-10H-27M-29L-58R-75A-99C-105H-118C-125A-129E. The incorporation of all mutations was verified by DNA sequence analysis.

9.4 Introduction of Mutations N11D, S40R

One round of mutagenesis was performed on the plasmid pALT-TrX-10H-27M-29L-58R-75A-99C-105H-118C-125A-129E using the Promega Altered Sites® II in vitro Mutagenesis System and the primer sequences:

```
                                        (SEQ ID NO: 90)
N11D:   GGT TAC CAC GAC GGT TAC T (SEQ ID NO: 91)
S40R:   TCC GTC AAC TGG CGC AAC TCG GGC AAC
``` to introduce the N11D and S40R mutations and generate pALT-TrX-10H-11D-27M-29L-40R-58R-75A-99C-105H-118C-125A-129E. The incorporation of all mutations was verified by DNA sequence analysis.

9.5 Introduction of Mutation T131N

One round of mutagenesis was performed on the plasmid pALT-TrX-10H-11D-27M-29L-40R-58R-75A-99C-105H-118C-125A-129E using the Promega Altered Sites® II in vitro Mutagenesis System and the primer sequence:

T131N: CCG TCC ATC GAG GGC AAC GCC ACC TTT TAC (SEQ ID NO: 92)

to introduce the T131N mutations and generate pALT-TRX-10H-11D-27M-29L-40R-58R-75A-99C-105H-118C-125A-129E-131N. The incorporation of the mutation was verified by DNA sequence analysis Example 10

Construction of a Vector Directing the Expression of TrX-10H-11D-27M-29L-40R-58R-75A-99C-105H-118C-125A-129E-131N in *Trichoderma reesei*

The 3640 bp SacI fragment containing the promoter regions, the modified xln2 gene and part of the cbh2 terminator from pALT-TRX-10H-11D-27M-29L-40R-58R-75A-99C-105H-118C-125A-129E-131N was cloned into the SacI site of a plasmid containing the remaining cbh2 terminator sequence in pSP72. This step generates the expression cassette containing plasmid pc/xTRX-10H-11D-27M-29L-40R-58R-75A-99C-105H-118C-125A-129E-131N-PSP. The selection cassette containing plasmid, pNCBgINSNB(r), was derived from a *N. crassa* pyr4 containing plasmid, pFB6 (Radford et al, 1985). A 3.2 kb BglII fragment from pFB6 containing the *N. crassa* pyr4 gene (GenBank accession M13448) as well as its promoter, terminator and some 5' UTR sequences was cloned into the BamHI site of pUC119 modified to contain NotI, SmaI, NheI and BglII sites in the polylinker (between EcoRI and SacI) to generate pNCBgI-NSNB(r). A 2238 bp KpnI fragment containing the entire *N. crassa* pyr4 coding region, promoter and terminator sequences was isolated from pNCBgI-NSNB(r) and cloned into the unique KpnI site of the expression cassette-containing plasmid to generate pc/xTRX-10H-11D-27M-29L-40R-58R-75A-99C-105H-118C-125A-129E-131N-TV.

Example 11

Transformation of the *Trichoderma reesei* M2C38

$5 \times 10^6$ spores of M2C38aux5 were plated onto sterile cellophane on Potato Dextrose agar supplemented with 5 mM uridine and are incubated for 20 hours at 30° C. to facilitate spore germination and mycelial growth. Cellophane discs with mycelia were transferred to 10 mL of a protoplasting solution containing 7.5 g/L Driselase and 125 units of protease free β-glucanase (InterSpex Products Inc., Cat. Nos. 0465-1 and 0410-3, respectively) in 50 mM potassium phosphate buffer, pH 6.5 containing 0.6 M ammonium sulfate (Buffer P). The mycelial mat was digested for 5 hours with shaking at 60 rpm. Protoplasts were separated from undigested mycelia by filtration through sterile No. 30 MIRACLOTH™ and collected into a sterile 50 mL round-bottom centrifuge tube and recovered by centrifugation at 1000-1500×g for 10 min at room temperature. Protoplasts were washed with 5 mL of Buffer P and centrifuged again at 1000-1500×g for 10 min at room temperature. Protoplasts were resuspended in 1 mL of STC buffer (1.2 M sorbitol, 10 mM $CaCl_2$, 10 mM Tris-HCL, pH 7.5). For transformation, 0.1 mL of resuspended protoplasts were combined with 10 μg of vector DNA and 25 μL of PEG solution (25% PEG 4000, 50 mM $CaCl_2$, 10 mM Tris-HCl, pH 7.5). After incubation in an ice water bath for 30 min, 1 mL of PEG solution was added and the mixture incubated for 5 min at room temperature. Transformation mix was diluted with 2 mL of 1.2 M sorbitol in PEG solution and the entire mix was added to 25 mL of molten MMSS agar media (see below) cooled to about 47° C. and the protoplast suspension poured over MMSS agar. Plates were incubated at 30° C. until colony growth was visible. Transformants were transferred to individual plates containing MM agar and allowed to sporulate. Spores were collected and plated at high dilution on MM agar to isolate homokaryon transformants, which were then plated onto PDA to allow for growth and sufficient sporulation to inoculate the screening cultures as described in Example 12 below.

Minimal medium (MM) agar contains the components set forth in Table 21.

TABLE 21

| Reagent | Per L |
| --- | --- |
| $KH_2PO_4$ | 10 g |
| $(NH_4)_2SO_4$ | 6 g |
| $Na_3Citrate \cdot 2H_2O$ | 3 g |
| $FeSO_4 \cdot 7H_2O$ | 5 mg |
| $MnSO_4 \cdot H_2O$ | 1.6 mg |
| $ZnSO_4 \cdot 7H_2O$ | 1.4 mg |
| $CaCl_2 \cdot 2H_2O$ | 2 mg |
| Agar | 20 g |
| 20% Glucose f.s. | 50 mL |
| 1 M $MgSO_4 \cdot 7H_2O$ f.s. | 4 mL |
| | pH to 5.5 |

MMSS agar contains the same components as MM agar plus 1.2 M sorbitol, 1 g/L YNB (Yeast Nitrogen Base w/o Amino Acids from DIFCO Cat. No. 291940) and 0.12 g/L amino acids (-Ura DO Supplement from BD Biosciences Cat. No. 630416).

Example 12

Detection of Thermophilic Xylanase Activity in *T. reesei* Culture Filtrates

The presence of thermophilic xylanase activity in culture filtrates of *T. reesei* transformants was determined by measuring the release of reducing sugars from a soluble wheat arabinoxylan substrate at 65° C. Specifically, 30 μL of an appropriate dilution of culture filtrate was pre-incubated at 65° C. for 5 min. Subsequently, 300 μL of a solution of 1.5% wheat arabinoxylan (Megazyme International) redissolved in pH 7.0 phosphate buffer containing 0.04% Tween, also pre-incubated at 65° C. for 5 min, was added to the enzyme sample in a microcentrifuge tube. The tubes were vortexed briefly to facilitate mixing and then the reaction was incubated at 65° C. for 20 min. The enzymatic hydrolysis reaction was stopped by the addition of 150 μL of the stopping solution containing 43.64 mM 2-hydroxy-3,5-dinitrobenzoic acid, 0.93 M sodium potassium tartrate, 0.4 M sodium hydroxide and 0.4 M potassium hydroxide. The resulting solution was then boiled for 10 minutes to facilitate reaction of the 2-hydroxy-3,5-dinitrobenzoic acid with the reducing sugars released from the arabinoxylan substrate by the enzyme. The tubes were cooled on ice for 5 minutes and then 1.5 mL of deionized water was added. The absorbance of the solution was measured at 530 nm. The amount of reducing sugar released by the thermophilic xylanases during the incubation was calculated from a standard curve of A530 measurements of several dilutions of a pure xylose solution reacted with the same stopping solution.

Example 13

Production of Modified Xylanases in Liquid Cultures

Individual colonies of *Trichoderma* were transferred to PDA plates for the propagation of each culture. Sporulation was necessary for the uniform inoculation micro-cultures which were used in testing the ability of the culture to produce the thermophilic xylanases and cellulase. The culture media is composed of the following:

TABLE 22

| Component | g/L |
|---|---|
| $(NH_4)_2SO_4$ | 12.7 |
| $KH_2PO_4$ | 8.00 |
| $MgSO_4 \cdot 7H_2O$ | 4.00 |
| $CaCl_2 \cdot 2H_2O$ | 1.02 |
| Corn Steeped Liquor | 5.00 |
| $CaCO_3$ | 20.00 |
| Carbon source** | 30-35 |
| Trace elements* | 2 mL/L |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.
**glucose, Solka floc, lactose, cellobiose, sophorose, corn syrup, or Avicel. The carbon source can be sterilized separately as an aqueous solution at pH 2 to 7 and added to the remaining media initially or through the course of the fermentation.

Individual transformants were grown in the above media in 1 mL cultures in 24-well micro-plates. The initial pH was 5.5 and the media sterilized by steam autoclave for 30 minutes at 121° C. prior to inoculation. For both native and transformed cells, spores were isolated from the PDA plates, suspended in water and $10^4$-$10^6$ spores per mL were used to inoculate each culture. The cultures were shaken at 500 rpm at a temperature of 30° C. for a period of 6 days. The biomass was separated from the filtrate containing the secreted protein by centrifugation at 12,000 rpm. The protein concentration was determined using the Bio-Rad Protein Assay (Cat. No. 500-0001). Xylanase activity was determined as described in Example 12. Strains expressing the highest xylanase activity and exhibiting high overall protein production were selected for growth in 30-liter pilot fermentations.

Example 14

Production of Xylanases in 30 L Fed-Batch Fermentations

*T. reesei* strains were grown on Potato Dextrose Agar at 28-30° C. until a confluent lawn of spores was obtained. Spores were collected and used to inoculate 750 mL of Berkeley media (10 g/L glucose, 1.4 g/L $(NH_4)_2SO_4$, 2.0 g/L $KH_2PO_4$, 0.31 g/L $MgSO_4 \cdot 7H_2O$, 0.53 g/L $CaCl_2$; 5.1 g/L dry corn steep, 5 mg/L $FeSO_4 \cdot 7H_2O$; 0.8 mg/L $MnSO_4 \cdot H_2O$, 0.7 mg/L $ZnSO_4 \cdot 7H_2O$) in a 2 L baffled flask. After 3 days of growth at 28° C. and 150 rpm, this culture was used to inoculate 23 L of fermentation medium with the following initial composition: 31 g/L glucose, 4.4 g/L $(NH_4)_2SO_4$, 2.77 g/L $KH_2PO_4$, 1.4 g/L $MgSO_4 \cdot 7H_2O$, 0.37 g/L $CaCl_2$, 12 g/L dry corn steep, 3.5 mg/L $FeSO_4 \cdot 7H_2O$, 1.12 mg/L $MnSO_4 \cdot H_2O$, 0.98 g/L $ZnSO_4 \cdot 7H_2O$. A fed-batch aerobic fermentation using one or more of the inducing carbohydrate sources listed in Example 13 was run for 6 days at pH 4.5 and 28° C. in a 30 L New Brunswick Microferm fermentor. After 6 days, the culture was filtered over Harborlite and the culture filtrate adjusted to pH 4.5 and preserved with 0.5% benzoate to prevent microbial growth.

The protein concentration in daily fermentor samples was determined using the Bio-Rad Protein Assay (Cat. No. 500-0001). Xylanase activity was determined as described in Example 12.

The expression of TrX-10H-11D-27M-29L-40R-58R-75A-99C-105H-118C-125A-129E-131N and TrX-10H-11D-27M-29L-40R-58R-75A-99C-105H-118C-125A-129E from transformed *T. reesei* strains (biomass and xylanase activity) in 30 L fermentations is presented in Table 23 below.

TABLE 23

| Strain | Enzyme | Protein (mg/mL) | Xylanase Activity (XU/g) |
|---|---|---|---|
| P345A | TrX-10H-11D-27M-29L-40R-58R-75A-99C-105H-118C-125A-129E-131N | 63-88 | 12021 |
| P275H | TrX-10H-11D-27M-29L-40R-58R-75A-99C-105H-118C-125A-129E | 69 | 7145 |

Example 15

Alkalophilicity and Thermophilicity of the Modified Xylanases TrX-10H-11D-27M-29L-40R-58R-75A-99C-105H-118C-125A-129E-131N and TrX-10H-11D-27M-29L-40R-58R-75A-99C-105H-118C-125A-129E The pH and temperature profiles of the modified xylanases TrX-10H-11D-27M-29L-40R-58R-75A-99C-105H-118C-125A-129E-131N and TrX-10H-11D-27M-29L-40R-58R-75A-99C-105H-118C-125A-129E made by *Trichoderma* strains P345A and P275H are shown in FIGS. 14, 15, and 16. The data was generated by measuring reducing sugar release from wheat arabinoxylan, hardwood pulp, or softwood pulp with variable conditions.

FIG. 14 shows that the temperature optimum of TrX-10H-11D-27M-29L-40R-58R-75A-99C-105H-118C-125A-129E-131N is slightly higher than the optimum of TrX-10H-11D-27M-29L-40R-58R-75A-99C-105H-118C-125A-129E. Temperature profiles for each enzyme were generated on a 1% wheat arabinoxylan (Megazyme International) substrate at pH 7 for 60 minutes.

FIGS. 15 and 16 show that the thermophilic/alkalophilic enzyme TrX-10H-11D-27M-29L-40R-58R-75A-99C-105H-118C-125A-129E-131N from P345A has a slightly broader pH optimum range on both hardwood and softwood pulp than TrX-10H-11D-27M-29L-40R-58R-75A-99C-105H-118C-125A-129E from strain P275H. The pH profiles were generated at 70° C. for 60 minutes on 10% consistency pulp. Enzyme TrX-10H-11D-27M-29L-40R-58R-75A-99C-105H-118C-125A-129E-131N was added at a dose of 400 mL/t of pulp and enzyme TrX-10H-11D-27M-29L-40R-58R-75A-99C-105H-118C-125A-129E was added at a dose of 800 mL/t of pulp.

Example 16

Thermostability Testing of the Modified Xylanases TrX-10H-11D-27M-29L-40R-58R-75A-99C-105H-118C-125A-129E-131N, TrX-10H-11D-27M-29L-40R-58R-75A-99C-105H-118C-125A-129E and TrX-10H-27M-29L The tolerance of modified xylanases TrX-10H-11D-27M-29L-40R-58R-75A-99C-105H-118C-125A-129E-131N, TrX-10H-11D-27M-29L-40R-58R-75A-99C-105H-118C-125A-129E and TrX-10H-27M-29L to incubation at different temperatures in the absence of substrate was investigated. The modified xylanases were diluted 10- to 50-fold in 200 mM bis-tris propane buffer at pH 8.0 and incubated for 30 min at 50° C., 60° C., 70° C. and 80° C. At the end of the incubation period, the residual enzyme activity was determined as described in Example 12 with the following exception: an aliquot of the treated enzyme solution was added at a 100-fold dilution to a 1% birchwood xylan solution in 200 mM bis-tris propane buffer at pH 7.0 that had been pre-incubated to 70° C. (for TrX-10H-11D-27M-29L-40R-58R-75A-99C-105H-118C-125A-129E-131N and TrX-10H-11D-27M-29L-40R-58R-75A-99C-105H-118C-125A-129E) or pH 6.5 pre-incubated to 55° C. The residual activity was normalized to the activity measured for each enzyme after 0 min pre-incubation at 50° C.

Both TrX-10H-11D-27M-29L-40R-58R-75A-99C-105H-118C-125A-129E-131N and TrX-10H-11D-27M-29L-40R-58R-75A-99C-105H-118C-125A-129E containing the 99C-118C disulfide show superior thermostability to TrX-HML, which lacks the 99C-118C disulfide. The $T_{50}$ was determined to be 71-72° C. for the disulfide xylanases, as compared to a $T_{50}$ of 65° C. for the TrX-10H-27M-29L (FIG. 17).

The present invention has been described with regard to preferred embodiments. However, it will be obvious to persons skilled in the art that a number of variations and modifications can be made without departing from the scope of the invention as described herein.

All references and citations are herein incorporated by reference.

REFERENCES

Arase, A., Yomo, T., Urabe, T., Hata, Y., Katsube, Y. and Okada, H. (1993) FEBS Lett. 316:123-127.
Campbell, R. L., Rose, D. R., Sung, W. L., Yaguchi, M. and Wakarchuk, W., U.S. Pat. No. 5,405,769.
Dani, V. S., Ramakrishnan, C. and Varadarajan, R. (2003) Protein Engineering 16:187-193.
Esteves, F. D. L., Ruelle, V., Lamotte-Brasseur, J., Quinting, B. and Frere, J.-M. (2004) Protein Science 13:1209-1218.
Fenel, F., Leisola, M., Janis, J. and Turunen (2004) J. Biotechnology 108:137-143.
Fushinobu, S., Ito, K., Konno, M., Wakagi, T. and Matsuzawa, H. (1998) Protein Engineering 11:1121-1128.
Gruber, K., Klintschar, G., Hayn, M, Schlacher, A., Steiner, W. and Kratky, C. (1998) Biochemistry 37:13475-13485.
Hakulinen, N., Turunen, O., Janis, J., Leisola, M. and Rouvinen, J. (2003) Eur. J. Biochem. 270:1399-1412.
Irwin, D., Jung, E. D. and Wilson, D. B. (1994) Appl. Environ. Microbiol. 60:763-770.
Krengel, U. and Dijkstra, B. W. (1996) J. Mol. Biol. 263:70-78.
Lee, S. L., Forsberg, C. W., and Rattray, J. B. (1987) Appl. Environ. Microbiol. 53:644-650.
Lever (1972) Analytical Biochem 47:273-279.
Lüthi, E., Jasmat, N. B., and Bergquist, P. L. (1990) Appl. Environ. Microbiol. 56:2677-2683.
Mathrani, I. M. and Ahring, B. K. (1992) Appl. Microbiol. Biotechnol. 38:23-27.
Misset, O. (1993) in Stability and Stabilization of Enzymes, edited by W. J. J. van den Tweel, A. Harder and R. M. Buitelaar; published by Elsevier Science Publishers B. V. pp 111-131.
Nissen A. M., Anker, L., Munk, N., and Lange, N. K. in Xylans and Xylanases, edited by J. Visser, G. Beldman, M. A. Kusters-van Someren and A. G. J. Voragen, published by Elsevier, Amsterdam, 1992. p 325-337.
Sakka, K., Kojima Y., Kondo, T., Karita, S., Ohmiya, K. and Shimada, K. (1993) Biosci. Biotech. Biochem. 57:273-277.
Sapag, A., Wouters, J., Lambert, C., de Ioannes, P., Eyzaguirre, J. and Depiereux, E. (2002) J. Biotechnology 95:109-131.
Simpson, H. D., Haufler, U. R., and Daniel, R. M. (1991) Biochem. J. (1991) 277:413-417.
Sowdhamini, R., Srinivasan, N., Shoichet, B., Santi, D. V., Ramakrishnan, C. and Balaram, P. (1989) Protein Engineering 3:95-103.
Sung, W. L., Yao. F.-L., Zahab, D. M. and Narang, S. A. (1986) Proc. Natl. Acad. Sci. USA 83:561-565.
Sung, W. L., Luk, C. K., Zahab, D. M. and Wakarchuk, W. (1993) Protein Expression Purif. 4:200-206.
Sung, W. L., Luk, C. K., Chan, B., Wakarchuk, W., Yaguchi, M., Campbell, R., Willick, G., Ishikawa, K. and Zabab, D. M. (1995) Biochem. Cell. Biol. 73:253-259.
Torronen, A., and Rouvinen, J. (1995) Biochemistry 34:847-856
Turunen, O., Etuaho, K., Fenel. F, Vehmaanpera, J., Wu, X., Rouvinen, J. and Leisola, M. (2001) J. Biotechnology 88:37-46.
Turunen, O., Vuorio, M., Fenel. F. and Leisola, M. (2002) Protein Engineering (2002) 15:141-145.
Wakarchuck W. W., Sung, W. L., Campbell, R. L., Cunningham, A., Watson, D. C. and Yaguchi, M. (1994) Protein Engineering 7:1379-1386.
Winterhalter C. and Liebl, W. (1995) Appl. Environ. Bicrobiol. 61:1810-1815.

The invention claimed is:

1. A modified Family 11 xylanase comprising a substituted amino acid at position 40 selected from the group consisting of arginine, cysteine, phenylalanine, and histidine, and an intramolecular disulfide bond produced by substitution of an amino acid at position 99, 118 or both positions 99 and 118 with a cysteine, said positions determined from sequence alignment of said modified Family 11 xylanase with the *Trichoderma reesei* xylanase II amino acid sequence of SEQ ID NO:16, wherein said modified Family 11 xylanase exhibits
   a. increased thermophilicity, alkalophilicity, thermostability, or a combination thereof, relative to a parental Family 11 xylanase from which the modified Family 11 xylanase is derived, and
   b. at least 92% amino acid sequence identity to SEQ ID NO: 16.

2. The modified Family 11 xylanase of claim 1, wherein the substituted amino acid at position 40 is histidine.

3. The modified xylanase of claim 1, further comprising a basic substituted amino acid at position 58.

4. The modified xylanase of claim 3, wherein the basic substituted amino acid at position 58 is an Arg.

5. The modified Family 11 xylanase of claim 1, wherein said parental Family 11 xylanase is SEQ ID NO: 16.

6. The modified xylanase of claim 3, further comprising a basic substituted amino acid at position 10, a hydrophobic substituted amino acid at position 27 and a hydrophobic substituted amino acid at position 29.

7. The modified xylanase of claim 6, wherein the basic substituted amino acid at position 10 is histidine, the hydrophobic substituted amino acid at position 27 is methionine, and the hydrophobic substituted amino acid at position 29 is leucine.

8. The modified xylanase of claim 7, further comprising a non-polar substituted amino acid at position 75, a basic substituted amino acid at position 105, a non-polar substituted amino acid at position 125, and an acidic amino acid at position 129.

9. The modified xylanase of claim 8, wherein said non-polar substituted amino acid at position 75 is alanine, said basic substituted amino acid at position 105 is histidine, said non-polar substituted amino acid at position 125 is alanine, and said acidic amino acid at position 129 is glutamic acid.

10. The modified xylanase of claim 9, further comprising an acidic amino acid at position 11.

11. The modified xylanase of claim 10, wherein the acidic amino acid at position 11 is aspartic acid.

12. The modified xylanase of claim 11, further comprising asparagine at position 131.

13. The modified xylanase of claim 3, wherein the substituted amino acid at position 40 is a His and the basic substituted amino acid at position 58 is arginine.

14. The modified xylanase of claim 13, further comprising a basic substituted amino acid at position 10, a hydrophobic substituted amino acid at position 27, and a hydrophobic substituted amino acid at position 29.

15. The modified xylanase of claim 14, wherein the basic substituted amino acid at position 10 is histidine, the hydrophobic substituted amino acid at position 27 is methionine and the hydrophobic substituted amino acid at position 29 is leucine.

16. The modified xylanase of claim 15, further comprising a non-polar substituted amino acid at position 75, a basic substituted amino acid at position 105, a non-polar substituted amino acid at position 125, and an acidic amino acid at position 129.

17. The modified xylanase of claim 16, wherein said non-polar substituted amino acid at position 75 is alanine, said basic substituted amino acid at position 105 is histidine, said non-polar substituted amino acid at position 125 is alanine, and said acidic amino acid at position 129 is glutamic acid.

18. The modified xylanase of claim 17, further comprising an acidic amino acid at position 11.

19. The modified xylanase of claim 18, wherein the acidic amino acid at position 11 is aspartic acid.

20. The modified xylanase of claim 19, further comprising asparagine at position 131.

21. The modified xylanase of claim 19, further comprising cysteine at position 52.

22. The modified xylanase of claim 21, further comprising a basic substituted amino acid at each of positions 144 and 161.

23. The modified xylanase of claim 22, wherein the basic substituted amino acid at each of positions 144 and 161 is arginine.

24. The modified Family 11 xylanase according to claim 1, wherein said modified xylanase has a maximum effective temperature (MET) between about 65° C. and about 85° C.

25. The modified Family 11 xylanase according to claim 1, wherein said modified xylanase has a maximum effective pH (MEP) between about pH 6.5 and about pH 8.0.

26. The modified Family 11 xylanase of claim 1, wherein the intramolecular disulfide bond encloses a loop having between 10 and 24 amino acids.

27. The modified Family 11 xylanase of claim 26, wherein the substituted amino acid at position 40 is histidine.

28. The modified Family 11 xylanase of claim 1, selected from the group consisting of SEQ ID NO: 67, SEQ ID NO:69, SEQ ID NO:70, SEQ ID NO:71, SEQ ID NO: 75, SEQ ID NO: 76, SEQ ID NO: 77, SEQ ID NO: 79, SEQ ID NO:80 and SEQ ID NO:81.

29. A modified Family 11 xylanase consisting of
   a. a substituted amino acid at position 40 selected from the group consisting of arginine, cysteine, phenylalanine, and histidine;
   b. an intramolecular disulfide bond produced by substitution of an amino acid at position 99, 118 or both positions 99 and 118 with a cysteine; and
   c. from 0 to 12 additional amino acid substitutions selected from the group consisting of a basic amino acid at position 10, an acidic amino acid at position 11, a hydrophobic amino acid at position 27, a hydrophobic amino acid at position 29, a cysteine at position 52, a non-polar amino acid at position 75, a basic amino acid at position 105, a non-polar amino acid at position 125, an acidic amino acid at position 129, an asparagine at position 131, a basic amino acid at position 144, and a basic amino acid at position 161,
said positions determined from sequence alignment of said modified Family 11 xylanase with a *Trichoderma reesei* xylanase II amino acid sequence as defined in SEQ ID NO:16, wherein said parental Family 11 xylanase is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21.

30. The modified Family 11 xylanase enzyme of claim 29, wherein
   the basic amino acid at position 10 is His, the basic amino acid at position 10 is Asp, the hydrophobic amino acid at position 27 is Met, the hydrophobic amino acid at position 29 is Leu, the non-polar amino acid at position 75 is Ala, the basic amino acid at position 105 is His, the non-polar amino acid at position 125 is Ala, the acidic amino acid at position 129 is Glu, the basic amino acid at position 144 is Arg and the basic amino acid residue at position 161 is Arg.

* * * * *

SEQUENCE LISTING

```
<160> NUMBER OF SEQ ID NOS: 110

<210> SEQ ID NO 1
<211> LENGTH: 184
<212> TYPE: PRT
<213> ORGANISM: Aspergillus niger

<400> SEQUENCE: 1

Ser Ala Gly Ile Asn Tyr Val Gln Asn Tyr Asn Gly Asn Leu Gly Asp
1               5                   10                  15

Phe Thr Tyr Asp Glu Ser Ala Gly Thr Phe Ser Met Tyr Trp Glu Asp
            20                  25                  30
```

```
Gly Val Ser Ser Asp Phe Val Val Gly Leu Gly Trp Thr Thr Gly Ser
            35                  40                  45

Ser Asn Ala Ile Thr Tyr Ser Ala Glu Tyr Ser Ala Ser Gly Ser Ser
 50                  55                  60

Ser Tyr Leu Ala Val Tyr Gly Trp Val Asn Tyr Pro Gly Ala Glu Tyr
 65                  70                  75                  80

Tyr Ile Val Glu Asp Tyr Gly Asp Tyr Asn Pro Cys Ser Ser Ala Thr
                85                  90                  95

Ser Leu Gly Thr Val Tyr Ser Asp Gly Ser Thr Tyr Gln Val Cys Thr
            100                 105                 110

Asp Thr Arg Ile Asn Glu Pro Ser Ile Thr Gly Thr Ser Thr Phe Thr
            115                 120                 125

Gln Tyr Phe Ser Val Arg Glu Ser Thr Arg Thr Ser Gly Thr Val Thr
130                 135                 140

Val Ala Asn His Phe Asn Phe Trp Ala Gln His Gly Phe Gly Asn Ser
145                 150                 155                 160

Asp Phe Asn Tyr Gln Val Met Ala Val Glu Ala Trp Ser Gly Ala Gly
                165                 170                 175

Ser Ala Ser Val Thr Ile Ser Ser
            180

<210> SEQ ID NO 2
<211> LENGTH: 184
<212> TYPE: PRT
<213> ORGANISM: Aspergillus tubingensis

<400> SEQUENCE: 2

Ser Ala Gly Ile Asn Tyr Val Gln Asn Tyr Asn Gly Asn Leu Gly Asp
 1               5                  10                  15

Phe Thr Tyr Asp Glu Ser Ala Gly Thr Phe Ser Met Tyr Trp Glu Asp
                20                  25                  30

Gly Val Ser Ser Asp Phe Val Val Gly Leu Gly Trp Thr Thr Gly Ser
            35                  40                  45

Ser Asn Ala Ile Thr Tyr Ser Ala Glu Tyr Ser Ala Ser Gly Ser Ala
 50                  55                  60

Ser Tyr Leu Ala Val Tyr Gly Trp Val Asn Tyr Pro Gln Ala Glu Tyr
 65                  70                  75                  80

Tyr Ile Val Glu Asp Tyr Gly Asp Tyr Asn Pro Cys Ser Ser Ala Thr
                85                  90                  95

Ser Leu Gly Thr Val Tyr Ser Asp Gly Ser Thr Tyr Gln Val Cys Thr
            100                 105                 110

Asp Thr Arg Thr Asn Glu Pro Ser Ile Thr Gly Thr Ser Thr Phe Thr
            115                 120                 125

Gln Tyr Phe Ser Val Arg Glu Ser Thr Arg Thr Ser Gly Thr Val Thr
130                 135                 140

Val Ala Asn His Phe Asn Phe Trp Ala His His Gly Phe Gly Asn Ser
145                 150                 155                 160

Asp Phe Asn Tyr Gln Val Val Ala Val Glu Ala Trp Ser Gly Ala Gly
                165                 170                 175

Ser Ala Ser Val Thr Ile Ser Ser
            180

<210> SEQ ID NO 3
<211> LENGTH: 185
<212> TYPE: PRT
<213> ORGANISM: Bacillus circulans
```

```
<400> SEQUENCE: 3

Ala Ser Thr Asp Tyr Trp Gln Asn Trp Thr Asp Gly Gly Gly Ile Val
 1               5                  10                  15

Asn Ala Val Asn Gly Ser Gly Gly Asn Tyr Ser Val Asn Trp Ser Asn
             20                  25                  30

Thr Gly Asn Phe Val Val Gly Lys Gly Trp Thr Thr Gly Ser Pro Phe
         35                  40                  45

Arg Thr Ile Asn Tyr Asn Ala Gly Val Trp Ala Pro Asn Gly Asn Gly
     50                  55                  60

Tyr Leu Thr Leu Tyr Gly Trp Thr Arg Ser Pro Leu Ile Glu Tyr Tyr
 65                  70                  75                  80

Val Val Asp Ser Trp Gly Thr Tyr Arg Pro Thr Gly Thr Tyr Lys Gly
             85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Arg Thr Thr Phe Thr Gln Tyr
            115                 120                 125

Trp Ser Val Arg Gln Ser Lys Arg Pro Thr Gly Ser Asn Ala Thr Ile
130                 135                 140

Thr Phe Thr Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
            165                 170                 175

Ser Gly Ser Ser Asn Val Thr Val Trp
            180                 185

<210> SEQ ID NO 4
<211> LENGTH: 201
<212> TYPE: PRT
<213> ORGANISM: Bacillus pumilus

<400> SEQUENCE: 4

Arg Thr Ile Thr Asn Asn Glu Met Gly Asn His Ser Gly Tyr Asp Tyr
 1               5                  10                  15

Glu Leu Trp Lys Asp Tyr Gly Asn Thr Ser Met Thr Leu Asn Asn Gly
             20                  25                  30

Gly Ala Phe Ser Ala Gly Trp Asn Asn Ile Gly Asn Ala Leu Phe Arg
         35                  40                  45

Lys Gly Lys Lys Phe Asp Ser Thr Arg Thr His His Gln Leu Gly Asn
     50                  55                  60

Ile Ser Ile Asn Tyr Asn Ala Ser Phe Asn Pro Ser Gly Asn Ser Tyr
 65                  70                  75                  80

Leu Cys Val Tyr Gly Trp Thr Gln Ser Pro Leu Ala Glu Tyr Tyr Ile
             85                  90                  95

Val Asp Ser Trp Gly Thr Tyr Arg Pro Thr Gly Ala Tyr Lys Gly Ser
            100                 105                 110

Phe Tyr Ala Asp Gly Gly Thr Tyr Asp Ile Tyr Glu Thr Thr Arg Val
            115                 120                 125

Asn Gln Pro Ser Ile Ile Gly Ile Ala Thr Phe Lys Gln Tyr Trp Ser
130                 135                 140

Val Arg Gln Thr Lys Arg Thr Ser Gly Thr Val Ser Val Ser Ala His
145                 150                 155                 160

Phe Arg Lys Trp Glu Ser Leu Gly Met Pro Met Gly Lys Met Tyr Glu
            165                 170                 175
```

```
Thr Ala Phe Thr Val Glu Gly Tyr Gln Ser Ser Gly Ser Ala Asn Val
            180                 185                 190

Met Thr Asn Gln Leu Phe Ile Gly Asn
            195                 200

<210> SEQ ID NO 5
<211> LENGTH: 185
<212> TYPE: PRT
<213> ORGANISM: Bacillus subtilis

<400> SEQUENCE: 5

Ala Ser Thr Asp Tyr Trp Gln Asn Trp Thr Asp Gly Gly Gly Ile Val
  1               5                  10                  15

Asn Ala Val Asn Gly Ser Gly Gly Asn Tyr Ser Val Asn Trp Ser Asn
                 20                  25                  30

Thr Gly Asn Phe Val Val Gly Lys Gly Trp Thr Thr Gly Ser Pro Phe
             35                  40                  45

Arg Thr Ile Asn Tyr Asn Ala Gly Val Trp Ala Pro Asn Gly Asn Gly
         50                  55                  60

Tyr Leu Thr Leu Tyr Gly Trp Thr Arg Ser Pro Leu Ile Glu Tyr Tyr
 65                  70                  75                  80

Val Val Asp Ser Trp Gly Thr Tyr Arg Pro Thr Gly Thr Tyr Lys Gly
                 85                  90                  95

Thr Val Lys Ser Asp Gly Gly Thr Tyr Asp Ile Tyr Thr Thr Thr Arg
                100                 105                 110

Tyr Asn Ala Pro Ser Ile Asp Gly Asp Arg Thr Thr Phe Thr Gln Tyr
            115                 120                 125

Trp Ser Val Arg Gln Ser Lys Arg Pro Thr Gly Ser Asn Ala Thr Ile
        130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 6
<211> LENGTH: 211
<212> TYPE: PRT
<213> ORGANISM: Clostridium acetobutylicum

<400> SEQUENCE: 6

Ser Ala Phe Asn Thr Gln Ala Ala Pro Lys Thr Ile Thr Ser Asn Glu
  1               5                  10                  15

Ile Gly Val Asn Gly Gly Tyr Asp Tyr Glu Leu Trp Lys Asp Tyr Gly
                 20                  25                  30

Asn Thr Ser Met Thr Leu Lys Asn Gly Gly Ala Phe Ser Cys Gln Trp
             35                  40                  45

Ser Asn Ile Gly Asn Ala Leu Phe Arg Lys Gly Lys Lys Phe Asn Asp
         50                  55                  60

Thr Gln Thr Tyr Lys Gln Leu Gly Asn Ile Ser Val Asn Tyr Asn Cys
 65                  70                  75                  80

Asn Tyr Gln Pro Tyr Gly Asn Ser Tyr Leu Cys Val Tyr Gly Trp Thr
                 85                  90                  95

Ser Ser Pro Leu Val Glu Tyr Tyr Ile Val Asp Ser Trp Gly Ser Trp
                100                 105                 110
```

Arg Pro Pro Gly Gly Thr Ser Lys Gly Thr Ile Thr Val Asp Gly Gly
            115                 120                 125

Ile Tyr Asp Ile Tyr Glu Thr Thr Arg Ile Asn Gln Pro Ser Ile Gln
    130                 135                 140

Gly Asn Thr Thr Phe Lys Gln Tyr Trp Ser Val Arg Arg Thr Lys Arg
145                 150                 155                 160

Thr Ser Gly Thr Ile Ser Val Ser Lys His Phe Ala Ala Trp Glu Ser
                165                 170                 175

Lys Gly Met Pro Leu Gly Lys Met His Glu Thr Ala Phe Asn Ile Glu
            180                 185                 190

Gly Tyr Gln Ser Ser Gly Lys Ala Asp Val Asn Ser Met Ser Ile Asn
        195                 200                 205

Ile Gly Lys
    210

<210> SEQ ID NO 7
<211> LENGTH: 206
<212> TYPE: PRT
<213> ORGANISM: Clostridium stercorarium

<400> SEQUENCE: 7

Gly Arg Ile Ile Tyr Asp Asn Glu Thr Gly Thr His Gly Gly Tyr Asp
1               5                   10                  15

Tyr Glu Leu Trp Lys Asp Tyr Gly Asn Thr Ile Met Glu Leu Asn Asp
            20                  25                  30

Gly Gly Thr Phe Ser Cys Gln Trp Ser Asn Ile Gly Asn Ala Leu Phe
        35                  40                  45

Arg Lys Gly Arg Lys Phe Asn Ser Asp Lys Thr Tyr Gln Glu Leu Gly
    50                  55                  60

Asp Ile Val Val Glu Tyr Gly Cys Asp Tyr Asn Pro Asn Gly Asn Ser
65                  70                  75                  80

Tyr Leu Cys Val Tyr Gly Trp Thr Arg Asn Phe Leu Val Glu Tyr Tyr
                85                  90                  95

Ile Val Glu Ser Trp Gly Ser Trp Arg Pro Pro Gly Ala Thr Pro Lys
            100                 105                 110

Gly Thr Ile Thr Gln Trp Met Ala Gly Thr Tyr Glu Ile Tyr Glu Thr
        115                 120                 125

Thr Arg Val Asn Gln Pro Ser Ile Asp Gly Thr Ala Thr Phe Gln Gln
    130                 135                 140

Tyr Trp Ser Val Arg Thr Ser Lys Arg Thr Ser Gly Thr Ile Ser Val
145                 150                 155                 160

Thr Glu His Phe Lys Gln Trp Glu Arg Met Gly Met Arg Met Gly Lys
                165                 170                 175

Met Tyr Glu Val Ala Leu Thr Val Glu Gly Tyr Gln Ser Ser Gly Tyr
            180                 185                 190

Ala Asn Val Tyr Lys Asn Glu Ile Arg Ile Gly Ala Asn Pro
        195                 200                 205

<210> SEQ ID NO 8
<211> LENGTH: 211
<212> TYPE: PRT
<213> ORGANISM: Ruminococcus flavefaciens

<400> SEQUENCE: 8

Ser Ala Ala Asp Gln Gln Thr Arg Gly Asn Val Gly Gly Tyr Asp Tyr
1               5                   10                  15

Glu Met Trp Asn Gln Asn Gly Gln Gly Gln Ala Ser Met Asn Pro Gly
            20                  25                  30

Ala Gly Ser Phe Thr Cys Ser Trp Ser Asn Ile Glu Asn Phe Leu Ala
            35                  40                  45

Arg Met Gly Lys Asn Tyr Asp Ser Gln Lys Asn Tyr Lys Ala Phe
50                  55                  60

Gly Asn Ile Val Leu Thr Tyr Asp Val Glu Tyr Thr Pro Arg Gly Asn
65                  70                  75                  80

Ser Tyr Met Cys Val Tyr Gly Trp Thr Arg Asn Pro Leu Met Glu Tyr
                85                  90                  95

Tyr Ile Val Glu Gly Trp Gly Asp Trp Arg Pro Pro Gly Asn Asp Gly
            100                 105                 110

Glu Val Lys Gly Thr Val Ser Ala Asn Gly Asn Thr Tyr Asp Ile Arg
            115                 120                 125

Lys Thr Met Arg Tyr Asn Gln Pro Ser Leu Asp Gly Thr Ala Thr Phe
130                 135                 140

Pro Gln Tyr Trp Ser Val Arg Gln Thr Ser Gly Ser Ala Asn Asn Gln
145                 150                 155                 160

Thr Asn Tyr Met Lys Gly Thr Ile Asp Val Ser Lys His Phe Asp Ala
                165                 170                 175

Trp Ser Ala Ala Gly Leu Asp Met Ser Gly Thr Leu Tyr Glu Val Ser
            180                 185                 190

Leu Asn Ile Glu Gly Tyr Arg Ser Asn Gly Ser Ala Asn Val Lys Ser
            195                 200                 205

Val Ser Val
    210

<210> SEQ ID NO 9
<211> LENGTH: 197
<212> TYPE: PRT
<213> ORGANISM: Schizophyllum commune

<400> SEQUENCE: 9

Ser Gly Thr Pro Ser Ser Thr Gly Thr Asp Gly Gly Tyr Tyr Tyr Ser
1               5                   10                  15

Trp Trp Thr Asp Gly Ala Gly Asp Ala Thr Tyr Gln Asn Asn Gly Gly
            20                  25                  30

Gly Ser Tyr Thr Leu Thr Trp Ser Gly Asn Asn Gly Asn Leu Val Gly
            35                  40                  45

Gly Lys Gly Trp Asn Pro Gly Ala Ala Ser Arg Ser Ile Ser Tyr Ser
        50                  55                  60

Gly Thr Tyr Gln Pro Asn Gly Asn Ser Tyr Leu Ser Val Tyr Gly Trp
65                  70                  75                  80

Thr Arg Ser Ser Leu Ile Glu Tyr Tyr Ile Val Glu Ser Tyr Gly Ser
                85                  90                  95

Tyr Asp Pro Ser Ser Ala Ala Ser His Lys Gly Ser Val Thr Cys Asn
            100                 105                 110

Gly Ala Thr Tyr Asp Ile Leu Ser Thr Trp Arg Tyr Asn Ala Pro Ser
            115                 120                 125

Ile Asp Gly Thr Gln Thr Phe Glu Gln Phe Trp Ser Val Arg Asn Pro
            130                 135                 140

Lys Lys Ala Pro Gly Gly Ser Ile Ser Gly Thr Val Asp Val Gln Cys
145                 150                 155                 160

His Phe Asp Ala Trp Lys Gly Leu Gly Met Asn Leu Gly Ser Glu His

```
                    165                 170                 175
Asn Tyr Gln Ile Val Ala Thr Glu Gly Tyr Gln Ser Ser Gly Thr Ala
                180                 185                 190

Thr Ile Thr Val Thr
        195

<210> SEQ ID NO 10
<211> LENGTH: 191
<212> TYPE: PRT
<213> ORGANISM: Streptomyces lividans Xyn B

<400> SEQUENCE: 10

Asp Thr Val Val Thr Thr Asn Gln Glu Gly Thr Asn Asn Gly Tyr Tyr
  1               5                  10                  15

Tyr Ser Phe Trp Thr Asp Ser Gln Gly Thr Val Ser Met Asn Met Gly
                 20                  25                  30

Ser Gly Gly Gln Tyr Ser Thr Ser Trp Arg Asn Thr Gly Asn Phe Val
             35                  40                  45

Ala Gly Lys Gly Trp Ala Asn Gly Gly Arg Arg Thr Val Gln Tyr Ser
         50                  55                  60

Gly Ser Phe Asn Pro Ser Gly Asn Ala Tyr Leu Ala Leu Tyr Gly Trp
 65                  70                  75                  80

Thr Ser Asn Pro Leu Val Glu Tyr Tyr Ile Val Asp Asn Trp Gly Thr
                 85                  90                  95

Tyr Arg Pro Thr Gly Glu Tyr Lys Gly Thr Val Thr Ser Asp Gly Gly
            100                 105                 110

Thr Tyr Asp Ile Tyr Lys Thr Thr Arg Val Asn Lys Pro Ser Val Glu
        115                 120                 125

Gly Thr Arg Thr Phe Asp Gln Tyr Trp Ser Val Arg Gln Ser Lys Arg
    130                 135                 140

Thr Gly Gly Thr Ile Thr Thr Gly Asn His Phe Asp Ala Trp Ala Arg
145                 150                 155                 160

Ala Gly Met Pro Leu Gly Asn Phe Ser Tyr Tyr Met Ile Asn Ala Thr
                165                 170                 175

Glu Gly Tyr Gln Ser Ser Gly Thr Ser Ser Ile Asn Val Gly Gly
            180                 185                 190

<210> SEQ ID NO 11
<211> LENGTH: 191
<212> TYPE: PRT
<213> ORGANISM: Streptomyces lividans Xyn C

<400> SEQUENCE: 11

Ala Thr Thr Ile Thr Thr Asn Gln Thr Gly Thr Asp Gly Met Tyr Tyr
  1               5                  10                  15

Ser Phe Trp Thr Asp Gly Gly Ser Val Ser Met Thr Leu Asn Gly
                 20                  25                  30

Gly Gly Ser Tyr Ser Thr Gln Trp Thr Asn Cys Gly Asn Phe Val Ala
             35                  40                  45

Gly Lys Gly Trp Ser Thr Gly Asp Gly Asn Val Arg Tyr Asn Gly Tyr
         50                  55                  60

Phe Asn Pro Val Gly Asn Gly Tyr Gly Cys Leu Tyr Gly Trp Thr Ser
 65                  70                  75                  80

Asn Pro Leu Val Glu Tyr Tyr Ile Val Asp Asn Trp Gly Ser Tyr Arg
                 85                  90                  95

Pro Thr Gly Thr Tyr Lys Gly Thr Val Ser Ser Asp Gly Gly Thr Tyr
```

```
                100             105             110
Asp Ile Tyr Gln Thr Thr Arg Tyr Asn Ala Pro Ser Val Glu Gly Thr
            115                 120                 125

Lys Thr Phe Gln Gln Tyr Trp Ser Val Arg Gln Ser Lys Val Thr Ser
    130                 135                 140

Gly Ser Gly Thr Ile Thr Thr Gly Asn His Phe Asp Ala Trp Ala Arg
145                 150                 155                 160

Ala Gly Met Asn Met Gly Gln Phe Arg Tyr Tyr Met Ile Asn Ala Thr
                165                 170                 175

Glu Gly Tyr Gln Ser Ser Gly Ser Ser Asn Ile Thr Val Ser Gly
            180                 185                 190

<210> SEQ ID NO 12
<211> LENGTH: 189
<212> TYPE: PRT
<213> ORGANISM: Streptomyces sp. No. 36a

<400> SEQUENCE: 12

Ala Thr Thr Ile Thr Asn Glu Thr Gly Tyr Asp Gly Met Tyr Tyr Ser
1               5                   10                  15

Phe Trp Thr Asp Gly Gly Gly Ser Val Ser Met Thr Leu Asn Gly Gly
                20                  25                  30

Gly Ser Tyr Ser Thr Arg Trp Thr Asn Cys Gly Asn Phe Val Ala Gly
            35                  40                  45

Lys Gly Trp Ala Asn Gly Gly Arg Arg Thr Val Arg Tyr Thr Gly Trp
        50                  55                  60

Phe Asn Pro Ser Gly Asn Gly Tyr Gly Cys Leu Tyr Gly Trp Thr Ser
65                  70                  75                  80

Asn Pro Leu Val Glu Tyr Tyr Ile Val Asp Asn Trp Gly Ser Tyr Arg
                85                  90                  95

Pro Thr Gly Glu Thr Arg Gly Thr Val His Ser Asp Gly Gly Thr Tyr
            100                 105                 110

Asp Ile Tyr Lys Thr Thr Arg Tyr Asn Ala Pro Ser Val Glu Ala Pro
        115                 120                 125

Ala Ala Phe Asp Gln Tyr Trp Ser Val Arg Gln Ser Lys Val Thr Ser
    130                 135                 140

Gly Thr Ile Thr Thr Gly Asn His Phe Asp Ala Trp Ala Arg Ala Gly
145                 150                 155                 160

Met Asn Met Gly Asn Phe Arg Tyr Tyr Met Ile Asn Ala Thr Glu Gly
                165                 170                 175

Tyr Gln Ser Ser Gly Ser Ser Thr Ile Thr Val Ser Gly
            180                 185

<210> SEQ ID NO 13
<211> LENGTH: 189
<212> TYPE: PRT
<213> ORGANISM: Thermomonospora fusca

<400> SEQUENCE: 13

Ala Val Thr Ser Asn Glu Thr Gly Tyr His Asp Gly Tyr Phe Tyr Ser
1               5                   10                  15

Phe Trp Thr Asp Ala Pro Gly Thr Val Ser Met Glu Leu Gly Pro Gly
                20                  25                  30

Gly Asn Tyr Ser Thr Ser Trp Arg Asn Thr Gly Asn Phe Val Ala Gly
            35                  40                  45

Lys Gly Trp Ala Thr Gly Gly Arg Arg Thr Val Thr Tyr Ser Ala Ser
```

```
               50                  55                  60
Phe Asn Pro Ser Gly Asn Ala Tyr Leu Thr Leu Tyr Gly Trp Thr Arg
 65                  70                  75                  80

Asn Pro Leu Val Glu Tyr Tyr Ile Val Glu Ser Trp Gly Thr Tyr Arg
                 85                  90                  95

Pro Thr Gly Thr Tyr Met Gly Thr Val Thr Thr Asp Gly Gly Thr Tyr
            100                 105                 110

Asp Ile Tyr Lys Thr Thr Arg Tyr Asn Ala Pro Ser Ile Glu Gly Thr
        115                 120                 125

Arg Thr Phe Asp Gln Tyr Trp Ser Val Arg Gln Ser Lys Arg Thr Ser
130                 135                 140

Gly Thr Ile Thr Ala Gly Asn His Phe Asp Ala Trp Ala Arg His Gly
145                 150                 155                 160

Met His Leu Gly Thr His Asp Tyr Met Ile Met Ala Thr Glu Gly Tyr
                165                 170                 175

Gln Ser Ser Gly Ser Ser Asn Val Thr Leu Gly Thr Ser
            180                 185
```

<210> SEQ ID NO 14
<211> LENGTH: 190
<212> TYPE: PRT
<213> ORGANISM: Trichoderma harzianum

<400> SEQUENCE: 14

```
Gln Thr Ile Gly Pro Gly Thr Gly Tyr Ser Asn Gly Tyr Tyr Tyr Ser
  1               5                  10                  15

Tyr Trp Asn Asp Gly His Ala Gly Val Thr Tyr Thr Asn Gly Gly Gly
             20                  25                  30

Gly Ser Phe Thr Val Asn Trp Ser Asn Ser Gly Asn Phe Val Gly Gly
         35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Ser Ile Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Ser His Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 15
<211> LENGTH: 178
<212> TYPE: PRT
<213> ORGANISM: Trichoderma reesei Xyn I

<400> SEQUENCE: 15

```
Ala Ser Ile Asn Tyr Asp Gln Asn Tyr Gln Thr Gly Gly Gln Val Ser
```

```
              1               5                  10                 15
            Tyr Ser Pro Ser Asn Thr Gly Phe Ser Val Asn Trp Asn Thr Gln Asp
                           20                  25                 30

Asp Phe Val Val Gly Val Gly Trp Thr Thr Gly Ser Ser Ala Pro Ile
                           35                  40                 45

Asn Phe Gly Gly Ser Phe Ser Val Asn Ser Gly Thr Gly Leu Leu Ser
                           50                  55                 60

Val Tyr Gly Trp Ser Thr Asn Pro Leu Val Glu Tyr Tyr Ile Met Glu
             65                 70                  75                 80

Asp Asn His Asn Tyr Pro Ala Gln Gly Thr Val Lys Gly Thr Val Thr
                               85                  90                 95

Ser Asp Gly Ala Thr Tyr Thr Ile Trp Glu Asn Thr Arg Val Asn Glu
                           100                 105                110

Pro Ser Ile Gln Gly Thr Ala Thr Phe Asn Gln Tyr Ile Ser Val Arg
                           115                 120                125

Asn Ser Pro Arg Thr Ser Gly Thr Val Thr Val Gln Asn His Phe Asn
                           130                 135                140

Trp Ala Ser Leu Gly Leu His Leu Gly Gln Met Met Asn Tyr Gln Val
            145                 150                 155                160

Val Ala Val Glu Gly Trp Gly Gly Ser Gly Ser Ala Ser Gln Ser Val
                               165                 170                175

Ser Asn

<210> SEQ ID NO 16
            <211> LENGTH: 190
            <212> TYPE: PRT
            <213> ORGANISM: Trichoderma reesei Xyn II

<400> SEQUENCE: 16

Gln Thr Ile Gln Pro Gly Thr Gly Tyr Asn Asn Gly Tyr Phe Tyr Ser
              1               5                  10                 15

Tyr Trp Asn Asp Gly His Gly Gly Val Thr Tyr Thr Asn Gly Pro Gly
                           20                  25                 30

Gly Gln Phe Ser Val Asn Trp Ser Asn Ser Gly Asn Phe Val Gly Gly
                           35                  40                 45

Lys Gly Trp Gln Pro Gly Thr Lys Asn Lys Val Ile Asn Phe Ser Gly
                           50                  55                 60

Ser Tyr Asn Pro Asn Gly Asn Ser Tyr Leu Ser Val Tyr Gly Trp Ser
             65                 70                  75                 80

Arg Asn Pro Leu Ile Glu Tyr Tyr Ile Val Glu Asn Phe Gly Thr Tyr
                               85                  90                 95

Asn Pro Ser Thr Gly Ala Thr Lys Leu Gly Glu Val Thr Ser Asp Gly
                           100                 105                110

Ser Val Tyr Asp Ile Tyr Arg Thr Gln Arg Val Asn Gln Pro Ser Ile
                           115                 120                125

Ile Gly Thr Ala Thr Phe Tyr Gln Tyr Trp Ser Val Arg Arg Asn His
                           130                 135                140

Arg Ser Ser Gly Ser Val Asn Thr Ala Asn His Phe Asn Ala Trp Ala
            145                 150                 155                160

Gln Gln Gly Leu Thr Leu Gly Thr Met Asp Tyr Gln Ile Val Ala Val
                               165                 170                175

Glu Gly Tyr Phe Ser Ser Gly Ser Ala Ser Ile Thr Val Ser
                           180                 185                190
```

<210> SEQ ID NO 17
<211> LENGTH: 190
<212> TYPE: PRT
<213> ORGANISM: Trichoderma viride

<400> SEQUENCE: 17

```
Gln Thr Ile Gln Pro Gly Thr Gly Phe Asn Asn Gly Tyr Phe Tyr Ser
 1               5                  10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Thr His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 18
<211> LENGTH: 202
<212> TYPE: PRT
<213> ORGANISM: Fibrobacter succinogenes

<400> SEQUENCE: 18

```
Asn Ser Ser Val Thr Gly Asn Val Gly Ser Ser Pro Tyr His Tyr Glu
 1               5                  10                  15

Ile Trp Tyr Gln Gly Gly Asn Asn Ser Met Thr Phe Tyr Asp Asn Gly
            20                  25                  30

Thr Tyr Lys Ala Ser Trp Asn Gly Thr Asn Asp Phe Leu Ala Arg Val
        35                  40                  45

Gly Phe Lys Tyr Asp Glu Lys His Thr Tyr Glu Glu Leu Gly Pro Ile
    50                  55                  60

Asp Ala Tyr Tyr Lys Trp Ser Lys Gln Gly Ser Ala Gly Gly Tyr Asn
65                  70                  75                  80

Tyr Ile Gly Ile Tyr Gly Trp Thr Val Asp Pro Leu Val Glu Tyr Tyr
                85                  90                  95

Ile Val Asp Asp Trp Phe Asn Lys Pro Gly Ala Asn Leu Leu Gly Gln
            100                 105                 110

Arg Lys Gly Glu Phe Thr Val Asp Gly Asp Thr Tyr Glu Ile Trp Gln
        115                 120                 125

Asn Thr Arg Val Gln Gln Pro Ser Ile Lys Gly Thr Gln Thr Phe Pro
    130                 135                 140

Gln Tyr Phe Ser Val Arg Lys Ser Ala Arg Ser Cys Gly His Ile Asp
```

```
145                 150                 155                 160
Ile Thr Ala His Met Lys Lys Trp Glu Glu Leu Gly Met Lys Met Gly
                    165                 170                 175

Lys Met Tyr Glu Ala Lys Val Leu Val Glu Ala Gly Gly Ser Gly
            180                 185                 190

Ser Phe Asp Val Thr Tyr Phe Lys Met Thr
            195                 200
```

<210> SEQ ID NO 19
<211> LENGTH: 189
<212> TYPE: PRT
<213> ORGANISM: Aspergillus awamori var. kawachi

<400> SEQUENCE: 19

```
Arg Ser Thr Pro Ser Ser Thr Gly Glu Asn Asn Gly Tyr Tyr Tyr Ser
1               5                   10                  15

Phe Trp Thr Asp Gly Gly Gly Asp Val Thr Tyr Thr Asn Gly Asn Ala
                20                  25                  30

Gly Ser Tyr Ser Val Glu Trp Ser Asn Val Gly Asn Phe Val Gly Gly
            35                  40                  45

Lys Gly Trp Asn Pro Gly Ser Ala Lys Asp Ile Thr Tyr Ser Gly Asn
    50                  55                  60

Phe Thr Pro Ser Gly Asn Gly Tyr Leu Ser Val Tyr Gly Trp Thr Thr
65                  70                  75                  80

Asp Pro Leu Ile Glu Tyr Tyr Ile Val Glu Ser Tyr Gly Asp Tyr Asn
                85                  90                  95

Pro Gly Ser Gly Gly Thr Thr Arg Gly Asn Val Ser Ser Asp Gly Ser
            100                 105                 110

Val Tyr Asp Ile Tyr Thr Ala Thr Arg Thr Asn Ala Pro Ser Ile Asp
        115                 120                 125

Gly Thr Gln Thr Phe Ser Gln Tyr Trp Ser Val Arg Gln Asn Lys Arg
    130                 135                 140

Val Gly Gly Thr Val Thr Thr Ser Asn His Phe Asn Ala Trp Ala Lys
145                 150                 155                 160

Leu Gly Met Asn Leu Gly Thr His Asn Tyr Gln Ile Leu Ala Thr Glu
                165                 170                 175

Gly Tyr Gln Ser Ser Gly Ser Ser Ser Ile Thr Ile Gln
            180                 185
```

<210> SEQ ID NO 20
<211> LENGTH: 194
<212> TYPE: PRT
<213> ORGANISM: Thermomyces lanuginosus

<400> SEQUENCE: 20

```
Gln Thr Thr Pro Asn Ser Glu Gly Trp His Asp Gly Tyr Tyr Tyr Ser
1               5                   10                  15

Trp Trp Ser Asp Gly Gly Ala Gln Ala Thr Tyr Thr Asn Leu Glu Gly
                20                  25                  30

Gly Thr Tyr Glu Ile Ser Trp Gly Asp Gly Gly Asn Leu Val Gly Gly
            35                  40                  45

Lys Gly Trp Asn Pro Gly Leu Asn Ala Arg Ala Ile His Phe Glu Gly
    50                  55                  60

Val Tyr Gln Pro Asn Gly Asn Ser Tyr Leu Ala Val Tyr Gly Trp Thr
65                  70                  75                  80

Arg Asn Pro Leu Val Glu Tyr Tyr Ile Val Glu Asn Phe Gly Thr Tyr
```

```
                    85                  90                  95
Asp Pro Ser Ser Gly Ala Thr Asp Leu Gly Thr Val Glu Cys Asp Gly
                100                 105                 110
Ser Ile Tyr Arg Leu Gly Lys Thr Thr Arg Val Asn Ala Pro Ser Ile
                115                 120                 125
Asp Gly Thr Gln Thr Phe Asp Gln Tyr Trp Ser Val Arg Gln Asp Lys
                130                 135                 140
Arg Thr Ser Gly Thr Val Gln Thr Gly Cys His Phe Asp Ala Trp Ala
145                 150                 155                 160
Arg Ala Gly Leu Asn Val Asn Gly Asp His Tyr Tyr Gln Ile Val Ala
                165                 170                 175
Thr Glu Gly Tyr Phe Ser Ser Gly Tyr Ala Arg Ile Thr Val Ala Asp
                180                 185                 190
Val Gly

<210> SEQ ID NO 21
<211> LENGTH: 184
<212> TYPE: PRT
<213> ORGANISM: Aspergillus kawachii Xyn C

<400> SEQUENCE: 21

Ser Ala Gly Ile Asn Tyr Val Gln Asn Tyr Asn Gly Asn Leu Ala Asp
  1               5                  10                  15
Phe Thr Tyr Asp Glu Ser Ala Gly Thr Phe Ser Met Tyr Trp Glu Asp
                 20                  25                  30
Gly Val Ser Ser Asp Phe Val Val Gly Leu Gly Trp Thr Thr Gly Ser
             35                  40                  45
Ser Asn Ala Ile Ser Tyr Ser Ala Glu Tyr Ser Ala Ser Gly Ser Ser
         50                  55                  60
Ser Tyr Leu Ala Val Tyr Gly Trp Val Asn Tyr Pro Gln Ala Glu Tyr
 65                  70                  75                  80
Tyr Ile Val Glu Asp Tyr Gly Asp Tyr Asn Pro Cys Ser Ser Ala Thr
                 85                  90                  95
Ser Leu Gly Thr Val Tyr Ser Asp Gly Ser Thr Tyr Gln Val Cys Thr
                100                 105                 110
Asp Thr Arg Thr Asn Glu Pro Ser Ile Thr Gly Thr Ser Thr Phe Thr
                115                 120                 125
Gln Tyr Phe Ser Val Arg Glu Ser Thr Arg Thr Ser Gly Thr Val Thr
                130                 135                 140
Val Ala Asn His Phe Asn Phe Trp Ala Gln His Gly Phe Gly Asn Ser
145                 150                 155                 160
Asp Phe Asn Tyr Gln Val Met Ala Val Glu Ala Trp Ser Gly Ala Gly
                165                 170                 175
Ser Ala Ser Val Thr Ile Ser Ser
                180

<210> SEQ ID NO 22
<211> LENGTH: 76
<212> TYPE: DNA
<213> ORGANISM: Artificial Sequence
<220> FEATURE:
<223> OTHER INFORMATION: Description of Artificial Sequence: TrX-1

<400> SEQUENCE: 22
ctagctaagg aggctgcaga tgcaaacaat acaaccagga accggttaca acaacggtta      60
cttttacagc tattgg                                                     76
```

<210> SEQ ID NO 23
<211> LENGTH: 78
<212> TYPE: DNA
<213> ORGANISM: Artificial Sequence
<220> FEATURE:
<223> OTHER INFORMATION: Description of Artificial Sequence: XyTv-2

<400> SEQUENCE: 23
aacgatggcc atggtggtgt tacctataca aacgggcccg gaggccaatt tagcgtcaat    60
tggtctaact ccggaaac                                                 78

<210> SEQ ID NO 24
<211> LENGTH: 78
<212> TYPE: DNA
<213> ORGANISM: Artificial Sequence
<220> FEATURE:
<223> OTHER INFORMATION: Description of Artificial Sequence: TrX-3

<400> SEQUENCE: 24
ttcgtaggtg gaaaaggttg gcaacccggg accaaaaata aggtgatcaa cttctctgga    60
tcttataatc cgaatggg                                                 78

<210> SEQ ID NO 25
<211> LENGTH: 74
<212> TYPE: DNA
<213> ORGANISM: Artificial Sequence
<220> FEATURE:
<223> OTHER INFORMATION: Description of Artificial Sequence: XyTv-4

<400> SEQUENCE: 25
aattcatact taagcgtcta tggctggtct agaaacccac tgattgaata ttacattgtc    60
gaaaatttcg gtac                                                     74

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: TrX-8

<400> SEQUENCE: 26
gattcctccg acgtctacgt ttgttatgtt ggtccttggc caatgttgtt g             51

<210> SEQ ID NO 27
<211> LENGTH: 84
<212> TYPE: DNA
<213> ORGANISM: Artificial Sequence
<220> FEATURE:
<223> OTHER INFORMATION: Description of Artificial Sequence: XyTv-7

<400> SEQUENCE: 27
ccaatgaaaa tgtcgataac cttgctaccg gtaccaccac aatggatatg tttgcccggg    60
cctccggtta aatcgcagtt aacc                                          84

<210> SEQ ID NO 28
<211> LENGTH: 78
<212> TYPE: DNA
<213> ORGANISM: Artificial Sequence
<220> FEATURE:
<223> OTHER INFORMATION: Description of Artificial Sequence: TrX-6

<400> SEQUENCE: 28

```
agattgaggc ctttgaagca tccacctttt ccaaccgttg ggccctggtt tttattccac      60
tagttgaaga gacctaga                                                   78

<210> SEQ ID NO 29
<211> LENGTH: 85
<212> TYPE: DNA
<213> ORGANISM: Artificial Sequence
<220> FEATURE:
<223> OTHER INFORMATION: Description of Artificial Sequence: XyTv-5

<400> SEQUENCE: 29
atattaggct taccctttaag tatgaattcg cagataccga ccagatcttt gggtgactaa    60
cttataatgt aacagctttt aaagc                                           85

<210> SEQ ID NO 30
<211> LENGTH: 58
<212> TYPE: DNA
<213> ORGANISM: Artificial Sequence
<220> FEATURE:
<223> OTHER INFORMATION: Description of Artificial Sequence: XyTv-101

<400> SEQUENCE: 30
tcgacaattt cggtacctac aatccgagta ccggcgccac aaaattaggc gaagtcac       58

<210> SEQ ID NO 31
<211> LENGTH: 53
<212> TYPE: DNA
<213> ORGANISM: Artificial Sequence
<220> FEATURE:
<223> OTHER INFORMATION: Description of Artificial Sequence: XyTv-102

<400> SEQUENCE: 31
tagtgatgga tccgtatatg atatctaccg tacccaacgc gttaatcagc cat            53

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: TrX-103

<400> SEQUENCE: 32
cgatcattgg aaccgccacc ttttatcagt actggagtgt tagacgtaat catcggagc      59

<210> SEQ ID NO 33
<211> LENGTH: 69
<212> TYPE: DNA
<213> ORGANISM: Artificial Sequence
<220> FEATURE:
<223> OTHER INFORMATION: Description of Artificial Sequence: XyTv-104

<400> SEQUENCE: 33
tccggttcgg ttaatactgc gaatcacttt aatgcatggg cacagcaagg gttaaccta      60 ggtacaatg                                                             69

<210> SEQ ID NO 34
<211> LENGTH: 67
<212> TYPE: DNA
<213> ORGANISM: Artificial Sequence
<220> FEATURE:
<223> OTHER INFORMATION: Description of Artificial Sequence: XyTv-105

<400> SEQUENCE: 34
gattatcaaa tcgtagcggt ggaaggctac ttctcgagtg gttccgctag tattacagtg     60
``` agctaaa                                                              67

<210> SEQ ID NO 35
<211> LENGTH: 73
<212> TYPE: DNA
<213> ORGANISM: Artificial Sequence
<220> FEATURE:
<223> OTHER INFORMATION: Description of Artificial Sequence: XyTv-110

<400> SEQUENCE: 35
gttaaagcca tggatgttag gctcatggcc gcggtgtttt aatccgcttc agtgatcact    60
acctaggcat ata                                                       73

<210> SEQ ID NO 36
<211> LENGTH: 54
<212> TYPE: DNA
<213> ORGANISM: Artificial Sequence
<220> FEATURE:
<223> OTHER INFORMATION: Description of Artificial Sequence: XyTv-109

<400> SEQUENCE: 36
ctatagatgg catgggttgc gcaattagtc ggtagctagt aaccttggcg gtgg          54

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: XyTv-108

<400> SEQUENCE: 37
aaaatagtca tgacctcaca atctgcatta gtagcctcga ggccaagcca attatgacgc    60

<210> SEQ ID NO 38
<211> LENGTH: 66
<212> TYPE: DNA
<213> ORGANISM: Artificial Sequence
<220> FEATURE:
<223> OTHER INFORMATION: Description of Artificial Sequence: XyTv-107

<400> SEQUENCE: 38
ttagtgaaat tacgtacccg tgtcgttccc aattgggatc catgttacct aatagtttag    60
catcgc                                                               66

<210> SEQ ID NO 39
<211> LENGTH: 53
<212> TYPE: DNA
<213> ORGANISM: Artificial Sequence
<220> FEATURE:
<223> OTHER INFORMATION: Description of Artificial Sequence: XyTv-106

<400> SEQUENCE: 39
caccttccga tgaagagctc accaaggcga tcataatgtc actcgatttc tag           53

<210> SEQ ID NO 40
<211> LENGTH: 596
<212> TYPE: DNA
<213> ORGANISM: Artificial Sequence
<220> FEATURE:
<223> OTHER INFORMATION: Description of Artificial Sequence: TrX

<400> SEQUENCE: 40
ctagctaagg aggctgcaga tgcaaacaat acaaccagga accggttaca acaacggtta    60

-continued

```
cttttacagc tattggaacg atggccatgg tggtgttacc tatacaaacg ggcccggagg      120
ccaatttagc gtcaattggt ctaactccgg aaacttcgta ggtggaaaag gttggcaacc      180
cgggaccaaa aataaggtga tcaacttctc tggatcttat aatccgaatg ggaattcata      240
cttaagcgtc tatggctggt ctagaaaccc actgattgaa tattacattg tcgaaaattt      300
cggtacctac aatccgagta ccggcgccac aaaattaggc gaagtcacta gtgatggatc      360
cgtatatgat atctaccgta cccaacgcgt taatcagcca tcgatcattg gaaccgccac      420
cttttatcag tactggagtg ttagacgtaa tcatcggagc tccggttcgg ttaatactgc      480
gaatcacttt aatgcatggg cacagcaagg gttaaccta ggtacaatgg attatcaaat      540
cgtagcggtg gaaggctact ctcgagtgg ttccgctagt attacagtga gctaaa         596
```

<210> SEQ ID NO 41
<211> LENGTH: 84
<212> TYPE: DNA
<213> ORGANISM: Artificial Sequence
<220> FEATURE:
<223> OTHER INFORMATION: Description of Artificial Sequence: Secretion
      leader sequence of prot. A

<400> SEQUENCE: 41

```
ctagcaagaa gacagcaata gcaatcgctg tggcattagc cggctttgcg accgttgctc      60
aggcccagac catacaacca ggaa                                            84
```

<210> SEQ ID NO 42
<211> LENGTH: 84
<212> TYPE: DNA
<213> ORGANISM: Artificial Sequence
<220> FEATURE:
<223> OTHER INFORMATION: Description of Artificial Sequence:
      Complementary secretion leader sequence of prot. A

<400> SEQUENCE: 42

```
gttcttctgt cgttatcgtt agcgacaccg taatcggccg aaacgctggc aacgagtccg      60
ggtctggtat gttggtcctt ggcc                                            84
```

<210> SEQ ID NO 43
<211> LENGTH: 112
<212> TYPE: DNA
<213> ORGANISM: Artificial Sequence
<220> FEATURE:
<223> OTHER INFORMATION: Description of Artificial Sequence: TrX-HML

<400> SEQUENCE: 43

```
ctagctaagg aggctgcaga tgcaaacaat acaaccagga accggttacc acaacggtta      60
cttttacagc tattggaacg atggccatgg aggcgtcaca atgactctgg gg              112
```

<210> SEQ ID NO 44
<211> LENGTH: 108
<212> TYPE: DNA
<213> ORGANISM: Artificial Sequence
<220> FEATURE:
<223> OTHER INFORMATION: Description of Artificial Sequence: TrX-HML
      Complementary sequence

<400> SEQUENCE: 44

```
gattcctccg acgtctacgt tgttatgtt ggtccttggc caatggtgtt gccaatgaaa       60
atgtcgataa ccttgctacc ggtacctccg cagtgttact gagacccc                   108
```

<210> SEQ ID NO 45

```
<211> LENGTH: 39
<212> TYPE: DNA
<213> ORGANISM: Artificial Sequence
<220> FEATURE:
<223> OTHER INFORMATION: Description of Artificial Sequence: TX-10H-1

<400> SEQUENCE: 45
ggaaccggtt accacaacgg ttacttttac agctattgg                              39

<210> SEQ ID NO 46
<211> LENGTH: 39
<212> TYPE: DNA
<213> ORGANISM: Artificial Sequence
<220> FEATURE:
<223> OTHER INFORMATION: Description of Complementary Artificial
      Sequence: TX-10H11D-1

<400> SEQUENCE: 46
ggaaccggtt accacgacgg ttacttttac agctattgg                              39

<210> SEQ ID NO 47
<211> LENGTH: 44
<212> TYPE: DNA
<213> ORGANISM: Artificial Sequence
<220> FEATURE:
<223> OTHER INFORMATION: Description of Artificial Sequence: Tx-C1

<400> SEQUENCE: 47
cccaagcttc aagatcttta gctcactgta atactagcgg aacc                        44

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Tx-58R-1

<400> SEQUENCE: 48
caacccggga ccaaaaatag ggtgatcaac                                        30

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Tx-40H-1

<400> SEQUENCE: 49
gtcaattggc ataactccgg aaacttcgta ggtgga                                 36

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Tx-40R-1

<400> SEQUENCE: 50
gtcaattggc gtaactccgg aaacttcgta ggtgga                                 36

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Tx-99C-1
```

```
<400> SEQUENCE: 51
ttcggtacct acaatccgtg taccggc                                        27

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Tx-75A-1

<400> SEQUENCE: 52
tgggaattca tacttagccg tctatggctg gtctag                              36

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Tx-118C-1

<400> SEQUENCE: 53
gacggatccg tatatgatat ctgccgtacc caacgc                              36

<210> SEQ ID NO 54
<211> LENGTH: 57
<212> TYPE: DNA
<213> ORGANISM: Artificial Sequence
<220> FEATURE:
<223> OTHER INFORMATION: Description of Artificial Sequence:
     Tx-99C105H-1r

<400> SEQUENCE: 54
tacggatcca tcactagtga cttcgccgtg ttttgtggcg ccggtacacg gattgta       57

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: Tx-40C-1

<400> SEQUENCE: 55
gtcaattggt gtaactccgg aaacttcgta ggtgga                              36

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Tx-40Y-1

<400> SEQUENCE: 56
gtcaattggt ataactccgg aaacttcgta ggtgga                              36

<210> SEQ ID NO 57
<211> LENGTH: 36
<212> TYPE: DNA
<213> ORGANISM: Artificial Sequence
<220> FEATURE:
<223> OTHER INFORMATION: Description of Artificial Sequence: Tx-40F-1

<400> SEQUENCE: 57
gtcaattggt ttaactccgg aaacttcgta ggtgga                              36

<210> SEQ ID NO 58
```

```
<211> LENGTH: 36
<212> TYPE: DNA
<213> ORGANISM: Artificial Sequence
<220> FEATURE:
<223> OTHER INFORMATION: Description of Artificial Sequence: Tx-40T-1

<400> SEQUENCE: 58
gtcaattgga ctaactccgg aaacttcgta ggtgga                              36

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Tx-40A-1

<400> SEQUENCE: 59
gtcaattggg ctaactccgg aaacttcgta ggtgga                              36

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: Tx-52C-1r

<400> SEQUENCE: 60
gtcccgggac accaaccttt tccacctacg aagt                                34

<210> SEQ ID NO 61
<211> LENGTH: 306
<212> TYPE: DNA
<213> ORGANISM: Artificial Sequence
<220> FEATURE:
<223> OTHER INFORMATION: Description of Artificial Sequence: TrX(1-91)

<400> SEQUENCE: 61
ctagctaagg aggctgcaga tgcaaacaat acaaccagga accggttaca acaacggtta    60
cttttacagc tattggaacg atggccatgg tggtgttacc tatacaaacg ggcccggagg   120
ccaatttagc gtcaattggt ctaactccgg aaacttcgta ggtggaaaag gttggcaacc   180
cgggaccaaa aataaggtga tcaacttctc tggatcttat aatccgaatg gaattcata   240 cttaagcgtc tatggctggt ctagaaaccc actgattgaa tattacattg tcgaaaattt   300
cggtac                                                             306

<210> SEQ ID NO 62
<211> LENGTH: 298
<212> TYPE: DNA
<213> ORGANISM: Artificial Sequence
<220> FEATURE:
<223> OTHER INFORMATION: Description of Artificial Sequence:
      Complementary TrX(1-91)

<400> SEQUENCE: 62
gattcctccg acgtctacgt tgttatgtt ggtccttggc caatgttgtt gccaatgaaa    60
atgtcgataa ccttgctacc ggtaccacca caatggatat gtttgcccgg gcctccggtt   120
aaatcgcagt taaccagatt gaggcctttg aagcatccac cttttccaac cgttgggccc   180
tggtttttat tccactagtt gaagagacct agaatattag gcttacccct aagtatgaat   240
tcgcagatac cgaccagatc tttgggtgac taacttataa tgtaacagct tttaaagc     298

<210> SEQ ID NO 63
```

```
<211> LENGTH: 290
<212> TYPE: DNA
<213> ORGANISM: Artificial Sequence
<220> FEATURE:
<223> OTHER INFORMATION: Description of Artificial Sequence: TrX(92-190)

<400> SEQUENCE: 63
ctacaatccg agtaccggcg ccacaaaatt aggcgaagtc actagtgatg gatccgtata      60
tgatatctac cgtacccaac gcgttaatca gccatcgatc attggaaccg ccaccttta     120 tcagtactgg agtgttagac gtaatcatcg gagctccggt tcggttaata ctgcgaatca    180
ctttaatgca tgggcacagc aagggttaac cctaggtaca atggattatc aaatcgtagc    240
ggtggaaggc tacttctcga gtggttccgc tagtattaca gtgagctaaa                290

<210> SEQ ID NO 64
<211> LENGTH: 306
<212> TYPE: DNA
<213> ORGANISM: Artificial Sequence
<220> FEATURE:
<223> OTHER INFORMATION: Description of Artificial Sequence:
      Complementary TrX(92-190)

<400> SEQUENCE: 64
gttaaagcca tggatgttag gctcatggcc gcggtgtttt aatccgcttc agtgatcact     60
acctaggcat atactataga tggcatgggt tgcgcaatta gtcggtagct agtaaccttg    120
gcggtggaaa atagtcatga cctcacaatc tgcattagta gcctcgaggc caagccaatt    180
atgacgctta gtgaaattac gtaccgtgt cgttcccaat tgggatccat gttacctaat    240
agtttagcat cgccaccttc cgatgaagag ctcaccaagg cgatcataat gtcactcgat    300
ttctag                                                               306

<210> SEQ ID NO 65
<211> LENGTH: 190
<212> TYPE: PRT
<213> ORGANISM: Artificial sequence
<220> FEATURE:
<223> OTHER INFORMATION: Modified xylanase TrX-40H

<400> SEQUENCE: 65

Gln Thr Ile Gln Pro Gly Thr Gly Tyr Asn Asn Gly Tyr Phe Tyr Ser
  1               5                  10                  15

Tyr Trp Asn Asp Gly His Gly Gly Val Thr Tyr Thr Asn Gly Pro Gly
                 20                  25                  30

Gly Gln Phe Ser Val Asn Trp His Asn Ser Gly Asn Phe Val Gly Gly
             35                  40                  45

Lys Gly Trp Gln Pro Gly Thr Lys Asn Lys Val Ile Asn Phe Ser Gly
         50                  55                  60

Ser Tyr Asn Pro Asn Gly Asn Ser Tyr Leu Ser Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
```

```
145                 150                 155                 160
Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 66
<211> LENGTH: 190
<212> TYPE: PRT
<213> ORGANISM: Artificial sequence
<220> FEATURE:
<223> OTHER INFORMATION: Modified xylanase TrX-99C-118C

<400> SEQUENCE: 66

Gln Thr Ile Gln Pro Gly Thr Gly Tyr Asn Asn Gly Tyr Phe Tyr Ser
 1               5                  10                  15

Tyr Trp Asn Asp Gly His Gly Gly Val Thr Tyr Thr Asn Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
 50                  55                  60

Ser Tyr Asn Pro Asn Gly Asn Ser Tyr Leu Ser Val Tyr Gly Trp Ser
 65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys Leu Gly Glu Val Thr Ser Asp Gly
            100                 105                 110

Ser Val Tyr Asp Ile Cys Arg Thr Gln Arg Val Asn Gln Pro Ser Ile
        115                 120                 125

Ile Gly Thr Ala Thr Phe Tyr Gln Tyr Trp Ser Val Arg Arg Asn His
130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 67
<211> LENGTH: 190
<212> TYPE: PRT
<213> ORGANISM: Artificial sequence
<220> FEATURE:
<223> OTHER INFORMATION: Modified xylanase TrX-40H-99C-118C

<400> SEQUENCE: 67

Gln Thr Ile Gln Pro Gly Thr Gly Tyr Asn Asn Gly Tyr Phe Tyr Ser
 1               5                  10                  15

Tyr Trp Asn Asp Gly His Gly Gly Val Thr Tyr Thr Asn Gly Pro Gly
                20                  25                  30

Gly Gln Phe Ser Val Asn Trp His Asn Ser Gly Asn Phe Val Gly Gly
            35                  40                  45

Lys Gly Trp Gln Pro Gly Thr Lys Asn Lys Val Ile Asn Phe Ser Gly
 50                  55                  60

Ser Tyr Asn Pro Asn Gly Asn Ser Tyr Leu Ser Val Tyr Gly Trp Ser
 65                  70                  75                  80
```

Arg Asn Pro Leu Ile Glu Tyr Tyr Ile Val Glu Asn Phe Gly Thr Tyr
              85                  90                  95

Asn Pro Cys Thr Gly Ala Thr Lys Leu Gly Glu Val Thr Ser Asp Gly
            100                 105                 110

Ser Val Tyr Asp Ile Cys Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 68
<211> LENGTH: 190
<212> TYPE: PRT
<213> ORGANISM: Artificial sequence
<220> FEATURE:
<223> OTHER INFORMATION: Modified xylanase TrX-58R-99C-118C

<400> SEQUENCE: 68

Gln Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Arg Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
              85                  90                  95

Asn Pro Cys Thr Gly Ala Thr Lys Leu Gly Glu Val Thr Ser Asp Gly
            100                 105                 110

Ser Val Tyr Asp Ile Cys Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 69
<211> LENGTH: 190
<212> TYPE: PRT
<213> ORGANISM: Artificial sequence
<220> FEATURE:
<223> OTHER INFORMATION: Modified xylanase TrX-40H-58R-99C-118C

<400> SEQUENCE: 69

Gln Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
                20                  25                  30

Gly Gln Phe Ser Val Asn Trp His Asn Ser Gly Asn Phe Val Gly Gly
            35                  40                  45

Lys Gly Trp Gln Pro Gly Thr Lys Asn Arg Val Ile Asn Phe Ser Gly
 50                  55                  60

Ser Tyr Asn Pro Asn Gly Asn Ser Tyr Leu Ser Val Tyr Gly Trp Ser
 65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys Leu Gly Glu Val Thr Ser Asp Gly
                100                 105                 110

Ser Val Tyr Asp Ile Cys Arg Thr Gln Arg Val Asn Gln Pro Ser Ile
            115                 120                 125

Ile Gly Thr Ala Thr Phe Tyr Gln Tyr Trp Ser Val Arg Arg Asn His
130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 70
<211> LENGTH: 190
<212> TYPE: PRT
<213> ORGANISM: Artificial sequence
<220> FEATURE:
<223> OTHER INFORMATION: Modified xylanase TrX-HML-40R-58R-99C-118C

<400> SEQUENCE: 70

Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly Pro Gly
                20                  25                  30

Gly Gln Phe Ser Val Asn Trp Arg Asn Ser Gly Asn Phe Val Gly Gly
            35                  40                  45

Lys Gly Trp Gln Pro Gly Thr Lys Asn Arg Val Ile Asn Phe Ser Gly
 50                  55                  60

Ser Tyr Asn Pro Asn Gly Asn Ser Tyr Leu Ser Val Tyr Gly Trp Ser
 65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys Leu Gly Glu Val Thr Ser Asp Gly
                100                 105                 110

Ser Val Tyr Asp Ile Cys Arg Thr Gln Arg Val Asn Gln Pro Ser Ile
            115                 120                 125

Ile Gly Thr Ala Thr Phe Tyr Gln Tyr Trp Ser Val Arg Arg Asn His
130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

-continued

<210> SEQ ID NO 71
<211> LENGTH: 190
<212> TYPE: PRT
<213> ORGANISM: Artificial Sequence
<220> FEATURE:
<223> OTHER INFORMATION: Modified xylanase TrX-HML-40R-58R-75A-99C-118C

<400> SEQUENCE: 71

Gln Thr Ile Gln Pro Gly Thr Gly Tyr His Asn Gly Tyr Phe Tyr Ser
1               5                   10                  15

Tyr Trp Asn Asp Gly His Gly Gly Val Thr Met Thr Leu Gly Pro Gly
            20                  25                  30

Gly Gln Phe Ser Val Asn Trp Arg Asn Ser Gly Asn Phe Val Gly Gly
        35                  40                  45

Lys Gly Trp Gln Pro Gly Thr Lys Asn Arg Val Ile Asn Phe Ser Gly
    50                  55                  60

Ser Tyr Asn Pro Asn Gly Asn Ser Tyr Leu Ala Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys Leu Gly Glu Val Thr Ser Asp Gly
            100                 105                 110

Ser Val Tyr Asp Ile Cys Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 72
<211> LENGTH: 190
<212> TYPE: PRT
<213> ORGANISM: Artificial Sequence
<220> FEATURE:
<223> OTHER INFORMATION: Modified xylanase TrX-HML-75A-99C-105H-118C-
    125A-129E

<400> SEQUENCE: 72

Gln Thr Ile Gln Pro Gly Thr Gly Tyr His Asn Gly Tyr Phe Tyr Ser
1               5                   10                  15

Tyr Trp Asn Asp Gly His Gly Gly Val Thr Met Thr Leu Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ala Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
            115                 120                 125

Glu Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 73
<211> LENGTH: 190
<212> TYPE: PRT
<213> ORGANISM: Artificial sequence
<220> FEATURE:
<223> OTHER INFORMATION: Modified xylanase TrX-HML-58R-75A-99C-105H-
      118C-125A-129E

<400> SEQUENCE: 73

Gln Thr Ile Gln Pro Gly Thr Gly Tyr His Asn Gly Tyr Phe Tyr Ser
1               5                   10                  15

Tyr Trp Asn Asp Gly His Gly Gly Val Thr Met Thr Leu Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Arg Val Ile Asn Phe Ser Gly
    50                  55                  60

Ser Tyr Asn Pro Asn Gly Asn Ser Tyr Leu Ala Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
            115                 120                 125

Glu Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 74
<211> LENGTH: 190
<212> TYPE: PRT
<213> ORGANISM: Artificial Sequence
<220> FEATURE:
<223> OTHER INFORMATION: Modified xylanase TrX-10H-11D-27M-29L-58R-75A-
      99C-105H-118C-125A-129E

<400> SEQUENCE: 74

Gln Thr Ile Gln Pro Gly Thr Gly Tyr His Asp Gly Tyr Phe Tyr Ser
1               5                   10                  15

Tyr Trp Asn Asp Gly His Gly Gly Val Thr Met Thr Leu Gly Pro Gly
            20                  25                  30

```
Gly Gln Phe Ser Val Asn Trp Ser Asn Ser Gly Asn Phe Val Gly Gly
            35                  40                  45

Lys Gly Trp Gln Pro Gly Thr Lys Asn Arg Val Ile Asn Phe Ser Gly
 50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
            115                 120                 125

Glu Gly Thr Ala Thr Phe Tyr Gln Tyr Trp Ser Val Arg Arg Asn His
130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 75
<211> LENGTH: 190
<212> TYPE: PRT
<213> ORGANISM: Artificial Sequence
<220> FEATURE:
<223> OTHER INFORMATION: Modified xylanase TrX-10H-11D-27M-29L-40C-58R-75A-99C-105H-118C-125A-129E

<400> SEQUENCE: 75

```
Gln Thr Ile Gln Pro Gly Thr Gly Tyr His Asp Gly Tyr Phe Tyr Ser
 1               5                  10                  15

Tyr Trp Asn Asp Gly His Gly Val Thr Met Thr Leu Gly Pro Gly
                20                  25                  30

Gly Gln Phe Ser Val Asn Trp Cys Asn Ser Gly Asn Phe Val Gly Gly
            35                  40                  45

Lys Gly Trp Gln Pro Gly Thr Lys Asn Arg Val Ile Asn Phe Ser Gly
 50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
            115                 120                 125

Glu Gly Thr Ala Thr Phe Tyr Gln Tyr Trp Ser Val Arg Arg Asn His
130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 76

<211> LENGTH: 190
<212> TYPE: PRT
<213> ORGANISM: Artificial Sequence
<220> FEATURE:
<223> OTHER INFORMATION: Modified xylanase TrX-10H-11D-27M-29L-40F-58R-
75A-99C-105H-118C-125A-129E

<400> SEQUENCE: 76

Gln Thr Ile Gln Pro Gly Thr Gly Tyr His Asp Gly Tyr Phe Tyr Ser
1               5                   10                  15

Tyr Trp Asn Asp Gly His Gly Gly Val Thr Met Thr Leu Gly Pro Gly
            20                  25                  30

Gly Gln Phe Ser Val Asn Trp Phe Asn Ser Gly Asn Phe Val Gly Gly
        35                  40                  45

Lys Gly Trp Gln Pro Gly Thr Lys Asn Arg Val Ile Asn Phe Ser Gly
    50                  55                  60

Ser Tyr Asn Pro Asn Gly Asn Ser Tyr Leu Ala Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
        115                 120                 125

Glu Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 77
<211> LENGTH: 190
<212> TYPE: PRT
<213> ORGANISM: Artificial sequence
<220> FEATURE:
<223> OTHER INFORMATION: Modified xylanase TrX-10H-11D-27M-29L-40H-58R-
75A-99C-105H-118C-125A-129E

<400> SEQUENCE: 77

Gln Thr Ile Gln Pro Gly Thr Gly Tyr His Asp Gly Tyr Phe Tyr Ser
1               5                   10                  15

Tyr Trp Asn Asp Gly His Gly Gly Val Thr Met Thr Leu Gly Pro Gly
            20                  25                  30

Gly Gln Phe Ser Val Asn Trp His Asn Ser Gly Asn Phe Val Gly Gly
        35                  40                  45

Lys Gly Trp Gln Pro Gly Thr Lys Asn Arg Val Ile Asn Phe Ser Gly
    50                  55                  60

Ser Tyr Asn Pro Asn Gly Asn Ser Tyr Leu Ala Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
        115                 120                 125

Glu Gly Thr Ala Thr Phe Tyr Gln Tyr Trp Ser Val Arg Arg Asn His
            130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 78
<211> LENGTH: 190
<212> TYPE: PRT
<213> ORGANISM: Artificial sequence
<220> FEATURE:
<223> OTHER INFORMATION: Modified xylanase TrX-H-11D-ML-40Y-58R-75A-99C-
      105H-118C-125A-129E

<400> SEQUENCE: 78

Gln Thr Ile Gln Pro Gly Thr Gly Tyr His Asp Gly Tyr Phe Tyr Ser
1               5                   10                  15

Tyr Trp Asn Asp Gly His Gly Gly Val Thr Met Thr Leu Gly Pro Gly
            20                  25                  30

Gly Gln Phe Ser Val Asn Trp Tyr Asn Ser Gly Asn Phe Val Gly Gly
        35                  40                  45

Lys Gly Trp Gln Pro Gly Thr Lys Asn Arg Val Ile Asn Phe Ser Gly
    50                  55                  60

Ser Tyr Asn Pro Asn Gly Asn Ser Tyr Leu Ala Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
        115                 120                 125

Glu Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 79
<211> LENGTH: 190
<212> TYPE: PRT
<213> ORGANISM: Artificial sequence
<220> FEATURE:
<223> OTHER INFORMATION: Modified xylanase TrX-10H-11D-27M-29L-40R-58R-
      75A-99C-105H-118C-125A-129E

<400> SEQUENCE: 79

Gln Thr Ile Gln Pro Gly Thr Gly Tyr His Asp Gly Tyr Phe Tyr Ser
1               5                   10                  15

Tyr Trp Asn Asp Gly His Gly Gly Val Thr Met Thr Leu Gly Pro Gly
            20                  25                  30

Gly Gln Phe Ser Val Asn Trp Arg Asn Ser Gly Asn Phe Val Gly Gly
        35                  40                  45

-continued

```
Lys Gly Trp Gln Pro Gly Thr Lys Asn Arg Val Ile Asn Phe Ser Gly
 50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
        115                 120                 125

Glu Gly Thr Ala Thr Phe Tyr Gln Tyr Trp Ser Val Arg Arg Asn His
130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 80
<211> LENGTH: 190
<212> TYPE: PRT
<213> ORGANISM: Artificial sequence
<220> FEATURE:
<223> OTHER INFORMATION: Modified xylanase TrX-10H-11D-27M-29L-40H-52C-
      58R-75A-99C-105H-118C-125A-129E

<400> SEQUENCE: 80

```
Gln Thr Ile Gln Pro Gly Thr Gly Tyr His Asp Gly Tyr Phe Tyr Ser
  1               5                  10                  15

Tyr Trp Asn Asp Gly His Gly Val Thr Met Thr Leu Gly Pro Gly
                 20                  25                  30

Gly Gln Phe Ser Val Asn Trp His Asn Ser Gly Asn Phe Val Gly Gly
            35                  40                  45

Lys Gly Trp Cys Pro Gly Thr Lys Asn Arg Val Ile Asn Phe Ser Gly
 50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
        115                 120                 125

Glu Gly Thr Ala Thr Phe Tyr Gln Tyr Trp Ser Val Arg Arg Asn His
130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 81
<211> LENGTH: 190
<212> TYPE: PRT

<213> ORGANISM: Artificial sequence
<220> FEATURE:
<223> OTHER INFORMATION: Modified xylanase TrX-10H-11D-27M-29L-40R-58R-
75A-99C-105H-118C-125A-129E-144R-161R

<400> SEQUENCE: 81

Gln Thr Ile Gln Pro Gly Thr Gly Tyr His Asp Gly Tyr Phe Tyr Ser
 1               5                  10                  15

Tyr Trp Asn Asp Gly His Gly Gly Val Thr Met Thr Leu Gly Pro Gly
                20                  25                  30

Gly Gln Phe Ser Val Asn Trp Arg Asn Ser Gly Asn Phe Val Gly Gly
            35                  40                  45

Lys Gly Trp Gln Pro Gly Thr Lys Asn Arg Val Ile Asn Phe Ser Gly
        50                  55                  60

Ser Tyr Asn Pro Asn Gly Asn Ser Tyr Leu Ala Val Tyr Gly Trp Ser
 65                 70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys His Gly Glu Val Thr Ser Asp Gly
           100                 105                 110

Ser Val Tyr Asp Ile Cys Arg Thr Gln Arg Val Asn Ala Pro Ser Ile
       115                 120                 125

Glu Gly Thr Ala Thr Phe Tyr Gln Tyr Trp Ser Val Arg Arg Asn Arg
   130                 135                 140

Arg Ser Ser Gly Ser Val Asn Thr Ala Asn His Phe Asn Ala Trp Ala
145                 150                 155                 160

Arg Gln Gly Leu Thr Leu Gly Thr Met Asp Tyr Gln Ile Val Ala Val
               165                  170                 175

Glu Gly Tyr Phe Ser Ser Gly Ser Ala Ser Ile Thr Val Ser
           180                 185                 190

<210> SEQ ID NO 82
<211> LENGTH: 190
<212> TYPE: PRT
<213> ORGANISM: Artificial sequence
<220> FEATURE:
<223> OTHER INFORMATION: Modified xylanase TrX-10H-11D-27M-29L-58R-75A-
99C-105H-118C-125A-129E-131N

<400> SEQUENCE: 82

Gln Thr Ile Gln Pro Gly Thr Gly Tyr His Asp Gly Tyr Phe Tyr Ser
 1               5                  10                  15

Tyr Trp Asn Asp Gly His Gly Gly Val Thr Met Thr Leu Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Arg Val Ile Asn Phe Ser Gly
        50                  55                  60

Ser Tyr Asn Pro Asn Gly Asn Ser Tyr Leu Ala Val Tyr Gly Trp Ser
 65                 70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys His Gly Glu Val Thr Ser Asp Gly
           100                 105                 110

Ser Val Tyr Asp Ile Cys Arg Thr Gln Arg Val Asn Ala Pro Ser Ile
       115                 120                 125

Glu Gly Asn Ala Thr Phe Tyr Gln Tyr Trp Ser Val Arg Arg Asn His

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 83
<211> LENGTH: 20
<212> TYPE: PRT
<213> ORGANISM: Artificial sequence
<220> FEATURE:
<223> OTHER INFORMATION: S75A primer

<400> SEQUENCE: 83

Ala Gly Cys Thr Ala Cys Cys Thr Cys Gly Cys Gly Thr Gly Thr
1               5                   10                  15

Ala Cys Gly Gly
            20

<210> SEQ ID NO 84
<211> LENGTH: 19
<212> TYPE: PRT
<213> ORGANISM: Artificial sequence
<220> FEATURE:
<223> OTHER INFORMATION: L105H primer

<400> SEQUENCE: 84

Cys Cys Ala Cys Cys Ala Ala Gly Cys Ala Cys Gly Gly Cys Gly Ala
1               5                   10                  15

Gly Gly Thr

<210> SEQ ID NO 85
<211> LENGTH: 33
<212> TYPE: PRT
<213> ORGANISM: Artificial sequence
<220> FEATURE:
<223> OTHER INFORMATION: S125A primer

<400> SEQUENCE: 85

Ala Cys Gly Cys Ala Gly Cys Gly Cys Gly Thr Cys Ala Ala Cys Gly
1               5                   10                  15

Cys Cys Cys Cys Gly Thr Cys Cys Ala Thr Cys Ala Thr Cys Gly Gly
                20                  25                  30

Cys

<210> SEQ ID NO 86
<211> LENGTH: 33
<212> TYPE: PRT
<213> ORGANISM: Artificial sequence
<220> FEATURE:
<223> OTHER INFORMATION: I129E primer

<400> SEQUENCE: 86

Ala Ala Cys Gly Cys Cys Cys Cys Gly Thr Cys Cys Ala Thr Cys Gly
1               5                   10                  15

Ala Gly Gly Gly Cys Ala Cys Cys Gly Cys Cys Ala Cys Thr Thr
                20                  25                  30

Thr

```
<210> SEQ ID NO 87
<211> LENGTH: 27
<212> TYPE: PRT
<213> ORGANISM: Artificial sequence
<220> FEATURE:
<223> OTHER INFORMATION: K58R primer

<400> SEQUENCE: 87

Gly Gly Cys Ala Cys Cys Ala Ala Gly Ala Ala Cys Cys Gly Cys Thr
 1               5                   10                  15

Ala Ala Gly Ala Cys Thr Ala Cys Cys Thr Ala
             20                  25

<210> SEQ ID NO 88
<211> LENGTH: 27
<212> TYPE: PRT
<213> ORGANISM: Artificial sequence
<220> FEATURE:
<223> OTHER INFORMATION: S99C primer

<400> SEQUENCE: 88

Ala Cys Cys Thr Ala Cys Ala Ala Cys Cys Cys Gly Thr Gly Cys Ala
 1               5                   10                  15

Cys Gly Gly Gly Cys Gly Cys Cys Ala Cys Cys
             20                  25

<210> SEQ ID NO 89
<211> LENGTH: 20
<212> TYPE: PRT
<213> ORGANISM: Artificial sequence
<220> FEATURE:
<223> OTHER INFORMATION: Y118C primer

<400> SEQUENCE: 89

Cys Thr Ala Cys Gly Ala Cys Ala Thr Thr Thr Gly Cys Cys Gly Cys
 1               5                   10                  15

Ala Cys Gly Cys
             20

<210> SEQ ID NO 90
<211> LENGTH: 19
<212> TYPE: PRT
<213> ORGANISM: Artificial sequence
<220> FEATURE:
<223> OTHER INFORMATION: N11D primer

<400> SEQUENCE: 90

Gly Gly Thr Thr Ala Cys Cys Ala Cys Gly Ala Cys Gly Gly Thr Thr
 1               5                   10                  15

Ala Cys Thr

<210> SEQ ID NO 91
<211> LENGTH: 27
<212> TYPE: PRT
<213> ORGANISM: Artificial sequence
<220> FEATURE:
<223> OTHER INFORMATION: S40R primer

<400> SEQUENCE: 91

Thr Cys Cys Gly Thr Cys Ala Ala Cys Thr Gly Gly Cys Gly Cys Ala
 1               5                   10                  15

Ala Cys Thr Cys Gly Gly Gly Cys Ala Ala Cys
             20                  25
```

```
<210> SEQ ID NO 92
<211> LENGTH: 30
<212> TYPE: PRT
<213> ORGANISM: Artificial sequence
<220> FEATURE:
<223> OTHER INFORMATION: T131N primer

<400> SEQUENCE: 92

Cys Cys Gly Thr Cys Cys Ala Thr Cys Gly Ala Gly Gly Cys Ala
 1               5                  10                  15

Ala Cys Gly Cys Cys Ala Cys Cys Thr Thr Thr Thr Ala Cys
                20                  25                  30

<210> SEQ ID NO 93
<211> LENGTH: 27
<212> TYPE: PRT
<213> ORGANISM: Artificial sequence
<220> FEATURE:
<223> OTHER INFORMATION: Amino Acids 2 to 28 of Secretion Leader
      Sequence of prot. a

<400> SEQUENCE: 93

Lys Lys Thr Ala Ile Ala Ile Ala Val Ala Leu Ala Gly Phe Ala Thr
 1               5                  10                  15

Val Ala Gln Ala Gln Thr Ile Gln Pro Gly Thr
                20                  25

<210> SEQ ID NO 94
<211> LENGTH: 30
<212> TYPE: PRT
<213> ORGANISM: Artificial sequence
<220> FEATURE:
<223> OTHER INFORMATION: Amino Acids 1 through 30 of TrX-HML

<400> SEQUENCE: 94

Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly
                20                  25                  30

<210> SEQ ID NO 95
<211> LENGTH: 13
<212> TYPE: PRT
<213> ORGANISM: Artificial sequence
<220> FEATURE:
<223> OTHER INFORMATION: Amino Acids 6 to 18 of TX-10H-1

<400> SEQUENCE: 95

Gly Thr Gly Tyr His Asn Gly Tyr Phe Tyr Ser Tyr Trp
 1               5                  10

<210> SEQ ID NO 96
<211> LENGTH: 13
<212> TYPE: PRT
<213> ORGANISM: Artificial sequence
<220> FEATURE:
<223> OTHER INFORMATION: Amino Acids 6 to 18 of complementary sequence
      TX-10H11D-1

<400> SEQUENCE: 96

Gly Thr Gly Tyr His Asp Gly Tyr Phe Tyr Ser Tyr Trp
 1               5                  10

<210> SEQ ID NO 97
<211> LENGTH: 8
<212> TYPE: PRT
```

-continued

```
<213> ORGANISM: Artificial sequence
<220> FEATURE:
<223> OTHER INFORMATION: Amino Acids 183 to 190 of TX-Cl

<400> SEQUENCE: 97

Gly Ser Ala Ser Ile Thr Val Ser
 1               5

<210> SEQ ID NO 98
<211> LENGTH: 9
<212> TYPE: PRT
<213> ORGANISM: Artificial sequence
<220> FEATURE:
<223> OTHER INFORMATION: Amino Acids 53 to 61 of TX-58R-1

<400> SEQUENCE: 98

Pro Gly Thr Lys Asn Arg Val Ile Asn
 1               5

<210> SEQ ID NO 99
<211> LENGTH: 10
<212> TYPE: PRT
<213> ORGANISM: Artificial sequence
<220> FEATURE:
<223> OTHER INFORMATION: Amino Acids 39 to 48 of TX-40H-1

<400> SEQUENCE: 99

Trp His Asn Ser Gly Asn Phe Val Gly Gly
 1               5                  10

<210> SEQ ID NO 100
<211> LENGTH: 10
<212> TYPE: PRT
<213> ORGANISM: Artificial sequence
<220> FEATURE:
<223> OTHER INFORMATION: Amino Acids 39 to 48 of TX-40R-1

<400> SEQUENCE: 100

Trp Arg Asn Ser Gly Asn Phe Val Gly Gly
 1               5                  10

<210> SEQ ID NO 101
<211> LENGTH: 7
<212> TYPE: PRT
<213> ORGANISM: Artificial sequence
<220> FEATURE:
<223> OTHER INFORMATION: Amino Acids 95 to 101 of TX-99C-1

<400> SEQUENCE: 101

Thr Tyr Asn Pro Cys Thr Gly
 1               5

<210> SEQ ID NO 102
<211> LENGTH: 13
<212> TYPE: PRT
<213> ORGANISM: Artificial sequence
<220> FEATURE:
<223> OTHER INFORMATION: Amino Acids 69 to 81 of TX-75A-1

<400> SEQUENCE: 102

Asn Gly Asn Ser Tyr Leu Ala Val Tyr Gly Trp Ser Arg
 1               5                  10

<210> SEQ ID NO 103
<211> LENGTH: 12
<212> TYPE: PRT
<213> ORGANISM: Artificial sequence
```

```
<220> FEATURE:
<223> OTHER INFORMATION: Amino Acids 111 to 122 of TX-118C-1

<400> SEQUENCE: 103

Asp Gly Ser Val Tyr Asp Ile Cys Arg Thr Gln Arg
1               5                   10

<210> SEQ ID NO 104
<211> LENGTH: 19
<212> TYPE: PRT
<213> ORGANISM: Artificial sequence
<220> FEATURE:
<223> OTHER INFORMATION: Amino acids 114 to 96 of TX-99C-105H-1r

<400> SEQUENCE: 104

Val Ser Gly Asp Ser Thr Val Glu Gly His Lys Thr Ala Gly Thr Cys
1               5                   10                  15

Pro Asn Tyr

<210> SEQ ID NO 105
<211> LENGTH: 10
<212> TYPE: PRT
<213> ORGANISM: Artificial sequence
<220> FEATURE:
<223> OTHER INFORMATION: Amino Acids 39 to 48 of TX-40C-1

<400> SEQUENCE: 105

Trp Cys Asn Ser Gly Asn Phe Val Gly Gly
1               5                   10

<210> SEQ ID NO 106
<211> LENGTH: 10
<212> TYPE: PRT
<213> ORGANISM: Artificial sequence
<220> FEATURE:
<223> OTHER INFORMATION: Amino Acids 39 to 48 of TX-40Y-1

<400> SEQUENCE: 106

Trp Tyr Asn Ser Gly Asn Phe Val Gly Gly
1               5                   10

<210> SEQ ID NO 107
<211> LENGTH: 10
<212> TYPE: PRT
<213> ORGANISM: Artificial sequence
<220> FEATURE:
<223> OTHER INFORMATION: Amino Acids 39 to 48 of TX-40F-1

<400> SEQUENCE: 107

Trp Phe Asn Ser Gly Asn Phe Val Gly Gly
1               5                   10

<210> SEQ ID NO 108
<211> LENGTH: 10
<212> TYPE: PRT
<213> ORGANISM: Artificial sequence
<220> FEATURE:
<223> OTHER INFORMATION: Amino Acids 39 to 48 of TX-40T-1

<400> SEQUENCE: 108

Trp Thr Asn Ser Gly Asn Phe Val Gly Gly
1               5                   10

<210> SEQ ID NO 109
<211> LENGTH: 10
<212> TYPE: PRT
```

```
<213> ORGANISM: Artificial sequence
<220> FEATURE:
<223> OTHER INFORMATION: Amino acids 39 to 48 of TX-40A-1

<400> SEQUENCE: 109

Trp Ala Asn Ser Gly Asn Phe Val Gly Gly
 1               5                  10

<210> SEQ ID NO 110
<211> LENGTH: 11
<212> TYPE: PRT
<213> ORGANISM: Artificial sequence
<220> FEATURE:
<223> OTHER INFORMATION: Amino Acids 54 to 44 of TX-52C-1r

<400> SEQUENCE: 110

Gly Pro Cys Trp Gly Lys Gly Gly Val Phe Asn
 1               5                  10
```